(12) United States Patent
McMorrow et al.

(10) Patent No.: US 8,167,803 B2
(45) Date of Patent: May 1, 2012

(54) SYSTEM AND METHOD FOR BLADDER DETECTION USING HARMONIC IMAGING

(75) Inventors: Gerald McMorrow, Redmond, WA (US); Fuxing Yang, Woodinville, WA (US)

(73) Assignee: Verathon Inc., Bothell, WA (US)

( * ) Notice: Subject to any disclaimer, the term of this patent is extended or adjusted under 35 U.S.C. 154(b) by 619 days.

(21) Appl. No.: 12/121,721

(22) Filed: May 15, 2008

(65) Prior Publication Data

US 2009/0264757 A1 Oct. 22, 2009

Related U.S. Application Data

(63) Continuation-in-part of application No. 11/968,027, filed on Dec. 31, 2007, and a continuation-in-part of application No. 11/926,522, filed on Oct. 29, 2007, now abandoned, and a continuation-in-part of application No. 11/925,887, filed on Oct. 27, 2007, now abandoned, and a continuation-in-part of application No. 11/925,896, filed on Oct. 27, 2007, now abandoned, and a continuation-in-part of application No. 11/925,900, filed on Oct. 27, 2007, now abandoned, and a continuation-in-part of application No. 11/925,850, filed on Oct. 27, 2007, and a continuation-in-part of application No. 11/925,843, filed on Oct. 27, 2007, now abandoned, and a continuation-in-part of application No. 11/925,654, filed on Oct. 26, 2007, now abandoned.

(60) Provisional application No. 60/938,359, filed on May 16, 2007, provisional application No. 60/938,371, filed on May 16, 2007, provisional application No. 60/938,446, filed on May 16, 2007.

(51) Int. Cl.
*A61B 8/00* (2006.01)
(52) U.S. Cl. ........................................ 600/437; 600/443
(58) Field of Classification Search ........... 600/437–467
See application file for complete search history.

(56) References Cited

U.S. PATENT DOCUMENTS 3,613,069 A 10/1971 Cary, Jr.
(Continued)

FOREIGN PATENT DOCUMENTS

EP 0 271 214 6/1988
(Continued)

OTHER PUBLICATIONS

Baker, A., et al.: "Distortion and High-Frequency Generation Due to Nonlinear Propagation of Short Ultrasonic Pulses from A Plane Circular Piston", Journal of Acoustical Society of America, vol. 92, No. 3, pp. 1699-1705, Sep. 1992.

(Continued)

*Primary Examiner* — Sanjay Cattungal
(74) *Attorney, Agent, or Firm* — Scott Born; Foster Pepper PLLC

(57) ABSTRACT

Systems, methods, and ultrasound transceivers equipped and configured to execute harmonic analysis and extract harmonic information related to a targeted organ of a subject are described. The methods utilize neural network algorithms to establish improved segmentation accuracy of the targeted organ or structures within a region-of-interest. The neural network algorithms, refined for detection of the bladder and to ascertain the presence or absence of a uterus, is optimally applied to better segment and thus confer the capability to optimize measurement of bladder geometry, area, and volumes.

8 Claims, 47 Drawing Sheets

U.S. PATENT DOCUMENTS

| | | | | |
|---|---|---|---|---|
| 4,431,007 A | 2/1984 | Amazeen et al. | | 128/660 |
| 4,556,066 A | 12/1985 | Semrow | | 128/660 |
| 4,757,821 A | 7/1988 | Snyder | | 128/660 |
| 4,771,205 A | 9/1988 | Mequio | | 310/334 |
| 4,821,210 A | 4/1989 | Rumbaugh | | 364/518 |
| 4,844,080 A | 7/1989 | Frass et al. | | 128/660.01 |
| 4,926,871 A | 5/1990 | Ganguly et al. | | 128/660.07 |
| 5,058,591 A | 10/1991 | Companion et al. | | 128/661.03 |
| 5,060,515 A | 10/1991 | Kanda et al. | | 73/602 |
| 5,078,149 A | 1/1992 | Katsumata et al. | | 128/662.03 |
| 5,125,410 A | 6/1992 | Misono et al. | | 128/662.06 |
| 5,148,809 A | 9/1992 | Biegeleisen-Knight et al. | | 128/660.07 |
| 5,151,856 A | 9/1992 | Halmann et al. | | 364/413.03 |
| 5,159,931 A | 11/1992 | Pini | | 128/660.07 |
| 5,197,019 A | 3/1993 | Delon-Martin et al. | | 364/563 |
| 5,235,985 A | 8/1993 | McMorrow et al. | | 128/660.07 |
| 5,265,614 A | 11/1993 | Hayakawa et al. | | 128/602.03 |
| 5,299,577 A | 4/1994 | Brown et al. | | 128/660.07 |
| 5,381,794 A | 1/1995 | Tei et al. | | 128/662.03 |
| 5,432,310 A | 7/1995 | Stoeger | | 200/82 R |
| 5,435,310 A | 7/1995 | Sheehan et al. | | 128/653.1 |
| 5,465,721 A | 11/1995 | Kishimoto et al. | | 128/660.07 |
| 5,473,555 A | 12/1995 | Potter | | 364/724.1 |
| 5,487,388 A | 1/1996 | Rello et al. | | 128/660.09 |
| 5,503,152 A | 4/1996 | Oakley et al. | | 128/661.01 |
| 5,503,153 A | 4/1996 | Liu et al. | | 128/661.08 |
| 5,526,816 A | 6/1996 | Arditi | | 128/662.02 |
| 5,553,618 A | 9/1996 | Suzuki et al. | | 128/653.1 |
| 5,575,286 A | 11/1996 | Weng et al. | | 128/653.1 |
| 5,575,291 A | 11/1996 | Hayakawa et al. | | 128/662.03 |
| 5,577,506 A | 11/1996 | Dias | | 128/662.03 |
| 5,588,435 A | 12/1996 | Weng et al. | | 128/660.07 |
| 5,601,084 A | 2/1997 | Sheehan et al. | | 128/661.04 |
| 5,605,155 A | 2/1997 | Chalana et al. | | 128/660.07 |
| 5,615,680 A | 4/1997 | Sano | | 128/661.09 |
| 5,644,513 A | 7/1997 | Rudin et al. | | 364/572 |
| 5,645,077 A | 7/1997 | Foxlin | | 128/774 |
| 5,697,525 A | 12/1997 | O'Reilly et al. | | 222/105 |
| 5,698,549 A | 12/1997 | Steers et al. | | 514/211 |
| 5,724,101 A | 3/1998 | Haskin | | 348/441 |
| 5,735,282 A | 4/1998 | Hossack | | 128/662.03 |
| 5,738,097 A | 4/1998 | Beach et al. | | 128/661.09 |
| 5,776,063 A | 7/1998 | Dittrich et al. | | 600/408 |
| 5,782,767 A | 7/1998 | Pretlow, III | | 600/443 |
| 5,806,521 A | 9/1998 | Morimoto et al. | | 128/661.01 |
| 5,841,889 A | 11/1998 | Seyed-Bolorforosh | | 382/128 |
| 5,846,202 A | 12/1998 | Ramamurthy et al. | | 600/450 |
| 5,851,186 A | 12/1998 | Wood et al. | | 600/437 |
| 5,873,829 A | 2/1999 | Kamiyama et al. | | 600/443 |
| 5,892,843 A | 4/1999 | Zhou et al. | | 382/176 |
| 5,898,793 A | 4/1999 | Karron et al. | | 382/131 |
| 5,903,664 A | 5/1999 | Hartley et al. | | 382/154 |
| 5,908,390 A | 6/1999 | Matsushima | | 600/447 |
| 5,913,823 A | 6/1999 | Hedberg et al. | | 600/443 |
| 5,928,151 A | 7/1999 | Hossack et al. | | 600/443 |
| 5,945,770 A | 8/1999 | Hanafy | | 310/322 |
| 5,964,710 A | 10/1999 | Ganguly et al. | | 600/449 |
| 5,971,923 A | 10/1999 | Finger | | 600/437 |
| 5,972,023 A | 10/1999 | Tanner et al. | | 606/219 |
| 5,980,459 A | 11/1999 | Chiao et al. | | 600/447 |
| 5,993,390 A | 11/1999 | Savord et al. | | 600/437 |
| 6,008,813 A | 12/1999 | Lauer et al. | | 345/424 |
| 6,023,977 A | * 2/2000 | Langdon et al. | | 73/629 |
| 6,030,344 A | 2/2000 | Guracar et al. | | 600/447 |
| 6,042,545 A | 3/2000 | Hossack et al. | | 600/443 |
| 6,048,312 A | 4/2000 | Ishrak et al. | | 600/443 |
| 6,063,033 A | 5/2000 | Haider et al. | | 600/447 |
| 6,064,906 A | 5/2000 | Langberg et al. | | 600/518 |
| 6,071,242 A | 6/2000 | Lin | | 600/456 |
| 6,102,858 A | 8/2000 | Hatfield et al. | | 600/443 |
| 6,106,465 A | 8/2000 | Napolitano et al. | | 600/443 |
| 6,110,111 A | 8/2000 | Barnard | | 600/438 |
| 6,117,080 A | 9/2000 | Schwartz | | 600/443 |
| 6,122,538 A | 9/2000 | Sliwa, Jr. et al. | | 600/407 |
| 6,123,669 A | 9/2000 | Kanda | | 600/443 |
| 6,126,598 A | 10/2000 | Entrekin et al. | | 600/437 |
| 6,131,458 A | * 10/2000 | Langdon et al. | | 73/627 |
| 6,132,377 A | * 10/2000 | Bolorforosh et al. | | 600/458 |
| 6,142,942 A | 11/2000 | Clark | | 600/443 |
| 6,146,330 A | 11/2000 | Tujino et al. | | 600/443 |
| 6,148,095 A | 11/2000 | Prause et al. | | 382/131 |
| 6,151,404 A | 11/2000 | Pieper | | 382/128 |
| 6,159,150 A | 12/2000 | Yale et al. | | 600/437 |
| 6,171,248 B1 | 1/2001 | Hossack et al. | | 600/459 |
| 6,193,657 B1 | 2/2001 | Drapkin | | 600/437 |
| 6,200,266 B1 | 3/2001 | Shokrollahi et al. | | 600/438 |
| 6,210,327 B1 | 4/2001 | Brackett et al. | | 600/437 |
| 6,213,949 B1 | 4/2001 | Ganguly et al. | | 600/449 |
| 6,213,951 B1 | 4/2001 | Krishnan et al. | | 600/458 |
| 6,222,948 B1 | 4/2001 | Hossack et al. | | 382/294 |
| 6,223,599 B1 | * 5/2001 | Langdon et al. | | 73/627 |
| 6,233,480 B1 | 5/2001 | Hochman et al. | | 600/476 |
| 6,238,344 B1 | 5/2001 | Gamelsky et al. | | 600/437 |
| 6,248,070 B1 | 6/2001 | Kanda et al. | | 600/443 |
| 6,254,539 B1 | 7/2001 | Pang et al. | | 600/443 |
| 6,264,609 B1 | 7/2001 | Herrington et al. | | 600/443 |
| 6,272,469 B1 | 8/2001 | Koritzinsky et al. | | 705/2 |
| 6,277,073 B1 | 8/2001 | Bolorforosh et al. | | 600/437 |
| 6,286,513 B1 | 9/2001 | Au et al. | | 128/898 |
| 6,302,845 B2 | 10/2001 | Shi et al. | | 600/438 |
| 6,309,353 B1 | 10/2001 | Cheng et al. | | 600/437 |
| 6,312,379 B1 | * 11/2001 | Bradley et al. | | 600/437 |
| 6,325,758 B1 | 12/2001 | Carol et al. | | 600/439 |
| 6,338,716 B1 | 1/2002 | Hossack et al. | | 600/459 |
| 6,343,936 B1 | 2/2002 | Kaufman et al. | | 434/262 |
| 6,346,124 B1 | 2/2002 | Geiser et al. | | 660/450 |
| 6,350,239 B1 | 2/2002 | Ohad et al. | | 600/437 |
| 6,359,190 B1 | 3/2002 | Ter-Ovanesyan et al. | | 604/361 |
| 6,360,027 B1 | 3/2002 | Hossack et al. | | 382/294 |
| 6,375,616 B1 | 4/2002 | Soferman et al. | | 600/443 |
| 6,400,848 B1 | 6/2002 | Gallagher | | 382/254 |
| 6,401,539 B1 | * 6/2002 | Langdon et al. | | 73/609 |
| 6,402,762 B2 | 6/2002 | Hunter et al. | | 606/130 |
| 6,406,431 B1 | * 6/2002 | Barnard et al. | | 600/443 |
| 6,409,665 B1 | 6/2002 | Scott et al. | | 600/437 |
| 6,440,071 B1 | 8/2002 | Slayton et al. | | 600/437 |
| 6,440,072 B1 | 8/2002 | Schuman et al. | | 600/437 |
| 6,443,894 B1 | 9/2002 | Sumanaweera et al. | | |
| 6,468,218 B1 | 10/2002 | Chen et al. | | 600/443 |
| 6,485,423 B2 | 11/2002 | Angelsen et al. | | 600/458 |
| 6,491,631 B2 | 12/2002 | Chiao et al. | | 600/443 |
| 6,494,841 B1 | * 12/2002 | Thomas et al. | | 600/447 |
| 6,503,204 B1 | 1/2003 | Sumanaweera et al. | | 600/459 |
| 6,511,325 B1 | 1/2003 | Lalka et al. | | 434/272 |
| 6,511,426 B1 | 1/2003 | Hossack et al. | | 600/437 |
| 6,511,427 B1 | 1/2003 | Sliwa, Jr. et al. | | 600/438 |
| 6,515,657 B1 | 2/2003 | Zanelli | | 345/419 |
| 6,524,249 B2 | 2/2003 | Moehring et al. | | 600/438 |
| 6,535,759 B1 | 3/2003 | Epstein et al. | | 600/547 |
| 6,540,679 B2 | 4/2003 | Slayton et al. | | 600/439 |
| 6,544,179 B1 | 4/2003 | Schmiesing et al. | | 600/447 |
| 6,545,678 B1 | 4/2003 | Ohazama | | 345/427 |
| 6,551,246 B1 | 4/2003 | Ustuner et al. | | 600/447 |
| 6,565,512 B1 | 5/2003 | Ganguly et al. | | 600/449 |
| 6,569,097 B1 | 5/2003 | McMorrow et al. | | 600/437 |
| 6,569,101 B2 | 5/2003 | Quistgaard et al. | | 600/459 |
| 6,575,907 B1 | 6/2003 | Soferman et al. | | 600/438 |
| 6,585,647 B1 | 7/2003 | Winder | | 600/437 |
| 6,610,013 B1 | 8/2003 | Fenster et al. | | 600/439 |
| 6,611,141 B1 | 8/2003 | Schulz et al. | | 324/226 |
| 6,622,560 B2 | 9/2003 | Song et al. | | 73/606 |
| 6,628,743 B1 | 9/2003 | Drummond et al. | | 378/8 |
| 6,643,533 B2 | 11/2003 | Knoplioch et al. | | 600/407 |
| 6,650,927 B1 | 11/2003 | Keidar | | 600/424 |
| 6,676,605 B2 | 1/2004 | Barnard et al. | | 600/449 |
| 6,682,473 B1 | 1/2004 | Matsuura et al. | | 600/29 |
| 6,688,177 B2 | 2/2004 | Wiesauer | | 73/618 |
| 6,695,780 B1 | 2/2004 | Nahum et al. | | 600/437 |
| 6,705,993 B2 | 3/2004 | Ebbini et al. | | 600/443 |
| 6,716,175 B2 | 4/2004 | Geiser et al. | | 600/450 |
| 6,752,762 B1 | 6/2004 | DeJong et al. | | 600/458 |
| 6,755,787 B2 | 6/2004 | Hossack et al. | | 600/447 |
| 6,768,811 B2 | 7/2004 | Dinstein et al. | | 382/128 |
| 6,780,152 B2 | 8/2004 | Ustuner et al. | | 600/443 |
| 6,788,620 B2 | 9/2004 | Shiraishi et al. | | 367/152 |

| | | | |
|---|---|---|---|
| 6,801,643 B2 | 10/2004 | Pieper | 382/128 |
| 6,822,374 B1 | 11/2004 | Smith et al. | 310/334 |
| 6,825,838 B2 | 11/2004 | Smith et al. | 345/419 |
| 6,831,394 B2 | 12/2004 | Baumgartner et al. | 310/334 |
| 6,868,594 B2 | 3/2005 | Gururaja | 29/25.35 |
| 6,884,217 B2 | 4/2005 | McMorrow et al. | 600/443 |
| 6,903,813 B2 | 6/2005 | Jung et al. | 356/73 |
| 6,905,467 B2 * | 6/2005 | Bradley et al. | 600/443 |
| 6,905,468 B2 | 6/2005 | McMorrow et al. | 600/443 |
| 6,911,912 B2 | 6/2005 | Roe | 340/573.1 |
| 6,936,009 B2 | 8/2005 | Venkataramani et al. | 600/459 |
| 6,939,301 B2 | 9/2005 | Abdelhak | 600/437 |
| 6,951,540 B2 | 10/2005 | Ebbini et al. | 600/437 |
| 6,954,406 B2 | 10/2005 | Jones | 367/152 |
| 6,961,405 B2 | 11/2005 | Scherch | 378/65 |
| 6,962,566 B2 | 11/2005 | Quistgaard et al. | 600/437 |
| 6,970,091 B2 | 11/2005 | Roe | 340/573.1 |
| 7,004,904 B2 | 2/2006 | Chalana et al. | 600/443 |
| 7,025,725 B2 | 4/2006 | Dione et al. | 600/443 |
| 7,041,059 B2 | 5/2006 | Chalana et al. | 600/437 |
| 7,042,386 B2 | 5/2006 | Woodford et al. | 342/25 |
| 7,087,022 B2 | 8/2006 | Chalana et al. | 600/449 |
| 7,141,020 B2 | 11/2006 | Poland et al. | 600/447 |
| 7,142,905 B2 | 11/2006 | Slayton et al. | 600/427 |
| 7,177,677 B2 | 2/2007 | Kaula et al. | 600/546 |
| 7,189,205 B2 | 3/2007 | McMorrow et al. | 600/437 |
| 7,215,277 B2 | 5/2007 | Woodford et al. | 342/25 F |
| 7,255,678 B2 | 8/2007 | Mehi et al. | 600/446 |
| 7,301,636 B2 | 11/2007 | Jung et al. | 356/402 |
| 7,382,907 B2 | 6/2008 | Luo et al. | 382/128 |
| 7,450,746 B2 | 11/2008 | Yang et al. | 382/131 |
| 7,520,857 B2 | 4/2009 | Chalana et al. | 600/446 |
| 7,611,466 B2 | 11/2009 | Chalana et al. | 600/443 |
| 7,877,342 B2 * | 1/2011 | Buscema | 706/20 |
| 2001/0031920 A1 | 10/2001 | Kaufman et al. | 600/431 |
| 2001/0051771 A1 * | 12/2001 | Bradley et al. | 600/443 |
| 2002/0005071 A1 | 1/2002 | Song et al. | 73/606 |
| 2002/0009204 A1 * | 1/2002 | Matsumura | 381/98 |
| 2002/0016545 A1 | 2/2002 | Quistgaard et al. | 600/437 |
| 2002/0072671 A1 | 6/2002 | Chenal et al. | 600/450 |
| 2002/0102023 A1 | 8/2002 | Yamauchi et al. | 382/199 |
| 2002/0133075 A1 | 9/2002 | Abdelhak | 600/443 |
| 2002/0147399 A1 | 10/2002 | Mao et al. | 600/458 |
| 2002/0165448 A1 | 11/2002 | Ben-Haim et al. | 600/424 |
| 2003/0055336 A1 | 3/2003 | Buck et al. | 600/453 |
| 2003/0142587 A1 | 7/2003 | Zeitzew | 367/127 |
| 2003/0174872 A1 | 9/2003 | Chalana et al. | 382/128 |
| 2003/0181806 A1 | 9/2003 | Medan et al. | 600/411 |
| 2003/0216646 A1 | 11/2003 | Angelsen et al. | 600/437 |
| 2003/0229281 A1 | 12/2003 | Barnard et al. | 600/438 |
| 2004/0006266 A1 | 1/2004 | Ustuner et al. | 600/47 |
| 2004/0024302 A1 | 2/2004 | Chalana et al. | 600/407 |
| 2004/0034305 A1 | 2/2004 | Song et al. | 600/447 |
| 2004/0054280 A1 | 3/2004 | McMorrow et al. | 600/437 |
| 2004/0076317 A1 | 4/2004 | Roberts | 328/128 |
| 2004/0106869 A1 | 6/2004 | Tepper | 600/443 |
| 2004/0127796 A1 | 7/2004 | Chalana et al. | 600/449 |
| 2004/0127797 A1 | 7/2004 | Barnard et al. | 600/449 |
| 2004/0267123 A1 | 12/2004 | McMorrow et al. | |
| 2005/0135707 A1 | 6/2005 | Turek et al. | 382/294 |
| 2005/0174324 A1 | 8/2005 | Liberty et al. | 345/156 |
| 2005/0193645 A1 | 9/2005 | Sheljaskow et al. | 73/649 |
| 2005/0212757 A1 | 9/2005 | Marvit et al. | 345/156 |
| 2005/0215896 A1 | 9/2005 | McMorrow et al. | 600/437 |
| 2005/0228276 A1 | 10/2005 | He et al. | 600/437 |
| 2005/0240126 A1 | 10/2005 | Foley et al. | 601/2 |
| 2005/0253806 A1 | 11/2005 | Liberty et al. | 345/156 |
| 2006/0025689 A1 | 2/2006 | Chalana et al. | 600/456 |
| 2006/0064010 A1 | 3/2006 | Cannon, Jr. et al. | 600/434 |
| 2006/0078501 A1 | 4/2006 | Goertz et al. | 424/9.52 |
| 2006/0079775 A1 | 4/2006 | McMorrow et al. | 600/443 |
| 2006/0111633 A1 | 5/2006 | McMorrow et al. | 600/437 |
| 2006/0173312 A1 * | 8/2006 | Jackson et al. | 600/437 |
| 2006/0235301 A1 | 10/2006 | Chalana et al. | 600/443 |
| 2007/0004983 A1 | 1/2007 | Chalana et al. | 600/443 |
| 2007/0232908 A1 | 10/2007 | Wang et al. | 600/437 |
| 2007/0276247 A1 | 11/2007 | Chalana et al. | 600/447 |
| 2007/0276254 A1 | 11/2007 | Yang et al. | 600/463 |
| 2008/0139938 A1 | 6/2008 | Yang et al. | 600/445 |
| 2008/0146932 A1 | 6/2008 | Chalana et al. | 600/447 |
| 2008/0242985 A1 | 10/2008 | Chalana et al. | 600/443 |
| 2008/0249414 A1 | 10/2008 | Yang et al. | 600/445 |
| 2008/0262356 A1 | 10/2008 | Chalana et al. | 600/447 |
| 2009/0062644 A1 | 3/2009 | McMorrow et al. | 600/437 |
| 2009/0088660 A1 | 4/2009 | McMorrow et al. | 600/546 |
| 2009/0105585 A1 | 4/2009 | Wang et al. | 600/437 |
| 2009/0112089 A1 | 4/2009 | Barnard et al. | 600/443 |
| 2009/0264757 A1 | 10/2009 | Yang et al. | 600/443 |

FOREIGN PATENT DOCUMENTS

| | | |
|---|---|---|
| EP | 1 030 187 | 8/2000 |
| EP | 1 076 318 | 2/2001 |
| GB | 2 391 625 | 2/2004 |
| JP | 7-171149 | 7/1995 |
| JP | 2000-126178 | 5/2000 |
| JP | 2000-126181 | 5/2000 |
| JP | 2000-126182 | 5/2000 |
| JP | 2000-210286 | 8/2000 |
| WO | 01/35339 | 5/2001 |
| WO | 2009/032778 | 3/2009 |

OTHER PUBLICATIONS

Baker, A., et al., "Prediction of Non-Linear Propagation in Water Due to Diagnostic Medical Ultrasound Equipment", Phys. Med Biol., vol. 36, No. 11, pp. 1457-1464, 1991.

Barentsz et al., "Primary Staging of Urinary Bladder Carcinoma: the Role of MRI and a Comparison with CT," European Radiology vol. 6, pp. 129-133, 1996.

Besl, P., et al., "A Method for Registration of 3-D Shapes," IEEE Transaction on Pattern Analysis and Machine Intelligence, vol. 14, No. 2, pp. 239-256, Feb. 1992.

Birnholz, J., et al., "Amniotic Fluid Accumulation in the First Trimester," American Institute of Ultrasound in Medicine, Journal Ultrasound Medicine, vol. 14, pp. 597-602, 1995.

Bishop, S., et al., "Human Tissue-Temperature Rise During Ultrasound Treatments with the Aquaflex Gel Pad." Journal of Athletic Training, vol. 39, No. 2, pp. 126-131, 2004.

Bouakaz, A., et al., "Noninvasive Bladder Volume Measurements Based on Nonlinear Wave Distortion," Ultrasound in Medicine & Biology, vol. 30, No. 4, pp. 469-476, 2004.

Boyle, P., et al, "Prostate Volume Predicts Outcome of Treatment of Benign Prostatic Hyperplasia with Finasteride: Meta-Analysis of Randomized Clinical Trials," Urology, vol. 48, No. 3, pp. 398-405, 1996.

Cascione, C., et al., "Transabdominal Ultrasound Versus Excretory Urography in Preoperative Evaluation of Patients with Prostatism," The Journal of Urology, vol. 137, pp. 883-885, May 1987.

Chamberlain, P., "Amniotic Fluid Volume: Ultrasound Assessment and Clinical Significance," Seminars in Perinateology, vol. 9, No. 4, pp. 163-167, 1985.

Chamberlain, P. "Ultrasound Evaluation of Amniotic Fluid Volume," American Journal of Obstetrics and Gynaecology, vol. 150, No. 3, pp. 250-254, Oct. 1, 1984.

Cheng, X. et al., "Boundary Extraction Method for Three Dimensional Ultrasonic Echo Imaging Using Fuzzy Reasoning and Relaxation Techniques," IEEE, pp. 1610-1614, 1994.

Christensen, M., et al., "Clinical Manifestations of Benign Prostatic Hyperplasia and Indications for Therapeutic Intervention," Benign Prostatic Hyperplasia, Urologic Clinics of North America, vol. 17, No. 3, pp. 509-516, Aug. 1990.

Crowley, P., et al., "The Value of Ultrasound Measurement of Amniotic Fluid Volume in the Management of Prolonged Pregnancies," British Journal of Obstetrics and Gynaecology, vol. 91, pp. 444-448, May 1984.

Cvitkovic-Kuzmic, A., et al., "Sonographic Measurement of Detrusor Muscle Thickness in Healthy Children," Pedatric Nephrology, vol. 16, pp. 1122-1125, 2001.

Cvitkovic-Kuzmic, A., et al., "Ultrasound Assessment of Detrusor Muscle Thickness in Children with Non-Neuropathic Bladder/ Sphincter Dysfunction," European Urology, Vo. 41, pp. 214-219, 2002.

Elliott, P., "Interactive Image Segmentation for Radiation Treatment Planning," IBM Systems Journal, vol. 31, No. 4, pp. 620-634, 1992.

Forbes, F., et al., "Bayesian Morphology: Fast Unsupervised Bayesian Image Analysis," Journal of the American Statistical Association, vol. 94, No. 446, pp. 555-568, Jun. 1999.

Gerald, C., et al., "Applied Numerical Analysis," Fifth Edition, Addison-Wesley Publishing Company, Chapter 3, 'Interplation and Curve Fitting,', pp. 210-287.

Gobbi, D., et al. "Real-Time 3D Ultrasound for Intraoperative Surgical Guidance," 8 pgs.

Gramellini, D., et al., "Sonographic Assessment of Amniotic Fluid Volume Between 11 and 24 Weeks of Gestation: Construction of Reference Intervals Related to Gestational Age," Ultrasound Obstetrics Gynaecology, vol. 17, pp. 410-415, 2001.

Grover, J., et al., "Three-Dimensional Method for Determination of Amniotic Fluid Volume in Intrauterine Pockets," vol. 90, No. 6, pp. 1007-1010, Dec. 1997.

Hakenberg, O., et al., "Bladder Wall Thickness in Normal Adults and Men with Mild Lower Urinary Tract Symptoms and Benign Prostatic Enlargement," Neurourology and Urodynamics, vol. 19, pp. 585-593, 2000.

Hakenberg, O., et al., "The Estimation of Bladder Volume by Sonocystrography," Journal of Urology, vol. 130, No. 2, pp. 249-251, Aug. 1983.

Holmes, J., et al., "Ultrasonic Studies of the Bladder," The Journal of Urology, vol. 91, pp. 654-663, 1967.

Jeng, C., et al., "Amniotic Fluid Index Measurement with the Four-Quadrant Technique During Pregnancy," The Journal of Reproductive Medicine, Inc., vol. 35, No. 7, pp. 674-677, Jul. 1990.

Jequier, S., et al., "Sonographic Measurements of the Normal Bladder Wall in Children," AJR, vol. 149, pp. 563-566, Sep. 1987.

Jong, et al., "Ultrasound Contrast Agents" ISBN 1-85317-858-4 chapter 3 "Contrast-Specific Imaging Methods".

Khullar, V., et al. "A Novel Technique for Measuring Bladder Wall Thickness in Women Using Transvaginal Ultrasound,"Ultrasound Obestetrics and Gyneacology, vol. 4, pp. 220-223, 1994.

Khullar, V., et al., "Ultrasound: a Noninvasive Screening Test for Detrusor Instability," British Journal of Obstetrics and Gynaecology, vol. 103, pp. 904-908, Sep. 1996.

Kojima, M., et al., "Reversible Change of Bladder Hypertrophy Due to Benign Prostatic Hyperplasia After Surgical Relief of Obstruction," The Journal of Urology, vol. 158, pp. 89-93, Jul. 1997.

Kojima, M., et al., "Ultrasonic Estimation of Bladder Weight as a Measure of Bladder Hypertrophy in Men with Infravesical Obstruction: a Preliminary Report," Urology, vol. 47, No. 6, pp. 942-947, 1996.

Krenning, B., et al., "Assessment of Left Ventricular Function by Three-Dimensional Echocardiography," Cardiovascular Ultrasound, 7 pgs., 2003.

Kruczkowski et al., "A Non-Invasive Ultrasonic System to Determine Residual Bladder Volumes", IEEE Engineering in Medicine Biology Society 10th Ann Conf, pp. 1623-1624.

Lea, J., et al., "Registration and Immobilization in Robot-Assisted Surgery," Computer Aided Surgery, vol. 1, No. 2, pp. 80-87, 1995.

Lorensen, W., et al., "Marching Cubes: A High Resolution 3D Surface Construction Algorithm," ACM Siggraph Computer Graphics, vol. 21, No. 4, pp. 163-169, Jul. 1987.

Madsen, F., et al., "Clinical Manifestations of Benign Prostatic Hyperplasia," Advances in Benign Prostatic Hyperplasia, Urologic Clinics of North America, vol. 22, No. 2, pp. 291-298, May 1995.

Magann, E., et al., "Amniotic Fluid Volume Determination," American Journal of Obstetrics and Gynaecology, Vo. 169, No. 2, Part 1, pp. 435-437, 1999.

Magann, E., et al., "Measurement of Amniotic Fluid Volume: Accuracy of Ultrasonography Techniques," American Journal of Obstetrics and Gynaecology, vol. 167, No. 6, pp. 1533-1537, 1992.

Magann, E., et al., "Ultrasound Estimate of Amniotic Fluid Volume: Color Doppler Overdiagnosis of Oligohydramnios," Obstetrics & Gynecology, vol. 98, No. 1, pp. 71-74, Jul. 2001.

Magann, E., et al., "Ultrasound Estamation of Amniotic Fluid Volume Using the Largest Vertical Pocket Containing Umbilical Cord: Measure to or Through the Cord," Ultrasound Obstetrics and Gynecology, vol. 20, pp. 464-467, 2002.

Manieri, C., et al., "The Diagnosis of Bladder Outlet Obstruction in Men by Ultrasound Measurement of Bladder Wall Thickness," The Journal of Urology, vol. 159, 761-765, pp. 761-765, Mar. 1998.

Mann, S., et al., "Novel Technique for Assessing Amniotic Fluid Volume: use of a Three-Dimensional Bladder Scanner," The Journal of Maternal-Fetal Medicine, vol. 9, pp. 308-310, 2000.

Manning, F., et al., "Qualitative Amniotic Fluid Volume Determination by Ultrasound: Antepartum Detection of Intrauterine Growth Retardation," American Journal of Obstetrics and Gynecology, vol. 139, No. 3, pp. 254-258, Feb. 1, 1981.

Martan, A., et al., "Ultrasound Imaging of the Lower Urinary System in Women after Burch Colposuspension," Ultrasound Obstetrics and Gynecology, vol. 17, pp. 58-64, 2001.

Matthews, P. et al., "The Use of Ultrasound in the Investigation of Prostatism," British Journal of Urology, vol. 54, pp. 536-538, 1982.

Merks, E. et al., "Design of a Multilayer Transducer for Acoustic Bladder Volume Assessment," IEEE Transacations on Ultrasonics, Ferroelectrics and Frequency Control, vol. 53, No. 10, pp. 1730-1738, Oct. 2006.

Merks, E., et al., "A KLM-Circuit Model of a Multi-Layer Transducer for Acoustic Bladder Volume Measurements," Ultrasonics, vol. 44, pp. 705-710, Dec. 22, 2006.

Miyashita, H., et al., "Ultrasonic Measurement of Bladder Weight as a Possible Predictor of Acute Urinary Retention in Men with Lower Urinary Tract Symptoms Suggestive of Benign Prostatic Hyperplasia," Ultrasound in Medicine & Biology, vol. 28, No. 8, pp. 985-990, 2002.

Moore, T., "Superiority of the Four-Quadrant Sum Over the Single-Deepest-Pocket Technique in Ultrasonographic Identification of Abnormal Amniotic Fluid Volumes," American Journal of Obstetrics and Gynecology, vol. 163, No. 5, pp. 762-767, 1990.

Muller, L., et al., "Detrusor Thickness in Healthy Children Assessed by a Standardized Ultrasound Method," The Journal of Urology, vol. 166, pp. 2364-2367, Dec. 2001.

Muller, L., et al., "Standardized Ultrasound Method for Assessing Detrusor Muscle Thickness in Children," The Journal of Urology, vol. 164, pp. 134-138, Jul. 2000.

Myles, T., et al., "Four-Quadrant Assessment of Amniotic Fluid Volume: Distribution's Role in Predicting Fetal Outcome," Journal of Obstetrics and Gynecology, vol. 80, No. 5, pp. 769-774, Nov. 1992.

Naya, Y., et al., "Intraobserver and Interobserver Variance in the Measurement of Ultrasound-Estimated Bladder Weight," Ultrasound in Medicine and Biology, vol. 24, No. 5, pp. 771-773, 1998.

Oelke, M., et al., "Increase in Detrusor Wall Thickness Indicates Bladder Outlet Obstruction (BOO) in Men," World Journal of Urology, vol. 19, pp. 443-452, 2002.

Ohashit, G., et al., "Boundary Estimation for Ultrasonic 3-D Imaging," SPIE vol. 1898 Image Processing, pp. 480-486, 1993.

Oomen, JA, et al., "Towards Assessment of Regional Wall Stress of the Left Ventricle Using 3D Ultrasound Imaging," IEEE Computers in Cardiology, vol. 26, pp. 129-132, 1999.

Phelan, J., et al., Amniotic Fluid Volume Assessment with the Four-Quadrant Technique at 36-42 Weeks' Gestation, The Journal of Reproductive Medicine, vol. 32, No. 7, pp. 540-542, Jul. 1987.

Rutherford, S., et al., "The Four-Quadrant Assessment of Amniotic Fluid Volume: An Adjunct to Antepartum Fetal Heart Rate Testing," Journal of Obstetrics and Gynecology, vol. 70, No. 3, Part 1, pp. 353-356, Sep. 1987.

Sagiv, C., et al., "Application of a Semiautomatic Boundary Detection Algorithm for the Assessment of Amniotic Fluid Quantity Form Ultrasound Images," Ultrasound in Medicine and Biology, vol. 25, No. 4, pp. 515-526, 1999.

Sahin, B., et al., "Estimation of the Amniotic Fluid Volume Using the Cavalieri Method on Ultrasound Images," International Journal of Gynecology and Obstetrics, vol. 82, pp. 25-30, 2003.

Santilli, J., et al., "Diagnosis and Treatment of Abdominal Aortic Aneurysms," American Family Physician, vol. 56, No. 4, pp. 1081-1090, Sep. 1997.

Scheinerman, E., "Invitation to Dynamical Systems," Chapter 5, 'Fractals,' Prentice Hall pp. 231-315, 1996.

Schiff, E., et al., "Standardized Measurement of Amniotic Fluid Volume by Correlation of Sonography with Dye Dilution Technique," Obestetrics and Gynecology, vol. 76, No. 1, pp. 44-46, Jul. 1990.

Schrimmer, D., et al., "Sonographic Evaluation of Amniotic Fluid Volume," Clinical Obstetrics and Gynecology, vol. 45, No. 4, pp. 1026-1029, 2002.

Sepulveda W., et al., "Direct Volume Measurement at Midtrimester Amnioinfusion in Relation to Ultrasonographic Indexes of Amniotic Fluid Volume," American Journal of Obstetrics and Gynecology, vol. 170, No. 4, pp. 1160-1163, Apr. 1994.

Shiota, T., et al., "Real-time Three-Dimensional Echocardiography for Determining Right Ventricular Stroke Volume in an Animal Model of Chronic Right Ventricular Volume Overload," Circulation Journal of the American Heart Association, vol. 97, pp. 1897-1900, 1998.

Stangenberg, M., et al., "Amniotic Fluid Volumes in Pregnant Diabetics During the Last Trimester," Acta Obstetrics Gynecology Scand, vol. 61, pp. 313-316, 1982.

Szabo, T., et al., "Effects of Nonlinearity on the Estimation of In Situ Values of Acoustic Output Parameters," Journal of Ultrasound in Medicine, American Institute of of Ultrasound in Medicine, vol. 18, No. 1, pp. 33-41, 1999.

Weissman, A., et al., "Sonographic Measurement of Amniotic Fluid Volume in the First Trimester of Pregnancy," American Institute of Ultrasound in Medicine, vol. 15, pp. 771-774, 1996.

Hamilton; Nonlinear Acoustics; 1998; pp. 65-150. Please see pp. 132-133 regarding the use of Goldberg numbers; Academic Press; San Diego, CA USA.

* cited by examiner

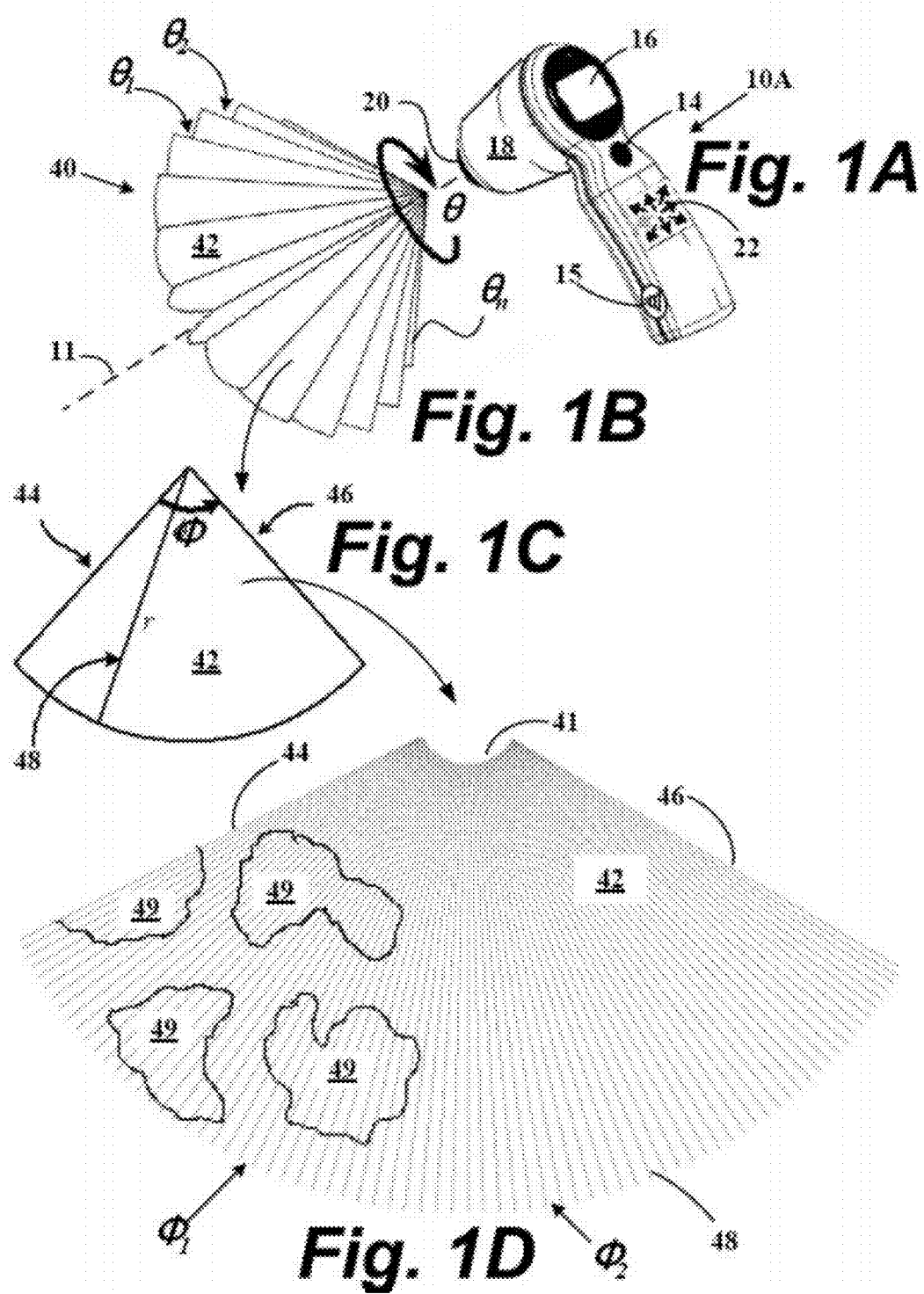

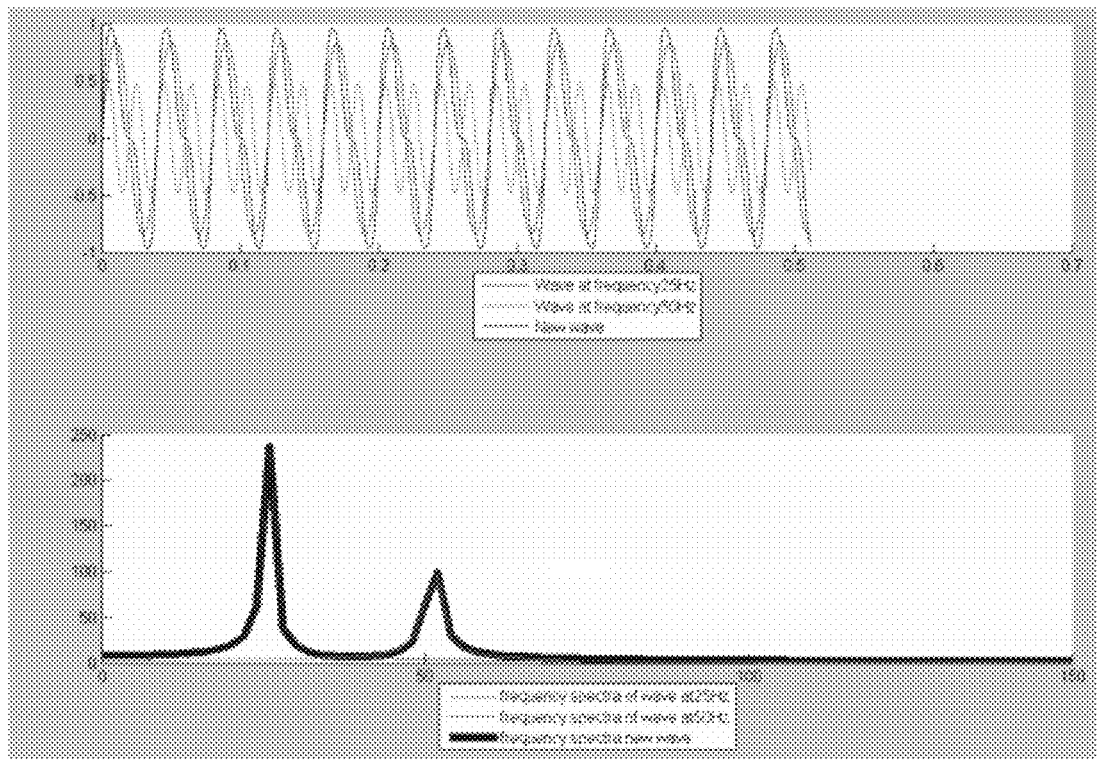
Progressive Sound Wave Distortion with Increasing Harmonics
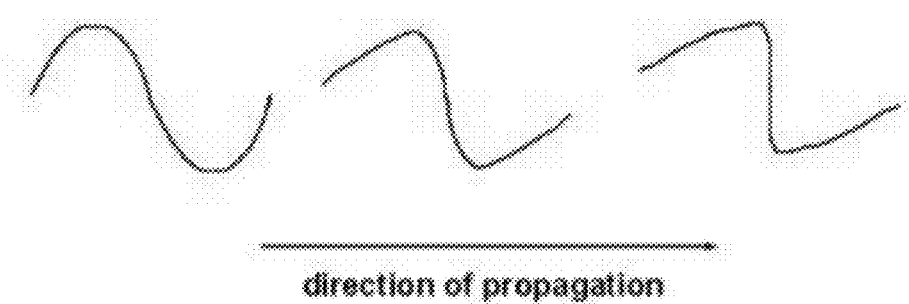
direction of propagation
*Fig. 10*

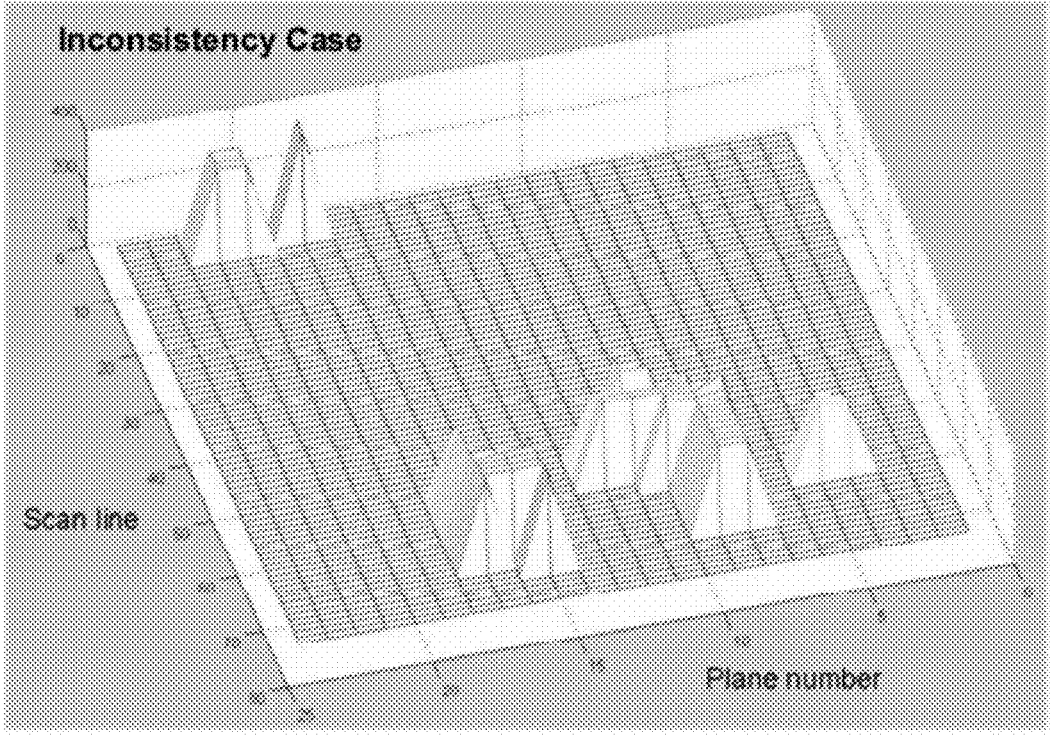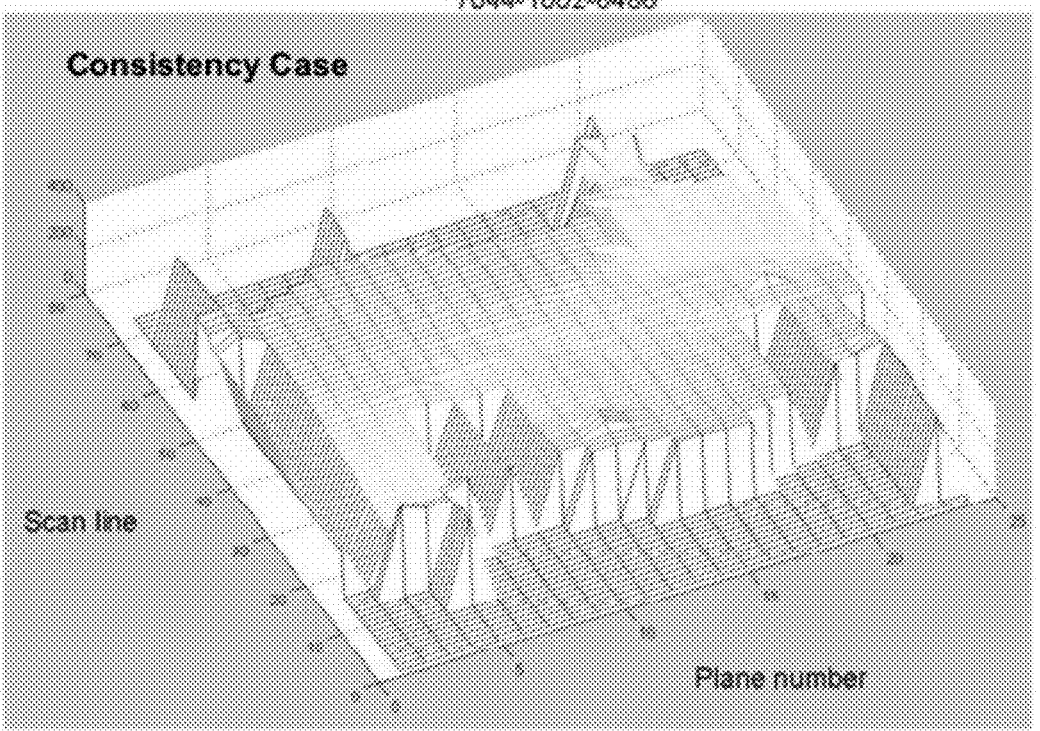
Fig. 25

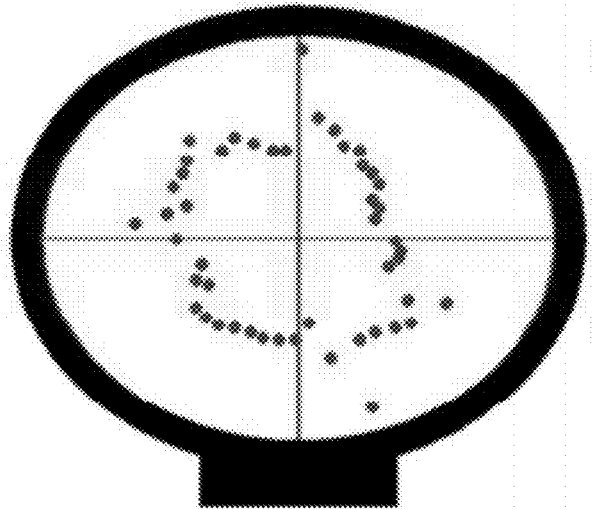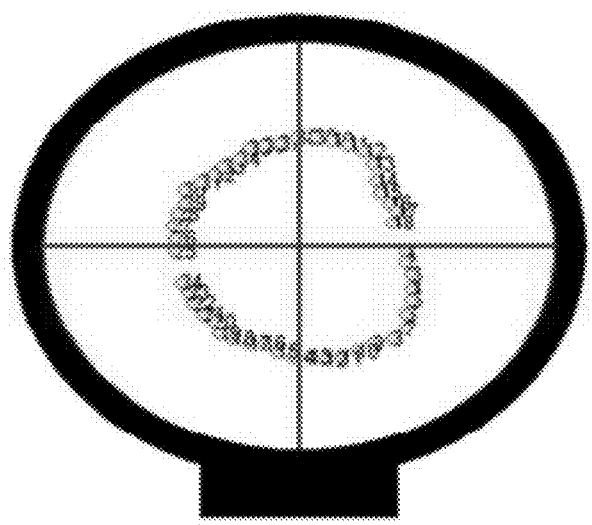
Fig. 26

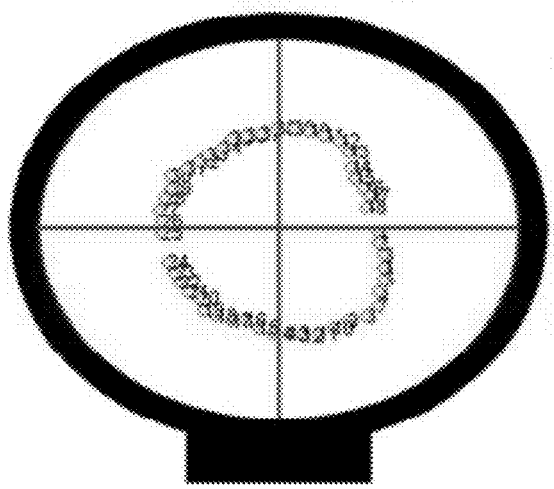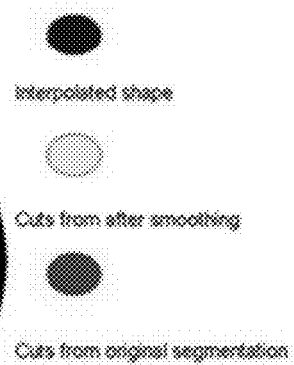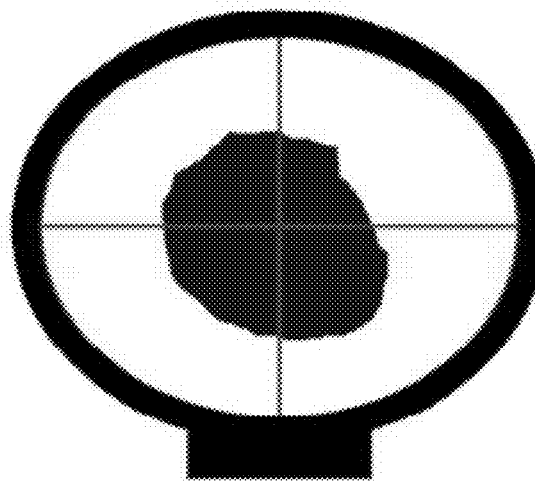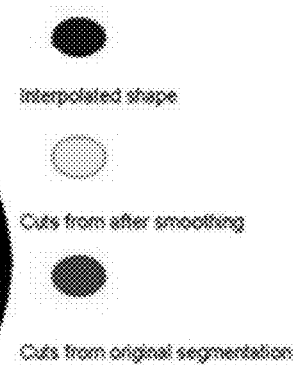
Fig. 27

Different arrow feedback modes

Shadow, segmentation and pubic bone

Example of grading results

A series of intermediate C-mode shapes

SYSTEM AND METHOD FOR BLADDER DETECTION USING HARMONIC IMAGING

CROSS REFERENCE TO RELATED APPLICATIONS

This application is a continuation-in-part of, claims priority to, and incorporates by reference in its entirety to U.S. patent application Ser. No. 11/968,027 filed Dec. 31, 2007.

This application is a continuation-in-part of, claims priority to, and incorporates by reference in its entirety to U.S. patent application Ser. No. 11/926,522 filed Oct. 29, 2007 now abandoned.

This application is a continuation-in-part of, claims priority to, and incorporates by reference in its entirety to U.S. patent application Ser. No. 11/925,887 filed Oct. 27, 2007 now abandoned.

This application is a continuation-in-part of, claims priority to, and incorporates by reference in its entirety to U.S. patent application Ser. No. 11/925,896 filed Oct. 27, 2007 now abandoned.

This application is a continuation-in-part of, claims priority to, and incorporates by reference in its entirety to U.S. patent application Ser. No. 11/925,900 filed Oct. 27, 2007 now abandoned.

This application is a continuation-in-part of, claims priority to, and incorporates by reference in its entirety to U.S. patent application Ser. No. 11/925,850 filed Oct. 27, 2007.

This application is a continuation-in-part of, claims priority to, and incorporates by reference in its entirety to U.S. patent application Ser. No. 11/925,843 filed Oct. 27, 2007 now abandoned.

This application is a continuation-in-part of, claims priority to, and incorporates by reference in its entirety to U.S. patent application Ser. No. 11/925,654 filed Oct. 26, 2007 now abandoned.

This application incorporates by reference in their entirety and claims priority to U.S. Provisional Patent Application Nos. 60/938,359 filed May 16, 2007; 60/938,371 filed May 16, 2007; and 60/938,446 filed May 16, 2007.

All applications incorporated by reference in their entirety.

COPYRIGHT NOTICE

This Disclosure is Protected Under United States and International Copyright Laws. © Verathon® Incorporated. all Rights Reserved. A Portion of the Disclosure of this Patent Document Contains Material which is Subject to Copyright Protection. the Copyright Owner has No Objection to the Facsimile Reproduction by Anyone of the Patent Document or the Patent Disclosure, as it Appears in the Patent and Trademark Office Patent File or Records, but Otherwise Reserves all Copyright Rights Whatsoever.

FIELD OF THE INVENTION

Embodiments of the invention pertain to organ imaging using ultrasonic harmonics.

BACKGROUND OF THE INVENTION

It has been shown that ultrasonic waves traveling through different mediums undergo harmonic distortion. The various attributes of these mediums determine what type of harmonic distortion is dominant when an ultrasonic wave passes through the medium. Ultrasound imaging depending on Fast Fourier Transforms (FFT) and other algorithms may lack the needed spectral information to generate diagnostically useful images. The deficiency inherent in these algorithms can be overcome by using other approaches.

SUMMARY OF THE PARTICULAR EMBODIMENTS

Systems, methods, and ultrasound transceivers equipped to probe structures and cavity filed organs with fundamental and/or harmonic ultrasound energies under A-mode, B-mode, and C-mode configurations. Systems and methods provide for implementing and executing harmonic analysis of ultrasound frequencies and extract harmonic information related to a targeted organ of a subject are described. The methods utilize neural network algorithms to establish improved segmentation accuracy of the targeted organ or structures within a region-of-interest. The neural network algorithms refined for detection of the bladder and to ascertain the presence or absence of a uterus, is optimally applied to better segment and thus confer the capability to optimize measurement of bladder geometry, area, and volumes.

BRIEF DESCRIPTION OF THE DRAWINGS

FIGS. 1A-D depicts a partial schematic and a partial isometric view of a transceiver, a scan cone comprising a rotational array of scan planes, and a scan plane of the array of an ultrasound harmonic imaging system;

FIG. 10 schematically illustrates sound wave distortion with increasing harmonics;

FIG. 25 presents a 3-D plot of an inconsistency case (upper plot) and a consistency case (lower plot) as a means to check the consistency of the segmentation results;

FIG. 26 illustrates interpolated shapes before smoothing (top diagram) and after smoothing based on the mass center (bottom diagram);

FIG. 27 illustrates the output of interpolated shapes between smoothed cuts before smoothing without interpolation;

DETAILED DESCRIPTION OF THE PARTICULAR EMBODIMENTS

Figure 2A:
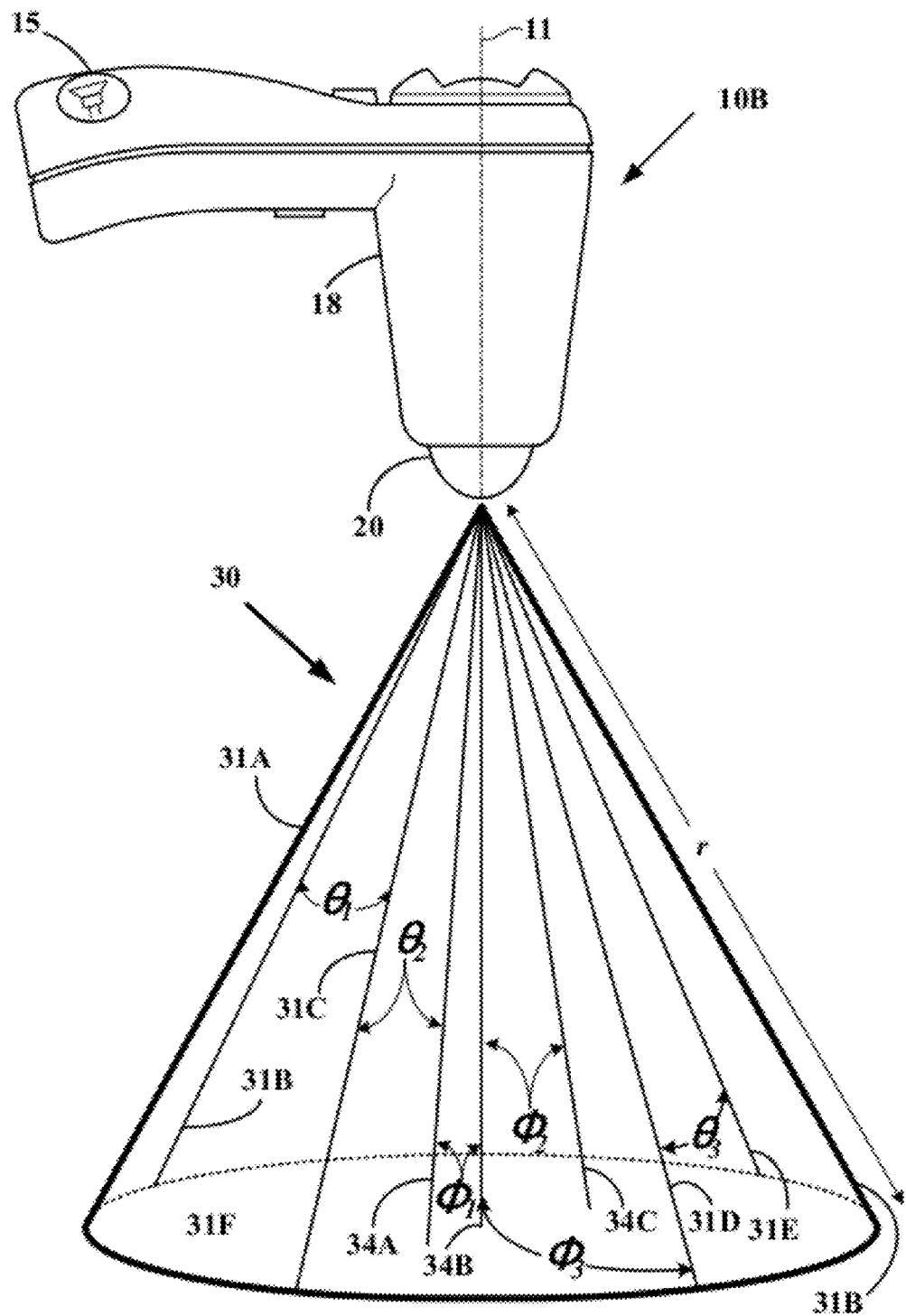
FIG. 2A depicts a partial schematic and partial isometric and side view of a transceiver, and a scan cone array comprised of 3D-distributed scan lines in alternate embodiment of an ultrasound harmonic imaging system.

Systems and methods described that encompass ultrasound detection and measurement of cavity containing organs that are amendable to detection and measurement employing fundamental ultrasound and harmonics of ultrasound frequencies analysis. Ultrasound transceivers equipped with deliver and receive fundamental ultrasound energies utilize different signal processing algorithms than ultrasound transceivers equipped to probe cavity-containing organs with ultrasound harmonic energies. Algorithms described below are developed to optimally extract organ information from fundamental and/or harmonic ultrasound echoes delivered under A-mode, B-mode, and/or C-mode methodologies. Alternate embodiments of the algorithms may be adapted to detect bladders in males, females that have not undergone hysterectomy procedures, females that have undergone hysterectomy procedures, and small male and female children.

Ultrasound transceivers equipped for utilizing ultrasound harmonic frequencies employ a neural network algorithm. The neural network algorithm is defined in computer executable instructions and employs artificial intelligence to echogenic signals delivered from ultrasound transceivers equipped with ultrasound harmonic functionality. The neural network algorithm uses returning first and second echo wavelength harmonics that arise from differential and non-linear wavelength distortion and attenuation experienced by transiting ultrasound energy returning from a targeted region-of-interest (ROI). Using the harmonic ratios with the sub-aperture algorithm provides diagnostically useful information of the media though which ultrasound passes. The 9400 transducer described below has been redesigned to allow extraction of useful ultrasound information that distinguishes different mediums through which the ultrasound energy traverses. The sub-aperture algorithms are substantially fast enough to be implemented in real time within the time constraints enforced by ultrasound scanning protocols to acquire organ size information besides the original ultrasound B-mode image. The harmonic information is collected using a long interrogating pulse with a single fundamental frequency. The received signal is collected, analyzed for its spectrum information about the first and second harmonics. The ratio of these two harmonics provides the quantitative information on how much harmonics have been generated and attenuated along its propagation. The neural network sub-aperture algorithm is executed in non-parametric mode to minimize data modeling errors.

Disclosure below includes systems and method to detect and measure an organ cavity involving transmitting ultrasound energy having at least one of a fundamental and harmonic frequency to the organ cavity, collecting ultrasound echoes returning from the organ cavity and generating signals from the ultrasound echoes, and identifying within the ultrasound signals those attributable to fundamental ultrasound frequencies or those attributable to harmonic ultrasound frequencies. Thereafter, the fundamental frequency derived signals and the harmonic frequency derived signals undergo signal processing via computer executable program instructions to present an image of the organ on a display and/or its organ cavity, and calculating the volume of the organ and/or its organ cavity. The signal processing applied to the transceiver echoic fundamental and harmonic ultrasound signals include a neural network algorithm having computer readable instructions for ascertaining the certainty that a given scan line traverses a given organ's cavity region, a non-cavity region, or both a cavity and a non-cavity region using a grading algorithm for predicting the scan line's cavity or non-cavity classification. The organs include, for example, the internal void of a bladder, the void of a uterus, or the ventricular and atrial chambers of a heart. The grading algorithm includes weighting the contributions of at least one of an ultrasound harmonic ration, an organ's tissue difference or delta that is proportional to the attenuation that a given ultrasound fundamental and/or harmonic frequency experiences transiting through the tissue, a minRsum value, a cavity front wall location, and a cavity back wall location.

Using harmonic information to distinguish different scan lines are based on the harmonic model we built. The model is set up based on a series of water tank experiments by using simulated body fluids, simulated body tissue, and combination simulated body fluids and body tissues for transducers having the characteristics of a 13 mm, 2.949 MHz transducer in an ultrasound transceiver developed by Verathon®, Inc. These tests prove that it is feasible to distinguish different kinds of scan lines. In general the larger the harmonic ratio, the larger the possibility that the scan line is passing through water region; the harmonic ratio is increasing linearly based upon the water region size.

The ultrasound transceivers or DCD devices developed by Verathon®, Inc are capable of collecting in vivo three-dimensional (3-D) cone-shaped ultrasound images of a patient. Based on these 3-D ultrasound images, various applications have been developed such as bladder volume and mass estimation. The clarity of images from the DCD ultrasound transceivers depends significantly upon the functionality, precision, and performance accuracy of the transducers used in the DCD ultrasound transceivers.

During the data collection process initiated by DCD, a pulsed ultrasound field is transmitted into the body, and the back-scattered "echoes" are detected as a one-dimensional (1-D) voltage trace, which is also referred to as a RF line. After envelope detection, a set of 1-D data samples is interpolated to form a two-dimensional (2-D) or 3-D ultrasound image.

FIGS. 1A-D depicts a partial schematic and a partial isometric view of a transceiver, a scan cone comprising a rotational array of scan planes, and a scan plane of the array of various ultrasound systems 60A-D capable of collecting RF line and employing harmonic analysis.

FIG. 1A is a side elevation view of an ultrasound transceiver 10A that includes an inertial reference unit, according to an embodiment of the invention. The transceiver 10A includes a transceiver housing 18 having an outwardly extending handle 12 suitably configured to allow a user to manipulate the transceiver 10A relative to a patient. Ultrasound transducers operating within the transceiver 10A may be equipped to collect and ready signals for ultrasound fundamental and/or harmonic frequency analysis.

The handle 12 includes a trigger 14 that allows the user to initiate an ultrasound scan of a selected anatomical portion, and a cavity selector (not shown). The transceiver 10A also includes a transceiver dome 20 that contacts a surface portion of the patient when the selected anatomical portion is scanned. The dome 20 generally provides an appropriate acoustical impedance match to the anatomical portion and/or permits ultrasound energy to be properly focused as it is projected into the anatomical portion. The transceiver 10A further includes one, or preferably an array of separately excitable ultrasound transducer elements (not shown in FIG. 1A) positioned within or otherwise adjacent with the housing 18. The transducer elements may be suitably positioned within the housing 18 or otherwise to project ultrasound energy outwardly from the dome 20, and to permit reception of acoustic reflections generated by internal structures within the anatomical portion. The one or more array of ultrasound elements may include a one-dimensional, or a two-dimensional array of piezoelectric elements that may be moved within the housing 18 by a motor. Alternately, the array may be stationary with respect to the housing 18 so that the selected anatomical region may be scanned by selectively energizing the elements in the array.

A directional indicator panel or aiming guide panel 22 includes a plurality of arrows that may be illuminated for initial targeting and guiding a user to access the targeting of an organ or structure within an ROI. In the 9400 system described in FIG. 2C below, the directional indicator panel 22 has a virtual equivalent in the form of a targeting icon screenshot 77B, both indicator panel 22 and targeting icon 77B functioning to guide a transceiver user to place the transceiver to obtain a centered bladder or other cavity-containing organ. In particular embodiments if the organ or structure is centered from placement of the transceiver 10A acoustically placed against the dermal surface at a first location of the subject, the directional arrows may be not illuminated. If the organ is off-center, an arrow or set of arrows may be illuminated to direct the user to reposition the transceiver 10A acoustically at a second or subsequent dermal location of the subject. The acrostic coupling may be achieved by liquid sonic gel applied to the skin of the patient or by sonic gel pads to which the transceiver dome 20 is placed against. The directional indicator panel 22 may be presented on the display 54 of computer 52 in harmonic imaging subsystems described in FIGS. 3 and 4 below, or alternatively, presented on the transceiver display 16.

Transceiver 10A may include an inertial reference unit that includes an accelerometer 22 and/or gyroscope 23 positioned preferably within or adjacent to housing 18. The accelerometer 22 may be operable to sense an acceleration of the transceiver 10A, preferably relative to a coordinate system, while the gyroscope 23 may be operable to sense an angular velocity of the transceiver 10A relative to the same or another coordinate system. Accordingly, the gyroscope 23 may be of conventional configuration that employs dynamic elements, or it may be an optoelectronic device, such as the known optical ring gyroscope. In one embodiment, the accelerometer 22 and the gyroscope 23 may include a commonly packaged and/or solid-state device. One suitable commonly packaged device may be the MT6 miniature inertial measurement unit, available from Omni Instruments, Incorporated, although other suitable alternatives exist. In other embodiments, the accelerometer 22 and/or the gyroscope 23 may include commonly packaged micro-electromechanical system (MEMS) devices, which are commercially available from MEMSense, Incorporated. As described in greater detail below, the accelerometer 22 and the gyroscope 23 cooperatively permit the determination of positional and/or angular changes relative to a known position that is proximate to an anatomical region of interest in the patient. Other configurations related to the accelerometer 22 and gyroscope 23 concerning transceivers 10A,B equipped with inertial reference units and the operations thereto may be obtained from copending U.S. patent application Ser. No. 11/222,360 filed Sep. 8, 2005, herein incorporated by reference.

The transceiver 10A includes (or if capable at being in signal communication with) a display 16 operable to view processed results from an ultrasound scan, and/or to allow an operational interaction between the user and the transceiver 10A. For example, the display 24 may be configured to display alphanumeric data that indicates a proper and/or an optimal position of the transceiver 10A relative to the selected anatomical portion. Display 16 may be used to view two- or three-dimensional images of the selected anatomical region. Accordingly, the display 16 may be a liquid crystal display (LCD), a light emitting diode (LED) display, a cathode ray tube (CRT) display, or other suitable display devices operable to present alphanumeric data and/or graphical images to a user.

Still referring to FIG. 1A, the cavity selector (not shown) includes a pressable button similar to the trigger 14 may be operable to adjustably adapt the transmission and reception of ultrasound signals to the anatomy of a selected patient. In particular, the cavity selector adapts the transceiver 10A to accommodate various anatomical details of male and female patients. For example, when the cavity selector is adjusted to accommodate a male patient, the transceiver 10A may be suitably configured to locate a single cavity, such as a urinary bladder in the male patient. In contrast, when the cavity selector is adjusted to accommodate a female patient, the transceiver 10A may be configured to image an anatomical portion having multiple cavities, such as a bodily region that includes a bladder and a uterus. Alternate embodiments of the transceiver 10A may include a cavity selector configured to select a single cavity scanning mode, or a multiple cavity-scanning mode that may be used with male and/or female patients. The cavity selector may thus permit a single cavity region to be imaged, or a multiple cavity region, such as a region that includes a lung and a heart to be imaged.

To scan a selected anatomical portion of a patient, the transceiver dome 20 of the transceiver 10A may be positioned against a surface portion of a patient that is proximate to the anatomical portion to be scanned. The user actuates the transceiver 10A by depressing the trigger 14. In response, the transceiver 10 transmits ultrasound signals into the body, and receives corresponding return echo signals that may be at least partially processed by the transceiver 10A to generate an ultrasound image of the selected anatomical portion. In a particular embodiment, the transceiver 10A transmits ultrasound signals in a range that extends from approximately about two megahertz (MHz) to approximately about ten MHz. Ultrasound energies beyond 10 MHz may be utilized.

Figure 3:
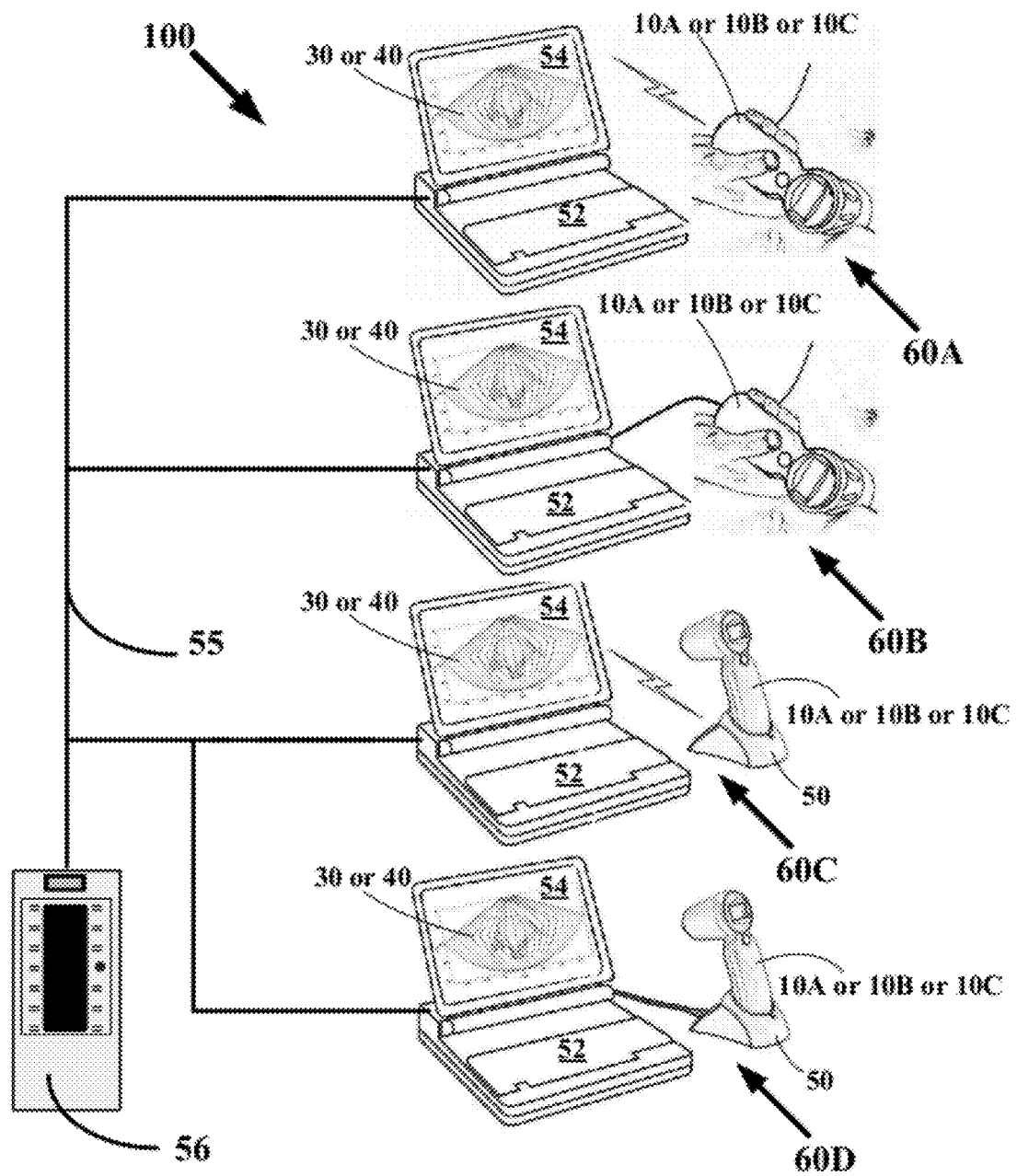
FIG. 3 is a schematic illustration of a server-accessed local area network in communication with a plurality of ultrasound harmonic imaging systems.
Figure 4:
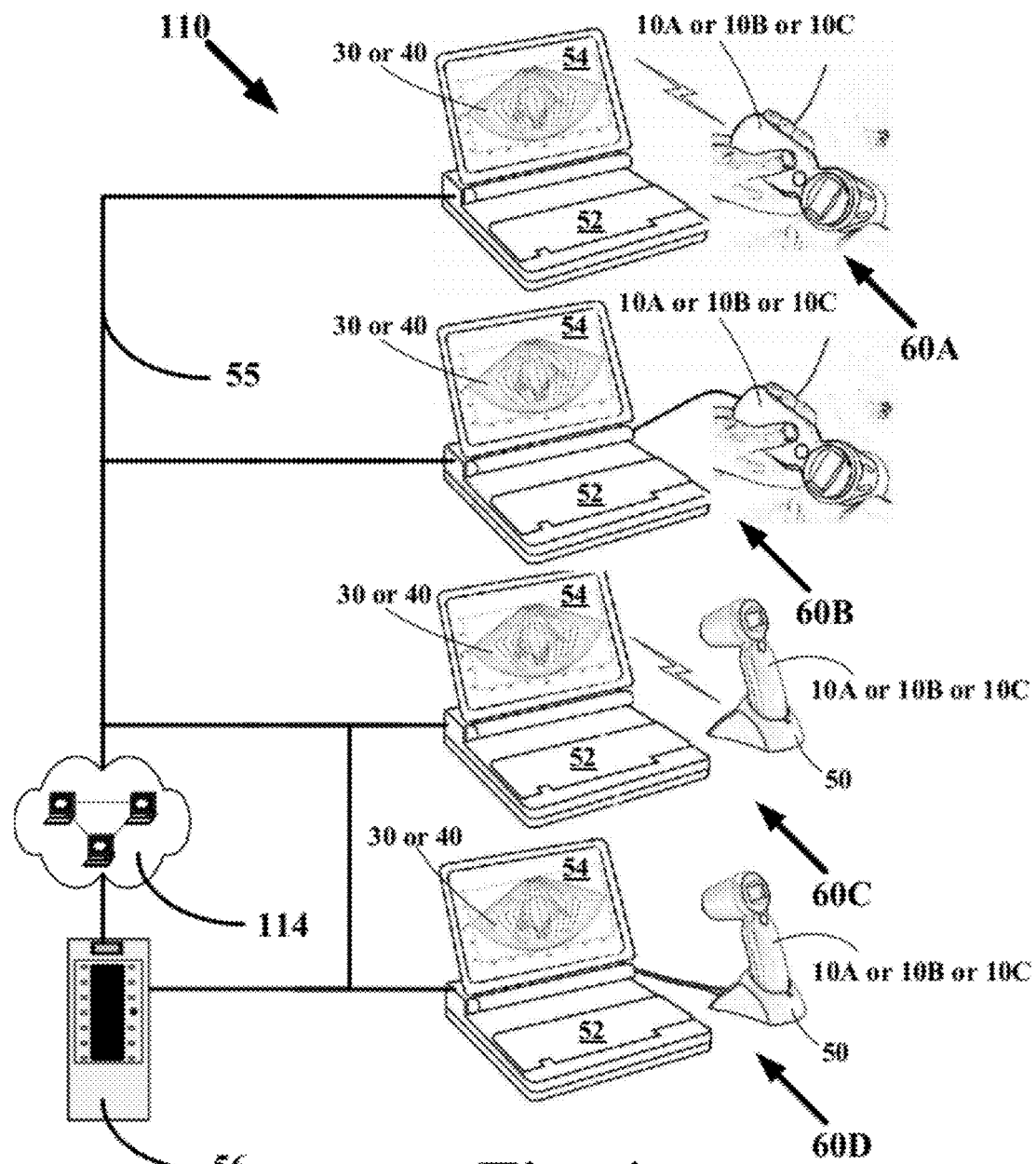
FIG. 4 is a schematic illustration of the Internet in communication with a plurality of ultrasound harmonic imaging systems.

In one embodiment, the transceiver 10A may be operably coupled to an ultrasound system that may be configured to generate ultrasound energy at a predetermined frequency and/or pulse repetition rate and to transfer the ultrasound energy to the transceiver 10A. The system also includes a processor that may be configured to process reflected ultrasound energy that is received by the transceiver 10A to produce an image of the scanned anatomical region. Accordingly, the system generally includes a viewing device, such as a cathode ray tube (CRT), a liquid crystal display (LCD), a plasma display device, or other similar display devices, that may be used to view the generated image. The system may also include one or more peripheral devices that cooperatively assist the processor to control the operation of the transceiver 10A, such a keyboard, a pointing device, or other similar devices. In still another particular embodiment, the transceiver 10A may be a self-contained device that includes a microprocessor positioned within the housing 18 and software associated with the microprocessor to operably control the transceiver 10A, and to process the reflected ultrasound energy to generate the ultrasound image. Accordingly, the display 16 may be used to display the generated image and/or to view other information associated with the operation of the transceiver 10A. For example, the information may include alphanumeric data that indicates a preferred position of the transceiver 10A prior to performing a series of scans. In yet another particular embodiment, the transceiver 10A may be operably coupled to a general-purpose computer, such as a laptop or a desktop computer that includes software that at least partially controls the operation of the transceiver 10A, and also includes software to process information transferred from the transceiver 10A, so that an image of the scanned anatomical region may be generated. The transceiver 10A may also be optionally equipped with electrical contacts to make communication with receiving cradles 50 as illustrated in FIGS. 3 and 4 below. Although transceiver 10A of FIG. 1A may be used in any of the foregoing embodiments, other transceivers may also be used. For example, the transceiver may lack one or more features of the transceiver 10A. For example, a suitable transceiver need not be a manually portable device, and/or need not have a top-mounted display, and/or may selectively lack other features or exhibit further differences.

FIG. 1B is a graphical representation of a plurality of scan planes that form a three-dimensional (3D) array having a substantially conical shape. An ultrasound scan cone 40 formed by a rotational array of two-dimensional scan planes 42 projects outwardly from the dome 20 of the transceivers 10A. Other transceiver embodiments of transceiver 10A may also be configured to develop a scan cone 40 formed by a rotational array of two-dimensional scan planes 42. The pluralities of scan planes 40 may be oriented about an axis 11 extending through the transceivers 10A-B. One or more, or preferably each of the scan planes 42 may be positioned about the axis 11, preferably, but not necessarily at a predetermined angular position $\theta$. The scan planes 42 may be mutually spaced apart by angles $\theta_1$ and $\theta_2$. Correspondingly, the scan lines within each of the scan planes 42 may be spaced apart by angles $\phi_1$ and $\phi_2$. Although the angles $\theta_1$ and $\theta_2$ are depicted as approximately equal, it is understood that the angles $\theta_1$ and $\theta_2$ may have different values. Similarly, although the angles $\phi_1$ and $\phi_2$ are shown as approximately equal, the angles $\phi_1$ and $\phi_2$ may also have different angles. Other scan cone configurations are possible. For example, a wedge-shaped scan cone, or other similar shapes may be generated by the transceiver 10A.

FIG. 1C is a graphical representation of a scan plane 42. The scan plane 42 includes the peripheral scan lines 44 and 46, and an internal scan line 48 having a length r that extends outwardly from the transceivers 10A. Thus, a selected point along the peripheral scan lines 44 and 46 and the internal scan line 48 may be defined with reference to the distance r and angular coordinate values $\phi$ and $\theta$. The length r preferably extends to approximately 18 to 20 centimeters (cm), although any length is possible. Particular embodiments include approximately seventy-seven scan lines 48 that extend outwardly from the dome 20, although any number of scan lines is possible.

As described above, the angular movement of the transducer may be mechanically effected and/or it may be electronically or otherwise generated. In either case, the number of lines 48 and the length of the lines may vary, so that the tilt angle $\phi$ sweeps through angles approximately between $-60°$ and $+60°$ for a total arc of approximately 120°. In one particular embodiment, the transceiver 10 may be configured to generate approximately about seventy-seven scan lines between the first limiting scan line 44 and a second limiting scan line 46. In another particular embodiment, each of the scan lines has a length of approximately about 18 to 20 centimeters (cm). The angular separation between adjacent scan lines 48 (FIG. 1B) may be uniform or non-uniform. For example, and in another particular embodiment, the angular separation $\phi_1$ and $\phi_2$ (as shown in FIG. 1C) may be about 1.5°. Alternately, and in another particular embodiment, the angular separation $\phi_1$ and $\phi_2$ may be a sequence wherein adjacent angles may be ordered to include angles of 1.5°, 6.8°, 15.5°, 7.2°, and so on, where a 1.5° separation is between a first scan line and a second scan line, a 6.8° separation is between the second scan line and a third scan line, a 15.5° separation is between the third scan line and a fourth scan line, a 7.2° separation is between the fourth scan line and a fifth scan line, and so on. The angular separation between adjacent scan lines may also be a combination of uniform and non-uniform angular spacings, for example, a sequence of angles may be ordered to include 1.5°, 1.5°, 1.5°, 7.2°, 14.3°, 20.2°, 8.0°, 8.0°, 8.0°, 4.3°, 7.8°, and so on.

FIG. 1D a graphical representation of a plurality of scan lines emanating from a hand-held ultrasound transceiver forming a single scan plane 42 extending through a cross-section of an internal bodily organ. The number and location of the internal scan lines emanating from the transceivers 10A within a given scan plane 42 may thus be distributed at different positional coordinates about the axis line 11 as may be required to sufficiently visualize structures or images within the scan plane 42. As shown, four portions of an off-centered region-of-interest (ROI) are exhibited as irregular regions 49. Three portions may be viewable within the scan plane 42 in totality, and one may be truncated by the peripheral scan line 44.

FIG. 2A depicts a partial schematic and partial isometric and side view of a transceiver, and a scan cone array comprised of 3D-distributed scan lines in alternate embodiment of an ultrasound system. A plurality of three-dimensional (3D) distributed scan lines emanating from a transceiver that cooperatively forms a scan cone 30. Each of the scan lines have a length r that projects outwardly from the transceivers 10A-10E of FIGS. 1A-1E. As illustrated the transceiver 10A emits 3D-distributed scan lines within the scan cone 30 that may be one-dimensional ultrasound A-lines. The other transceiver embodiments 10B-10E may also be configured to emit 3D-distributed scan lines. Taken as an aggregate, these 3D-distributed A-lines define the conical shape of the scan cone 30. The ultrasound scan cone 30 extends outwardly from the dome 20 of the transceiver 10A, 10B and 10C centered about an axis line 11. The 3D-distributed scan lines of the scan cone 30 include a plurality of internal and peripheral scan lines that may be distributed within a volume defined by a perimeter of the scan cone 30. Accordingly, the peripheral scan lines 31A-31F define an outer surface of the scan cone 30, while the internal scan lines 34A-34C may be distributed between the respective peripheral scan lines 31A-31F. Scan line 34B may be generally collinear with the axis 11, and the scan cone 30 may be generally and coaxially centered on the axis line 11.

The locations of the internal and peripheral scan lines may be further defined by an angular spacing from the center scan line 34B and between internal and peripheral scan lines. The angular spacing between scan line 34B and peripheral or internal scan lines may be designated by angle ($\Phi$) and angular spacings between internal or peripheral scan lines may be designated by angle $\emptyset$. The angles $\Phi_1$, $\Phi_2$, and $\Phi_3$ respectively define the angular spacings from scan line 34B to scan lines 34A, 34C, and 31D. Similarly, angles $\emptyset_1$, $\emptyset_2$, and $\emptyset_3$ respectively define the angular spacings between scan line 31B and 31C, 31C and 34A, and 31D and 31E.

With continued reference to FIG. 2A, the plurality of peripheral scan lines 31A-E and the plurality of internal scan lines 34A-D may be three dimensionally distributed A-lines (scan lines) that are not necessarily confined within a scan plane, but instead may sweep throughout the internal regions and along the periphery of the scan cone 30. Thus, a given point within the scan cone 30 may be identified by the coordinates r, $\Phi$, and $\emptyset$ whose values generally vary. The number and location of the internal scan lines emanating from the transceivers 10A-10E may thus be distributed within the scan cone 30 at different positional coordinates as required to sufficiently visualize structures or images within a region of interest (ROI) in a patient. The angular movement of the ultrasound transducer within the transceiver 10A-10E may be mechanically effected, and/or it may be electronically generated. In any case, the number of lines and the length of the lines may be uniform or otherwise vary, so that angle $\Phi$ sweeps through angles approximately between $-60°$ between scan line 34B and 31A, and $+60°$ between scan line 34B and 31B. Thus angle $\Phi$ in this example presents a total arc of approximately 120°. In one embodiment, the transceiver 10A, 10B and 10C may be configured to generate a plurality of 3D-distributed scan lines within the scan cone 30 having a length r of approximately 18 to 20 centimeters (cm). Alternate embodiments of the transceivers 10A-10E may employ gender charger button and related circuitry to serve as a means for informing software algorithms discussed below that ultrasound energy scans arise from either a female or a male patient that is undergoing ultrasound probing. The gender button provided definitional information that may employs modification to the algorithms to optimize detection and measurement of bladders in males, females that have not undergone hysterectomy procedures, females that have undergone hysterectomy procedures, and small male and female children.

Figure 2B:
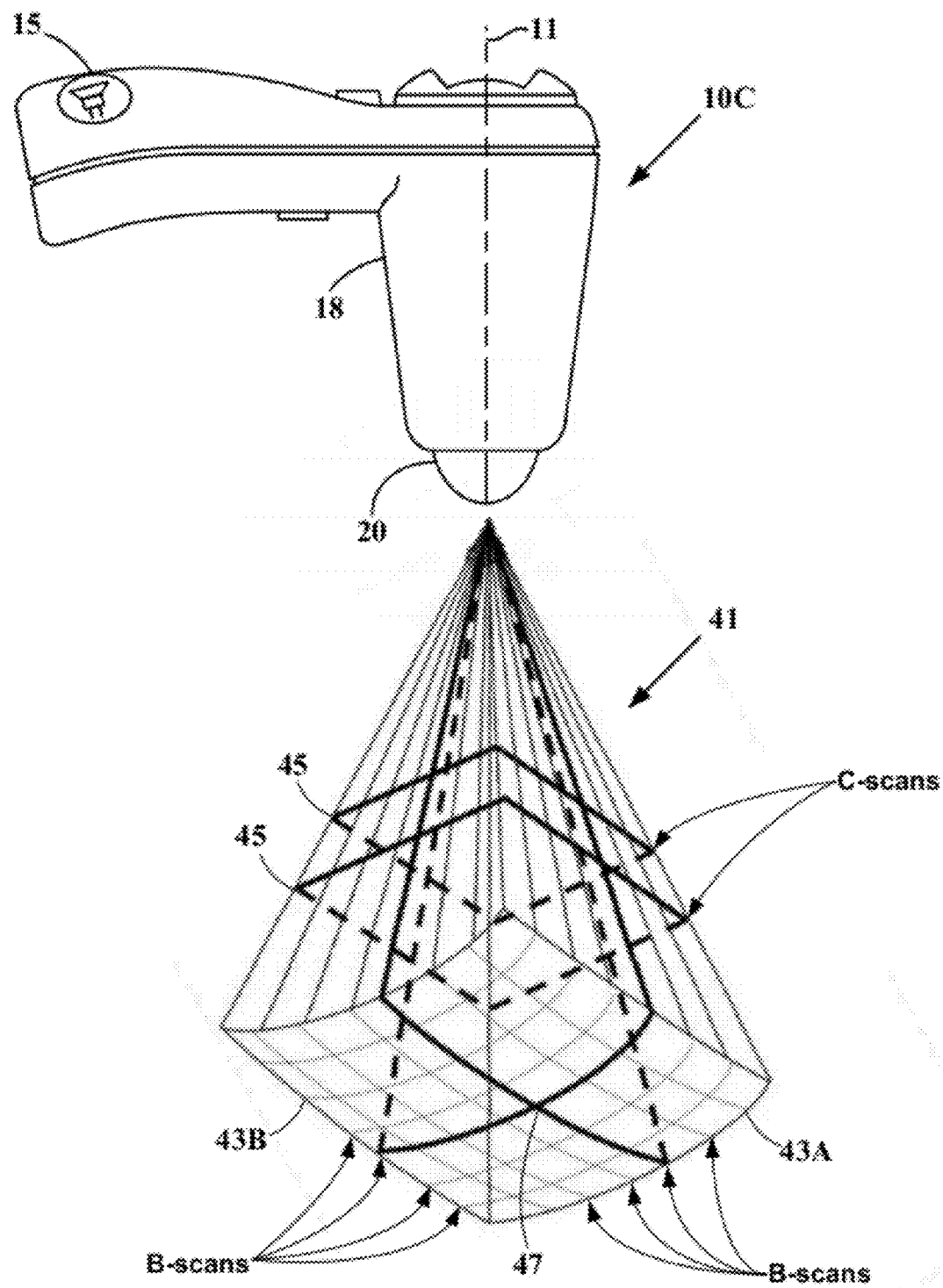
FIG. 2B illustrates a side and partial isometric that schematically depicts an harmonic ultrasound scanner employing C-mode and B-mode ultrasound modalities.

FIG. 2B illustrates a transceiver 10C configured with a transducer designed to provide a fan-like conic scan cone 41 utilizing C-mode and B-mode ultrasound modalities. The transceiver 10C projects a series of B-mode scan planes 43A and 43B that oscillate like a pendulum between extremes within the scan cone 41. The B-mode scan planes 43 are derived from a plurality of scan lines similar to scan lines 44, 46, and 48 of FIGS. 1C and D. The pendulum oscillating scan planes 43A and 43B may be arranged substantially at right angles to each other as depicted at axis crossing 47. The oscillating scan planes 43A and/or 43B may define a series of C-scan planes 45 that vary in depth location from the transceiver dome 20. The C-scan planes 45 move from the transducer vanishing point, and the B-scan planes angularly radiate from the transducer vanishing point. For transceiver 10C users, a portion of the bladder taken as a C-mode shape is displayed on the transceiver display 16. The C-scan geometry showed as scan planes 45 present a substantially square-like ultrasound area within the scan cone 41. The C-Scan image information contained within scan planes 45 presents a cross-section view of the ultrasound at a particular depth probed by the transceiver 10C. The C-mode is more representative of a portion of the bladder than the actual whole of the bladder. In this depiction, the C-Scan illustrates a cross-section view of the ultrasound at a particular depth to obtain a targeting image of the bladder. The targeting image is more of a binary image showing the lines and spaces that are inside the bladder versus those that are outside of the bladder. The definition of C-mode image basically is a plane parallel to the face of the transducer to obtain a projection image of the bladder region. The C-mode acquired projection image yields bladder information not confined to simply one a single plane parallel to the transducer surface, but multiple planes denoted as C-scans. In the transceivers 10A/B/C substantially similar to the BVI9400 transceiver product, the C-mode acquired projection image is binary, and includes a non-bladder region and a bladder region. The bladder region is presented as an interpolated shape that is generated from one side to the opposite side, for example the left most and the right most sides of a valid segmentation, or cut, the bladder region on all planes. A method of acquiring a C-mode final image is described in FIG. 9D below.

Figure 2C:
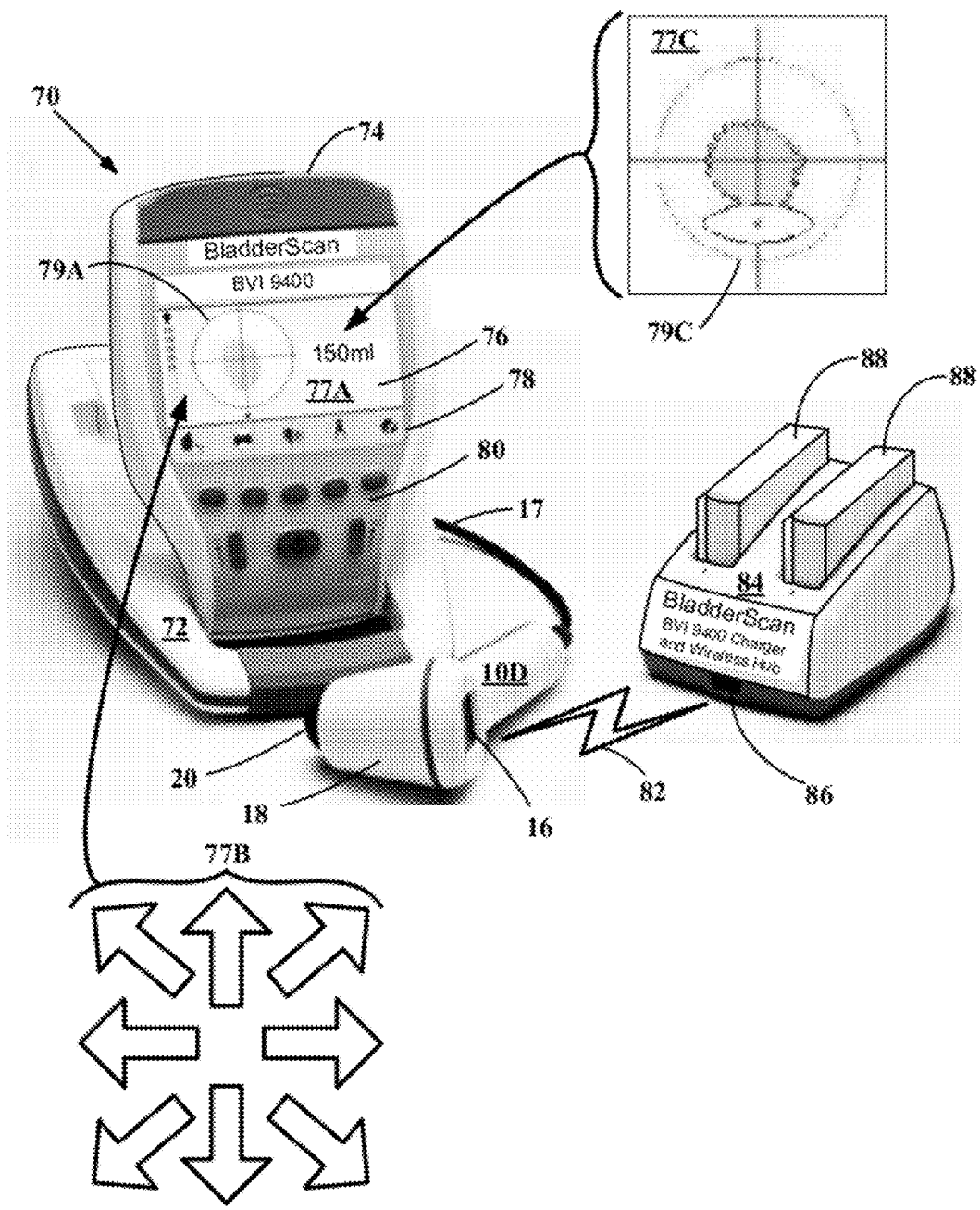
FIG. 2C illustrates a partial isometric and schematic view of an ultrasound harmonic bladder scanner system.

FIG. 2C illustrates a partial isometric and schematic view of an ultrasound harmonic bladder scanner system 70 utilizing a transceiver probe 10D and console 74 combination 74. The harmonic bladder scanner system 70 is battery powered and portable and may also be referred to as the BVI9400 BladderScan system. Other embodiments may include line power. The ultrasound transceiver 10D is configured to send out and receive ultrasound RF signals. The received RF is transmitted to console 74. The DSP in console processed the RF information to extract the harmonic ratio as an important feature of each line. Then an artificial neural network is used to classify each line as bladder line or tissue line. The result gradings are integrated with the image processing module for accurate segmentation and volume measurement.

The transceiver 10D presents a similar transceiver display 16, housing 18 and dome 20 design as transceivers 10A, 10B and 10C, and is in signal communication to console 74 via signal cable 17. The console 74 may be pivoted from console base 72. The console 74 includes a display 76, detection and operation function panel 78, and select panel 80. The detection and operation function provide for targeting the bladder, allow user voice annotation recording, retrieval and playback of previously recorded voice annotation files, and current and previously stored 3D and 2D scans. In the display 76 is screenshot 76 having a targeting icon 79A with cross hairs centered in a cross sectional depiction of a bladder region. Other screen shots may appear in the display 76 depending on which function key is pressed in the function panel 78. A targeting icon screenshot 77B with a plurality of directional arrows may appear and flash to guide the user to move the transceiver 10C to center the bladder. The targeting icon screenshot 77B may also appear on the display 16 of the transceiver 10D. The targeting icon screenshot 77B similarly guides the user to place the transceiver 10D to center the bladder or other organ of interest as the directional indicator panel 22 depicted in FIG. 1A above. An initial bladder view screenshot 77C may appear in which target icon 79A shows a central bladder region appearing within the cross hairs above the oval shaped pubic bone. In wireless communication via wireless signal 82, the output from the transceiver 10D may be outputted to a wireless hub 84 via wireless signal port 86. The wireless hub 84 also serves to charge batteries 88 for loading into the battery compartment (not shown) of console 74. All the calculations may be performed in the imaging console 74. The 9400-embodiment system 70 does not require a computer or network to complete the harmonic analysis and imaging processing. In other embodiments, the system 70 may utilize the wireless hub 84 as a gateway to transmit transceiver 10D acquired harmonic imaging information in local and Internet systems similar to those described in FIGS. 3 and 4 below.

FIG. 3 is a schematic illustration of a server-accessed local area network in communication with a plurality of ultrasound harmonic imaging systems. An ultrasound system 100 includes one or more personal computer devices 52 that may be coupled to a server 56 by a communications system 55. The devices 52 may be, in turn, coupled to one or more ultrasound transceivers 10A and/or 10B and/or 10C, for examples the ultrasound sub-systems 60A-60D. Ultrasound based images of organs or other regions of interest derived from either the signals of echoes from fundamental frequency ultrasound and/or harmonics thereof, may be shown within scan cone 30 or 40 presented on display 54. The server 56 may be operable to provide additional processing of ultrasound information, or it may be coupled to still other servers (not shown in FIG. 3) and devices. Transceivers 10A/B/C may be in wireless communication with computer 52 in sub-system 60A, in wired signal communication in sub-system 10B, in wireless communication with computer 52 via receiving cradle 50 in sub-system 10C, or in wired communication with computer 52 via receiving cradle 50 in sub-system 10D. The ultrasound system 100 may be adapted for harmonic analysis by employing the console 74 algorithmic functions depicted in the harmonic bladder scanner system 70 of FIG. 2C into the personal computer devices 52.

FIG. 4 is a schematic illustration of the Internet in communication with a plurality of ultrasound systems. An Internet system 110 may be coupled or otherwise in communication with the ultrasound harmonic sub-systems 60A-60D. The ultrasound system 110 may be adapted for harmonic analysis by employing the console 74 algorithmic functions depicted in the harmonic bladder scanner system 70 of FIG. 2C into the personal computer devices 52.

Figure 5:
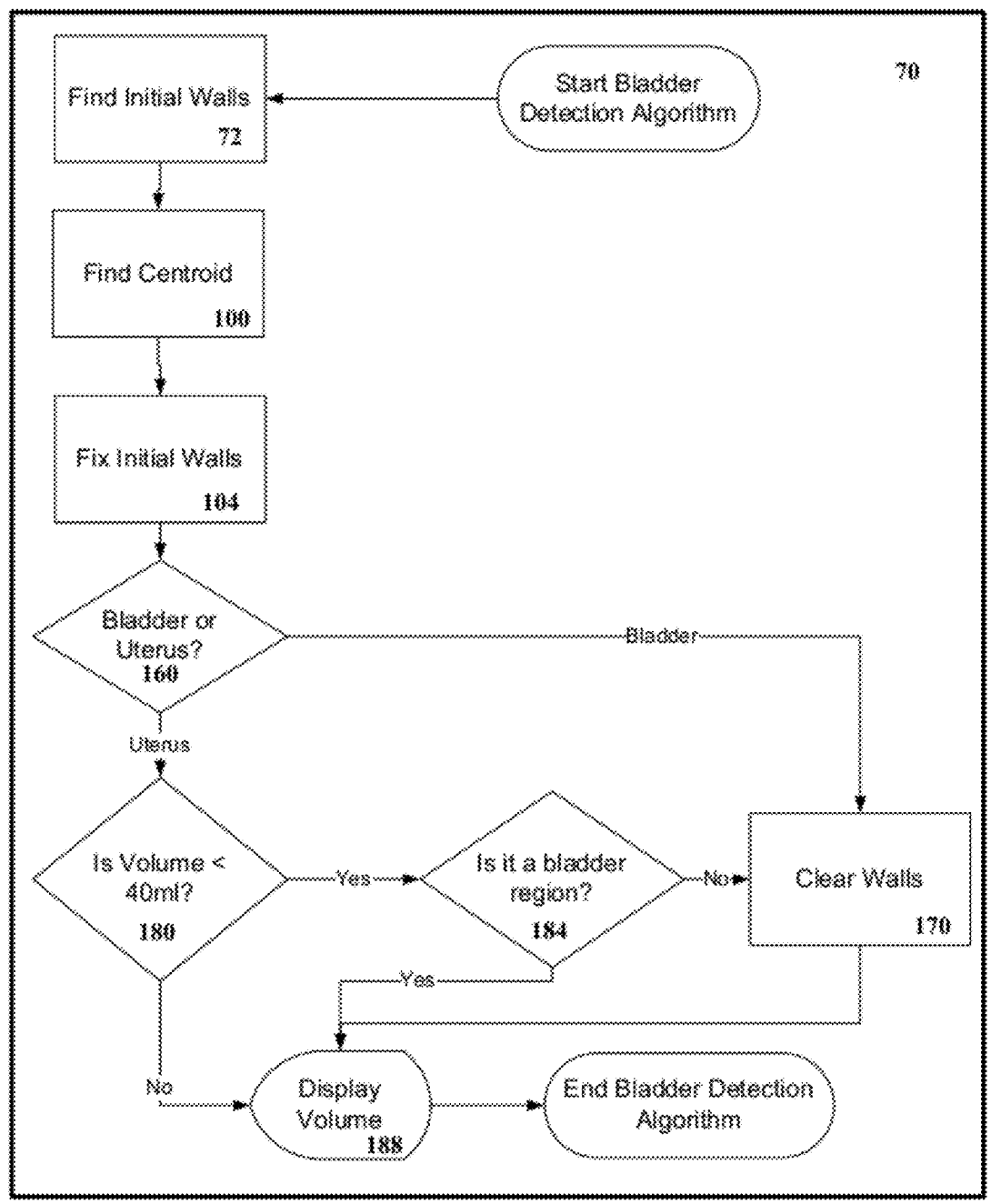
FIG. 5 depicts a flowchart of a bladder detection algorithm employing fundamental ultrasound energies.

FIG. 5 depicts a flowchart of a bladder detection algorithm 70 employing fundamental ultrasound energies. The 3000 and 6000 transceivers utilize the bladder detection algorithm 70 to obtain bladder volume measurement via a bladder detection module employing B-mode image information for segmentation and subsequent 3D volume computations based on the B-mode segmentation. However, female uterus and/or B-mode image noise may obscure bladder detection accuracy in the 3000 and 6100 series transceivers.

The fundamental frequency based bladder detection algorithm 70 utilizes a particular embodiment of the transducers 10A-B designated as transducer device model BVI6100. The algorithm 70 describes the segmentation processes defined by computer executable instructions employed in concert with the BVI6100 device. The BVI6100 imaging characteristics are different from another particular embodiment of the transducer 10A-B designated as a BVI3000 device that employs a different computer executable algorithm for bladder detection.

The fundamental bladder detection algorithm 70 used in the BVI 3000 and 6100 devices begins with process block Find Initial Wall process block 100 using A-mode ultrasound data that incorporates data-smoothing. Find Initial Wall 100 looks for the front and back walls of the bladder illustrated and described in FIG. 6 below. After the front and back walls are found, a line passing through the center of the bladder is determined in the following process block Find Centroid 142.

This center bladder line is used as a seed from which process block Fix Initial Walls 150 utilizes as illustrated and described in FIG. 7 below. Fix Initial Walls 150 refines the initial wall points, removes any outliers, and fills gaps in the detected wall location regions. Thereafter, an answer is sought to the query "Bladder or Uterus?" in decision diamond block 160 more fully described and illustrated in FIG. 8 below. Briefly, "Bladder or Uterus" decision 160 determines whether the detected region is a bladder or a uterus when the gender button on the transceivers 10A-D devices indicate that the scan is for a female. If affirmative for bladder detection, its volume is computed and displayed on the output. This is achieved in algorithm 70 at process block Clear Walls 170, followed by process block Display Volume 188 wherein the volume is displayed on the BVI6100 or its transducer 10A-B equivalents.

If negative for bladder detection, in other words that a uterus was detected, algorithm 70 continues the calculated volume is cleared and a zero volume is displayed. For a non-uterus region, if the volume is very small, then checks are made on the size of and signal characteristics inside the detected region to ensure that it is bladder and not another tissue. This is achieved in algorithm 70 by securing an answer to the query "Is volume less than 40 ml?" at decision diamond 180. If negative for a volume <40 ml, algorithm 70 continues to process block Display Volume 188 wherein the volume is displayed on the BVI6100 or transducers similar to transducers 10A-B. If affirmative for a volume <40 ml, algorithm 70 continues to answer the query "Is it a bladder region?" at decision diamond 184. If negative, algorithm 70 proceeds to Clear Walls 70, and if affirmative, proceeds to Display Volume 188. After Display Volume 188, the Fundamental Bladder Detection algorithm 70 is completed.

Figure 6:
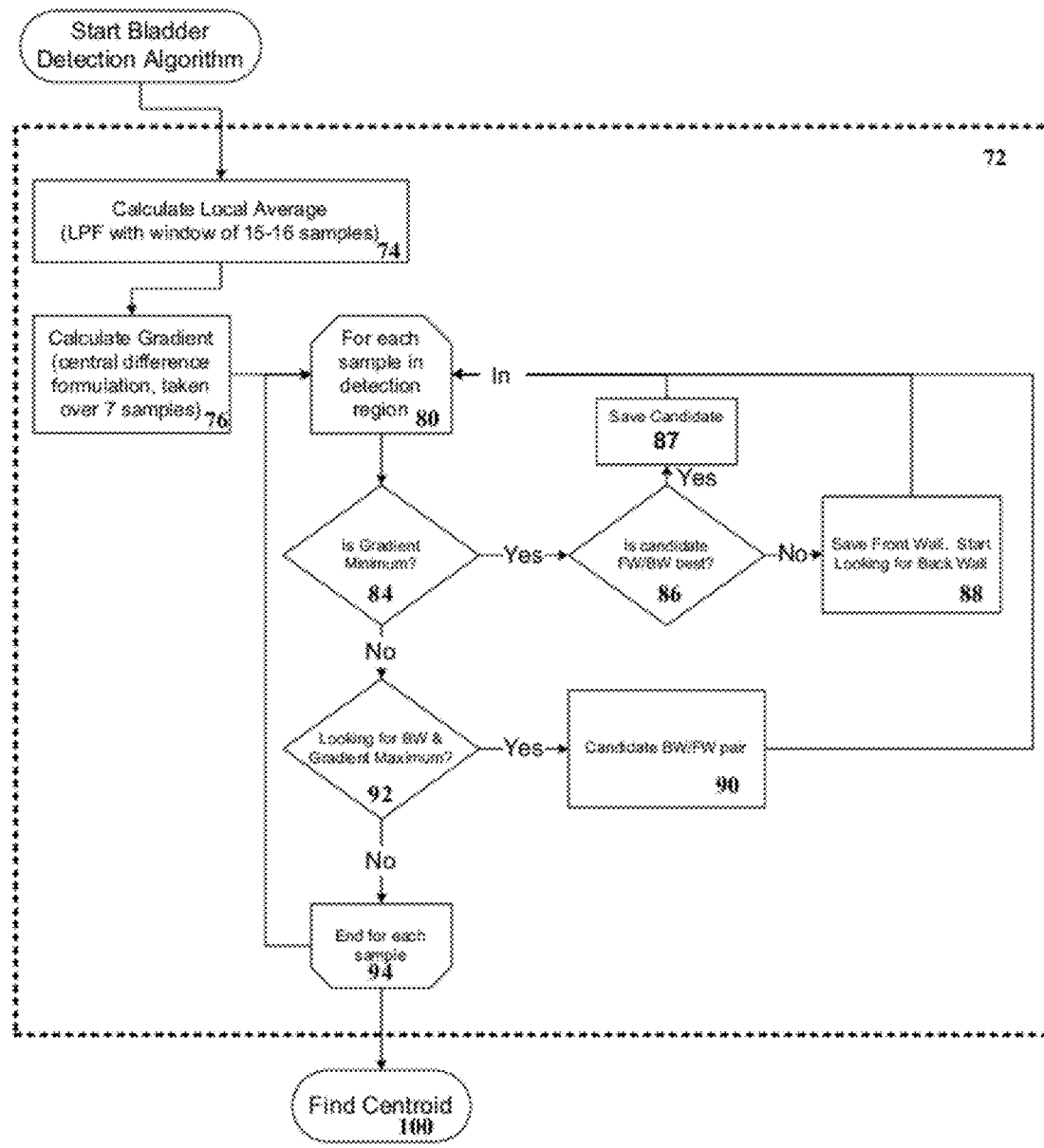
FIG. 6 depicts a flowchart of the Find Initial Walls sub-algorithm of FIG. 5.

FIG. 6 depicts a flowchart of the Find Initial Walls sub-algorithm of FIG. 5. Find Initial Walls 72 process is executed on every A-mode scan line and is subjected to averaging and low-pass filtering using a 15 or 16 sample set beginning with process block 74. Next, a local gradient 76 at process block 76 is computed for each sample point using a central difference formulation taken for seven samples. The central difference formulation is defined by equations 1-6 (Eq. 1-6) below:

The standard central difference formula is given in Equation 1:

$$dx_i = x_{i+1/2} - x_{i-1/2} \qquad \text{Eq. 1}$$

This formula assumes that the function is defined at the half-index, which is usually not the case. The solution is to widen the step between the samples to 2 and arrive at the equation in Eq. 2.

$$dx_i = \frac{1}{2}(\overline{x}_{i+1} - \overline{x}_{i-1}) \qquad \text{Eq. 2}$$

The normalization factor is simply the distance between the two points. In, the distance separating the two means in the calculation was 1, and in Eq. 2, the step between the two means is 2. The normalization of the gradient by the step size, while mathematically correct, incurs a cost in terms of operation. This operation is neglected in the gradient calculation for the bladder wall detection algorithm with minimal effect: since the same calculation is performed for every data sample, every data sample can have the same error and thus the relative gradient values between different samples remain unchanged.

To further amplify wall locations, the gradient calculation is expanded to three neighboring points to each side of the sample in question. This calculation is shown in Eq. 3. This calculation is simply the sum of three gradient approximations and thus the end result can be 12 times its normal value. This deviation from the true mathematical value has minimal effect since the calculation is the same at each point and thus all the gradient values can be 12 times their usual value. The advantage to using the three neighboring points is that more information about the edge is included in the calculation, which can amplify the strong edges of the bladder and weaken the false-edges caused by the noise process in the image.

$$dx_i = \overline{x}_{i+3} + \overline{x}_{i+2} + \overline{x}_{i+1} - \overline{x}_{i-1} - \overline{x}_{i-2} - \overline{x}_{i-3} \qquad \text{Eq. 3}$$

The full calculation is written in

Eq. 4. The first line shows the summation calculation to obtain the means, and the difference operations to obtain the gradient. The entire sum is normalized by 15, the number of points included in each local mean. The second line of the operation shows the result when the summations are simplified, and represents the maximal implementation of the calculation. This calculation incurs a cost of 23 additions or subtractions, 2 floating-point multiplications, 1 floating point division, and at least 1 temporary variable. This operation cost is incurred for 91% of the data samples.

$$dx_i = \frac{\sum_{j=i+3-7}^{j=i+3+7} x_j - \sum_{j=i-3-7}^{j=i-3+7} x_j + \sum_{j=i+2-7}^{j=i+2+7} x_j - \sum_{j=i-2-7}^{j=i-2+7} x_j + \sum_{j=i+1-7}^{j=i+1+7} x_j - \sum_{j=i-1-7}^{j=i-1+7} x_j}{15}$$

$$= \frac{x_{i+10} - x_{i-10} + x_{i+5} - x_{i-5} + 2(x_{i+9} - x_{i-9} + x_{i+6} - x_{i-6}) + 3(x_{i+8} - x_{i-8} + x_{i+7} - x_{i-7})}{15} \qquad \text{Eq. 4}$$

The cost of the calculation can be reduced by not simplifying the summations and using a running sum operation. In that manner, only one mean needs to be calculated for each point, but that mean needs to be for the i+3 point. The running sum calculation uses the previous sum, and then corrects the sum by subtracting the old "left hand" end point and adding the new "right hand" end point. The operation is shown in Eq. 5. This running sum operation incurs a cost of 5 additions and subtractions.

$$\overline{x}_{i+3} = \sum_{j=i+3-7}^{j=i+3+7} x_j = \overline{x}_{i+3-1} - x_{i+3-8} + x_{i+3+7}$$

$$= \overline{x}_{i+2} - x_{i-5} + x_{i+10} \qquad \text{Eq. 5}$$

Since the running sum was calculated for the i+3 point, all average values are available for the gradient calculation. This calculation is shown in Equation 6:

$$dx_i = \frac{-\bar{x}_{i-3} - \bar{x}_{i-2} - \bar{x}_{i-1} + \bar{x}_{i+1} + \bar{x}_{i+2} + \bar{x}_{i+3}}{16} \quad \text{Eq. 6}$$

This equation has the same form as the one in

Eq. 3 except for the normalization factor of 16. This normalization factor is not a result of the gradient operation, but rather it is the normalization factor mean calculation. The factor of 16 is used instead of the standard value of 15 that one would expect in a 15-point average for this simple reason: using a factor of 16 eliminates floating-point division. If the means are normalized by 16, then the division operation can be replaced by a "right"-shift by 4 at a significantly lower cost to the embedded system. Therefore the gradient operation has eleven additions and subtractions and one shift by 4.

Adding the operational cost of the running sum calculation gives an overall cost of 16 additions and subtractions and the shift. The clear victory in this simplification is the elimination of multiplication and division from the operation.

Returning to FIG. 6, the results from local gradient 76 is the subjected to loop limit processing between blocks 80 and 94 to obtain the best front wall and back wall pair for each scan line denoted as a tissue gradient or tissue delta. The best front wall and back wall pair on each line is defined as the front wall and back wall pair for which the pixel intensity difference in the back wall gradient and front wall gradient is the maximum and the smallest local average between front wall and back wall pair is the minimum.

The loop limit processing begins with loop limit block 80 that receives pixel values for each sample in the detection region and subjects the pixel intensity values to determine whether the gradient is minimum at decision diamond 84. If affirmative, then the pixel values are ascertained whether it s the best front wall-back wall (FW/BW) candidate combination at decision diamond 86. If affirmative, the FW/BW candidate pair is saved and loop limit processing returns to limit block 80. If negative, at process block 88, the Front Wall pixel value is saved and another back wall candidate is sought with a subsequent return to loop limit block 88.

Returning to decision diamond 84, if the answer is negative for "Is gradient Minimum?, sub-algorithm 72 continues to decision diamond 92 to determine whether the back wall and the gradient is maximum. If affirmative, at process block 90, a candidate BW/FW pair is established and sub-algorithm re-routes to loop limit block 80. If negative, the end of analysis for a particular FW/BW candidate occurs at loop limit block 94 either routes back to the limit loop block 80 or exits to find centroid 100.

Formulations relating to Find Centroid 100 are based on coordinate geometries described in equations 7 and 8 utilizing coordinate conversions. The coordinate conversions are shown in Eq. 7 where 38 is the index of the broadside beam (the ultrasound ray when φ=0), φ is the index of the line, θ is the angle of the plane. The plane angle is shifted by π to ensure that the sign of the x and y coordinates match the true location in space.

$x=(38-\phi) \cos (\pi-\theta)$ $y=(38-\phi) \sin (\pi-\theta)$ \quad Eq. 7

The trigonometric functions can be calculated for a table of θ values such that the cosine and sine calculations need not be performed for each of the points under consideration. The closest plane can be found by finding the shortest vector from each plane to the centroid. The shortest vector from a plane to a point can be the perpendicular to the projection of the centroid on the plane. The projection of the centroid on the plane is defined as the dot product of the centroid vector, c, with the plane definition vector, a, divided by the length of the plane definition vector. If the plane definition vector is a unit vector, then the division operation is unnecessary. To find the perpendicular to the projection, it is sufficient to subtract the projection vector from the centroid vector as shown in Eq. 8:

$$\|c - proj_c a\|^2 = \left\| c - \frac{c \cdot a}{\|a\|^2} \right\|^2 \quad \text{Eq. 8}$$

The length of these projections can be found by calculating the Euclidean norm for each line. The Euclidean norm is more commonly known as the length or magnitude of the vector. To find the plane closest to the centroid, calculate the lengths for the perpendicular to the projection of the centroid on each plane, and take the plane with the shortest of these lengths.

Figure 7:
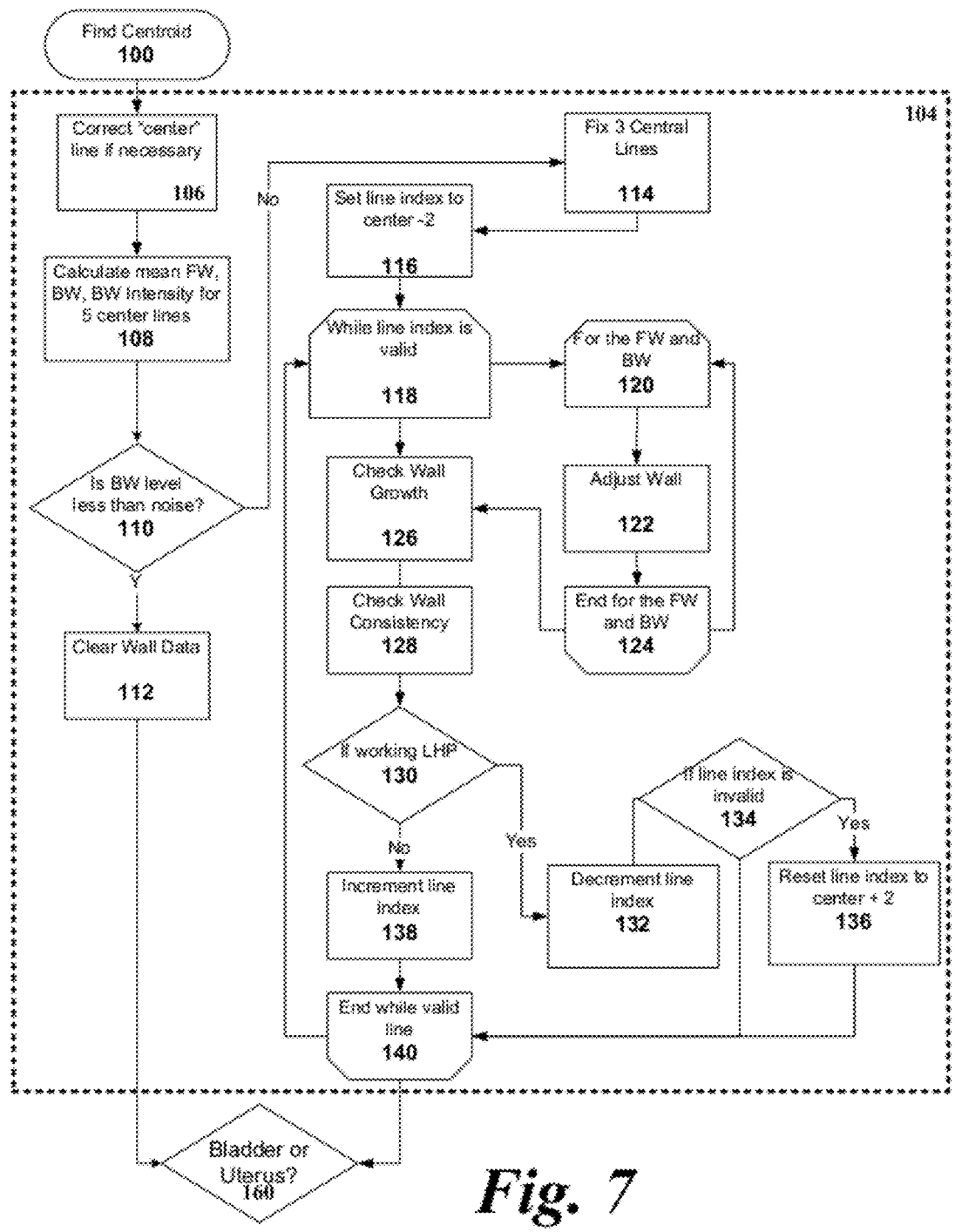
FIG. 7 depicts a flowchart of the Fix Initial Walls sub-algorithm of FIG. 5.

FIG. 7 depicts a flowchart of the Fix Initial Walls sub-algorithm 104 of FIG. 5. Fix Initial Walls 104 is responsible for refining the initial wall points, removing any outliers, and filling any gaps in the wall locations. The FixInitialWalls 104 operates on a plane-by-plane basis with the first plane to be processed being the one that is closest to the centroid of the initial walls and then the planes are processed moving in either direction of that plane. The FixInitialWalls 104 step starts with processing block 106 for correcting the "center line" in terms of where the "center line" is defined as the line on that plane with the maximum gradient difference between front wall and back wall. The correction of the front wall and back wall location at any line is carried out by a matched filtering-like step where the best location within a search limit is defined as the one for which the difference between points immediately outside the bladder and points immediately inside the bladder is maximum. Next, at process block 108, for 5 central lines, the back wall intensity is computed and if this intensity is less than expected noise at that depth, the lines are cleared and the algorithm proceeds to the next plane. At decision diamond 110, an answer to the query "Is BW level less than noise?" is sought. If affirmative, Wall data is cleared at process block 112, and fix initial walls 104 exits to decision diamond 160, "Bladder or Uterus"? If negative, then at process block 114, 3 central lines are fixed. This is followed by block 116 to continuously correct two lines on either side of the central lines using a line-fitting algorithm to set the line index to center −2. A missing line of data may be filled by the algorithm and any outliers are removed. Thereafter the results from continuous correction block 116 is then subjected to loop limit processing between blocks 118 and 140 to obtain the best front wall and back wall pair for each scan line denoted as a tissue gradient or tissue delta. The best front wall and back wall pair on each line is defined as the front wall and back wall pair for which the pixel intensity difference in the back wall gradient and front wall gradient is the maximum and the smallest local average between front wall and back wall pair is the minimum.

The loop limit processing begins with loop limit block 118 that receives pixel values for each sample in the detection region and subjects the pixel intensity values to prepare a wall location adjustment at subsidiary loop limit 120. The wall is adjusted at block 122 and forwarded subsidiary loop limit 124. The value obtained at loop limit 124 is compared with the line index while valid loop limit 118 by checking wall growth at block 126 and consistency at block 128. Thereafter, at decision diamond 130, an answer is sought to the query If the FW and BW pair provides a "Working Left Half Plane (LHP)" of a given scan plane undergoing analysis. If affirmative, at process block 132 a decrement line index is done, followed by a query "If line index is invalid" at decision diamond 134. If invalid, then at block 136, the line is reset 2 spaces from center, results forwarded to end loop limit 140, and fix initial walls 104 is completed and exits to decision diamond 160, "Bladder or Uterus". If valid, results are forwarded to end loop limit 140 for exiting to decision diamond 160. Returning to decision diamond 130, if the answer is negative for a working LHP, the line is incremented and forwarded to end loop limit 140, and fix initial walls 104 is completed and exits to decision diamond 160, "Bladder or Uterus".

Figure 8:
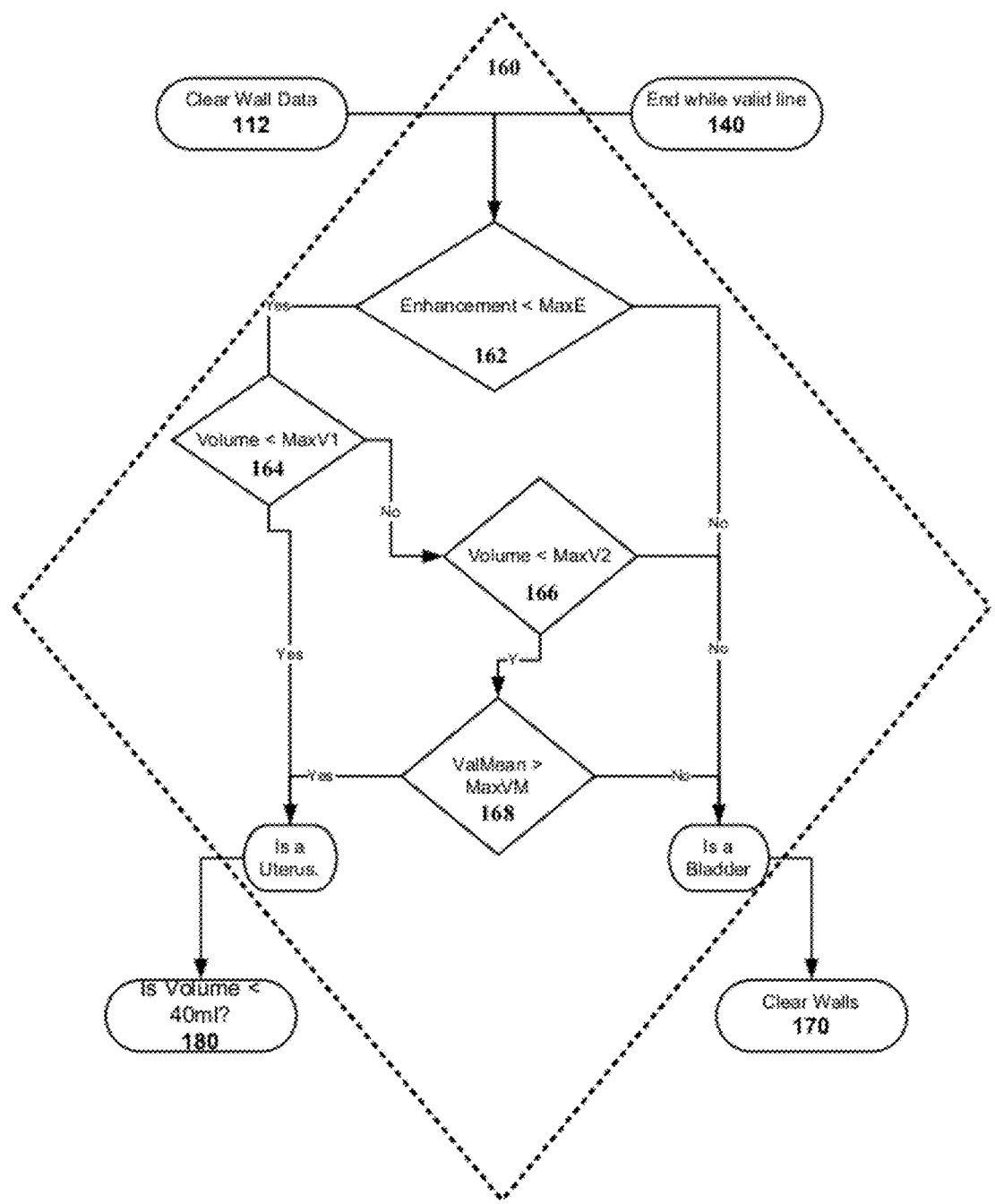
FIG. 8 depicts a flowchart of the Bladder or Uterus decision diamond of FIG. 5.

FIG. 8 depicts a flowchart of the Bladder or Uterus decision diamond of FIG. 5. In the "Bladder or Uterus?" decision diamond 160 of FIG. 5, entering from either Clear Wall Data process block 112 or End while valid line process block 140, the pixel values are ascertained whether the Enhancement is less than the MaxE at decision diamond 162. If negative for enhancement >MaxE, the cavity being detected is a bladder and decision diamond 160 is completed and exits to processing block Clear Walls 170. If affirmative that Enhancement <MaxE, then an answer is sought to the query "Is volume less than MaxV1?", a maximum first volume, at decision diamond 164. If affirmative, then cavity being measured is a uterus and decision diamond 160 is completed and exits to "Is volume <40 ml?" decision diamond 180. If, at decision diamond 164, it is negative to the statement "volume <MaxV1", then an answer is sought to the query "Is volume less than MaxV2?", a maximum second volume, at decision diamond 166. If negative, the cavity being detected is a bladder. If affirmative, then an answer is sought to the query "Is volume less than MaxV1?", a maximum first volume, at decision diamond 164

FIGS. 9A-F schematically illustrate algorithm flow charts of a BVI9400 bladder detection algorithm in the BVI9400 transceiver substantially similar to transceiver 10C of FIG. 2B. Other particular embodiments of the BVI9400 transceiver may be configured to be substantially equivalent to transceivers 10A and 10B respectively depicted in FIGS. 1A-D and FIG. 2B. The BVI9400 utilizes a 9400 series transducer that is more powerful and can achieve a duo format task of acquiring C-mode and B-mode based images with RF information collection and processing as described for FIGS. 9A-D. The B-mode image also renders higher resolution than the images produced by the 3000 and 6400 transceivers.

Figure 9A:
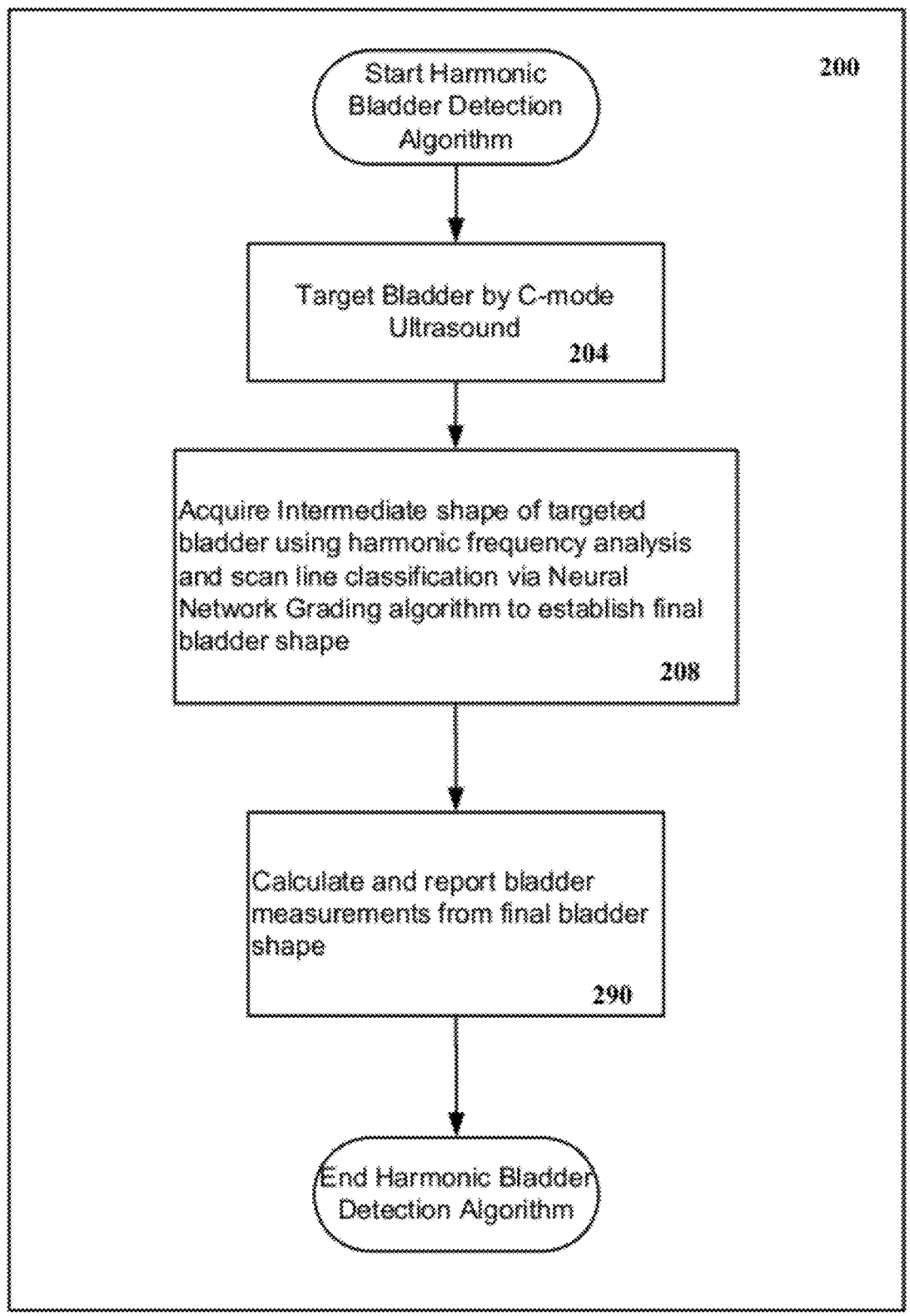
FIGS. 9A-F schematically illustrates algorithm flow charts of a BVI9400 bladder detection algorithm in the BVI9400 transceiver substantially similar to transceiver 10C of FIG. 2B.

FIG. 9A depicts a flowchart of a harmonic bladder detection algorithm 200 employing harmonic ultrasound energies. The harmonic bladder detection algorithm 200 begins by targeting block 202 in which the bladder is initially and approximately detected by C-mode ultrasound. A diagrammatic example of C-mode targeting is shown in FIG. 2B above in which a substantially square-like imaging plane is depicted. Transceivers 10A-B-C are placed against the patients lower abdominal area above the symphysis pubis (see FIG. 16 below), the cartilaginous joint located between the two pubic bones. The transceiver dome 20 is immersed into a sonic gel previously applied to the dermis of the patient above the symphysis pubis. A view sufficient to visualize and/or analyze the bladder is obtained. The view is guided by the directional arrows 22 depicted in FIG. 1A to center the bladder in the display 16 of the transceivers 10A-B-C or other display or monitor similar to monitor 54 in signal communication with the transceivers 10A-B-C. Bladder image views devoid of the pubic bone may be acquired as described below.

Once a sufficient view of the bladder is obtained by transceivers 10A-B-C, harmonic algorithm 200 continues to acquire block 208 in which an intermediate shape of the targeted bladder is acquired using harmonic frequency analysis and scan line classification via a Neural Network Grading Algorithm to establish final bladder shape. Scan planes similar to 44, 43A, 43B, and 45 depicted in FIGS. 1B-D, and 2B are acquired by the transceivers 10A-B-C using A-mode scan lines similar to those depicted in FIG. 1D. Echoes returning from the bladder region are captured by the transceivers 10A-B-C and echoic signals there from are conveyed to computers 52 configured to signal process the echoic signals by harmonic processes. Thereafter, once the final C-scan targeted bladder image is obtained, the bladder measurements are calculated and reported from the final bladder shape at process block 290 to complete the harmonic bladder detection algorithm 200.

Figure 9B:
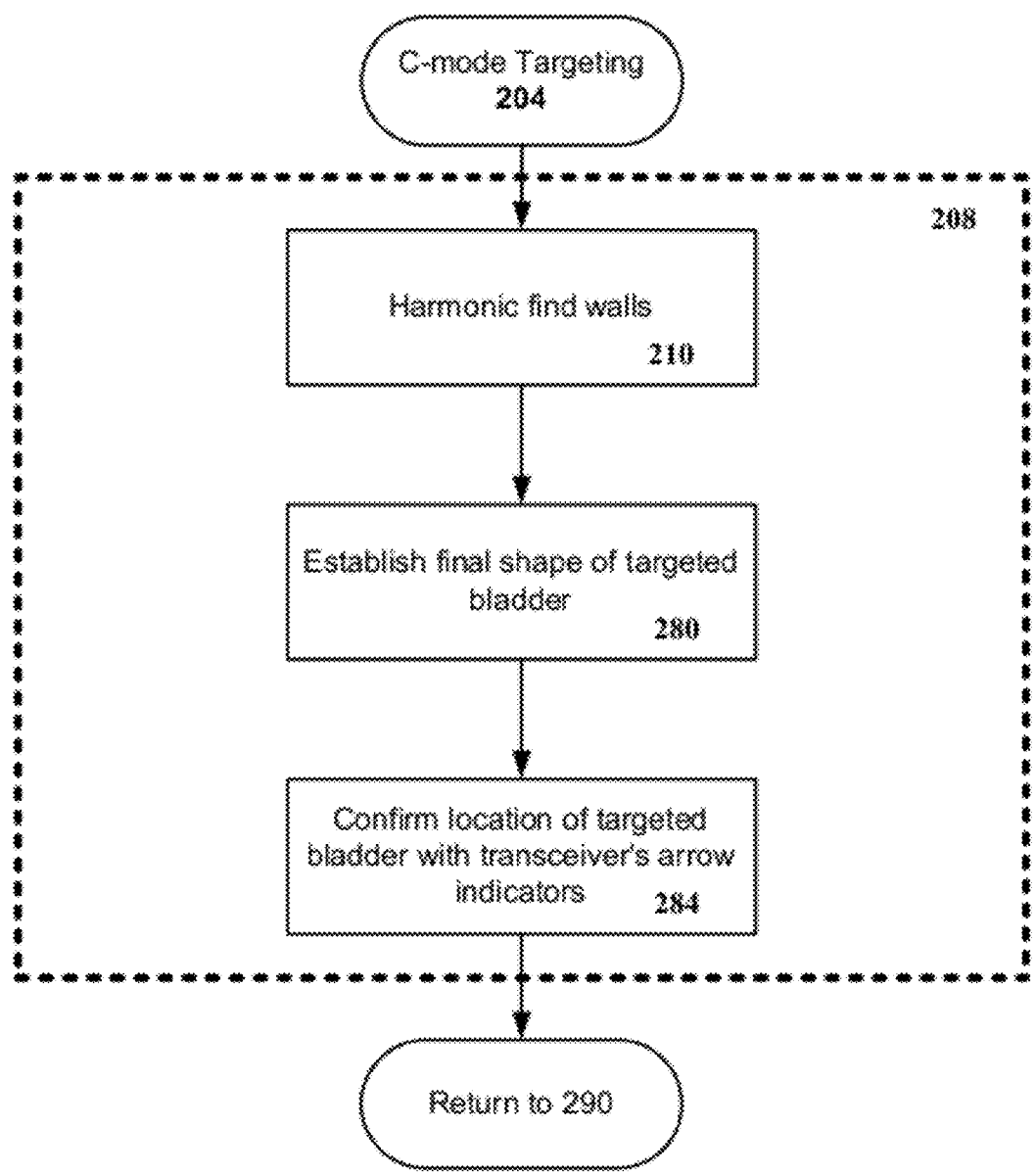

FIG. 9B depicts an expanded flow chart of the acquire intermediate bladder shape sub-algorithm 208 of FIG. 9A. In algorithm 208, intermediate shapes of organ cavities, i.e. the bladder is obtained. The algorithm draws the C-scan (or C-Mode) view of the bladder. The C-scan geometry is shown in FIG. 2B above and presents a substantially square ultrasound plane substantially perpendicular to the longitudinal projection the scan cone 41. The C-Scan presents a cross-section view of the ultrasound at a particular depth. In the case of the C-mode it is more representative for the bladder than an accurate depiction of the bladder. It is more of a binary image showing the lines and spaces that are inside the bladder versus those that are outside of the bladder. The output of FIG. 9B is the bladder segmentation and serves as the input to FIG. 9D below. The intermediate bladder shape sub-algorithm 208 includes harmonic find walls block 210, establish final shape of targeted bladder block 280, and confirm location of targeted bladder process block 284.

Figure 9C:
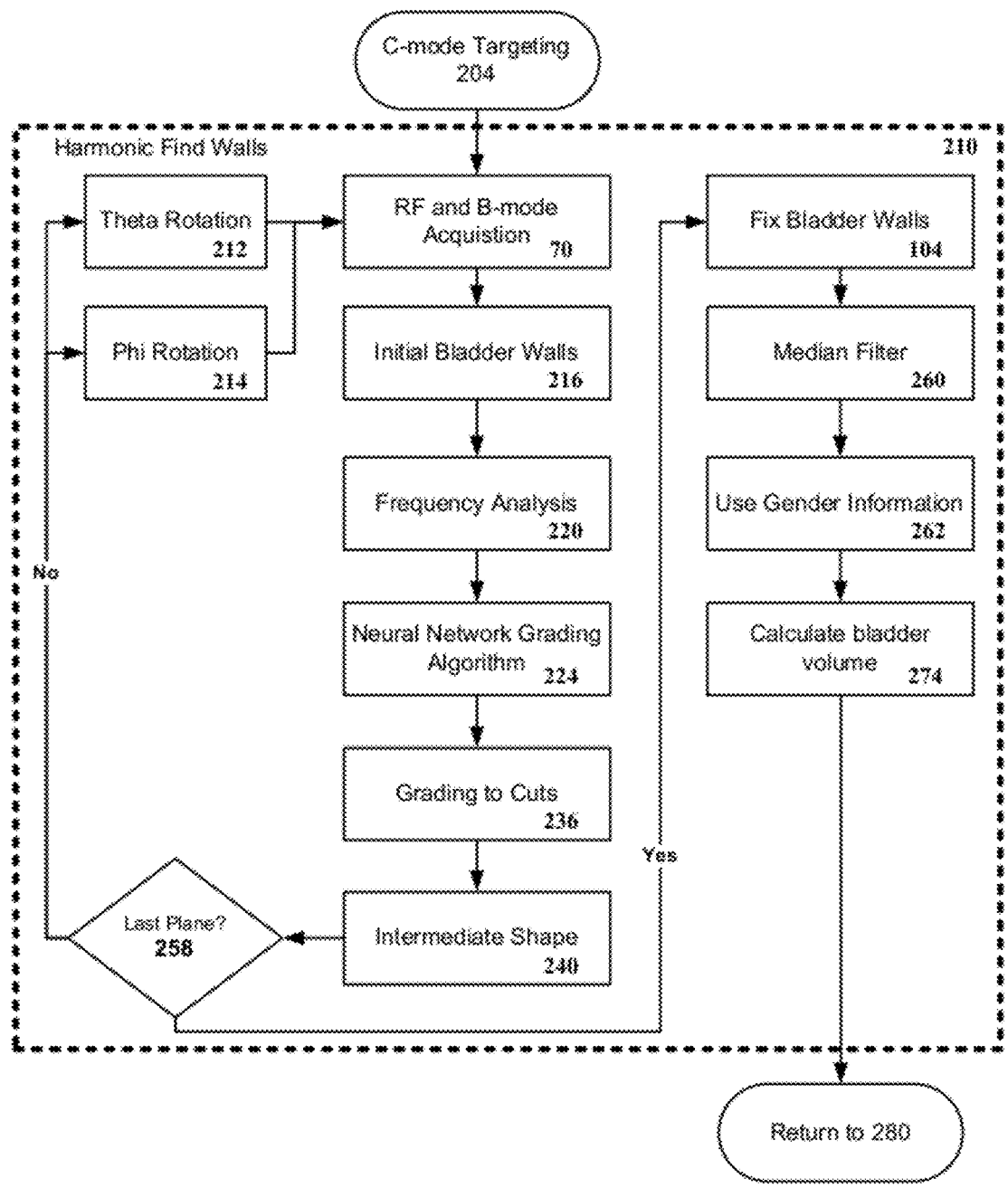

FIG. 9C depicts an expanded flow chart of the Harmonic Find Walls process block 210 of FIG. 9B. Entering from C-mode Targeting block 204, Harmonic Find Walls 210 begins with Radio Frequency B-mode Ultrasound acquisition block 70 described in FIG. 70 above, and includes variations of theta and phi rotation angle information from blocks 212 and 214. Thereafter, initial bladder walls block 216 is utilized to obtain front and back wall candidates similar to process 72 of FIG. 6. This is followed by Frequency analysis block 220 in which ultrasound RF signals are analyzed for their fundamental and harmonic frequency content. Then, at process block 224, the harmonic signals of the scan lines are analyzed for their likelihood of being classified as a cavity residing or non-cavity residing scan lines using a Neural Network Grading algorithm. Thereafter, the classified cavity residing or bladder residing scan lines are judged to constitute a validly segmented cavity or bladder region in a Grading to Cuts block 236. Using the valid segmentations or cuts, an intermediate cavity or bladder shape is obtained at process block Intermediate Shape 240. Thereafter, at decision diamond 250, answers to the query "Last Plane?" is sought. If negative, different theta and Phi rotation values are selected respectively from process blocks 212 and 214 for another cycle through process blocks 70-240. If affirmative, then harmonic find walls algorithm 210 routes to fix bladder Walls block 104 to undergo the processing described in FIG. 7. Thereafter, a median filter 260 is applied to the intermediate shaped image to which a use gender information algorithm is applied at process block 262. Thereafter, the volume of the bladder or cavity is calculated at block 274 and the Harmonic Find Walls sub-algorithm is completed and exits to process block 280, establish final shape of targeted bladder of FIG. 9B.

Figure 9D:
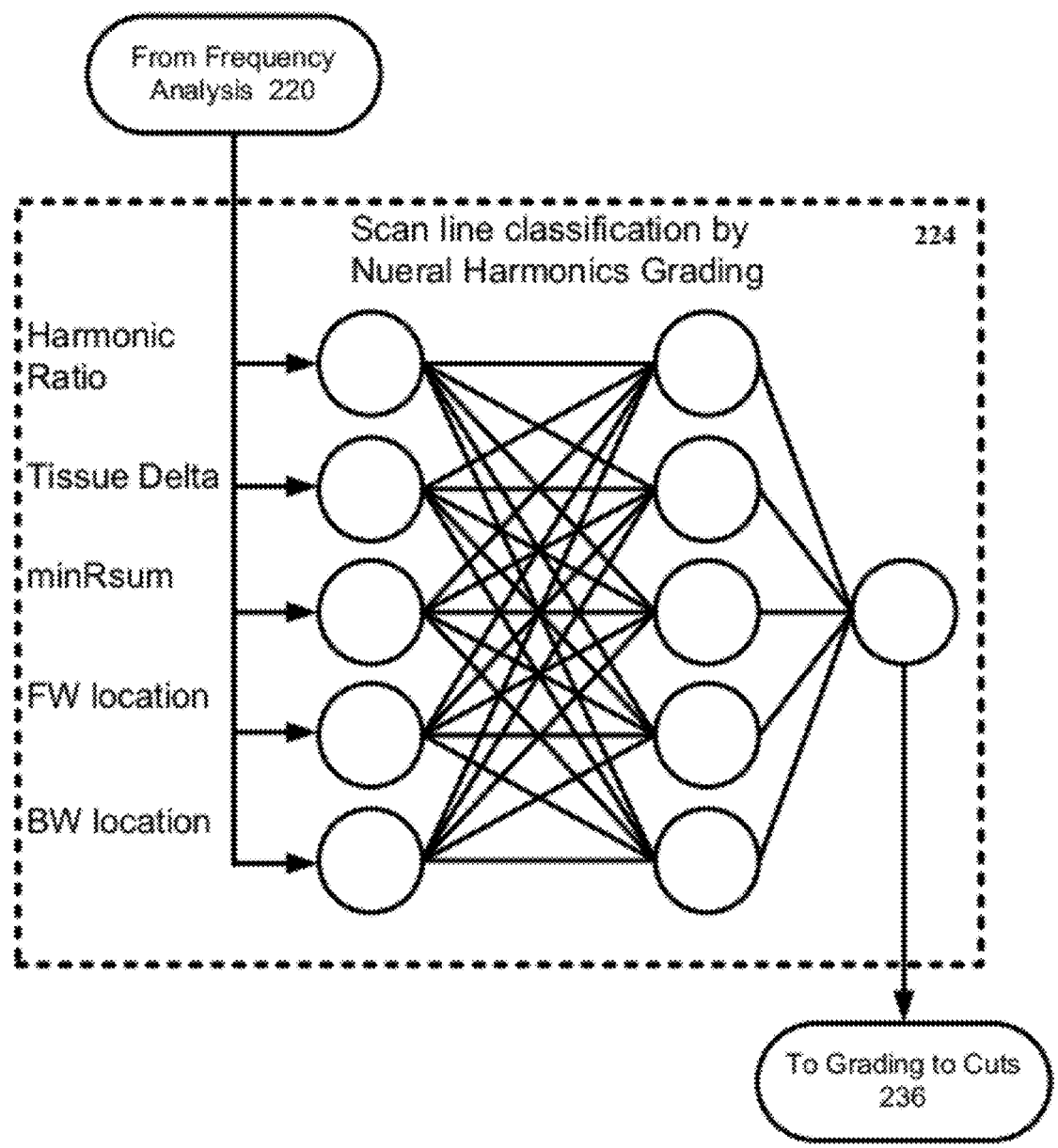

FIG. 9D depicts an expansion of the Neural Network Grading sub-algorithm used for intermediate C-mode shape generation of process block 224 of FIG. 9C. The output of this Neural Network classifier not only helps determine the C-mode shape, but also helps segmentation of the bladder region in each plane and finally it will sharpen the bladder volume measurement. The final C-mode shape generation algorithm 216 is used to draw the C-scan (or C-Mode) view of the bladder. The C-scan geometry is shown in FIG. 2B as scan planes 45 having a substantially square-like ultrasound area within the scan cone 41. The C-Scan image information contained within scan planes 45 presents a cross-section view of the ultrasound at a particular depth probed by the transceiver 10C. In the case of the C-mode is more representative of a portion of the bladder than the actual whole of the bladder. It is more of a binary image showing the lines and spaces that are inside the bladder versus those that are outside of the bladder. FIGS. 23-26 represent various stages of C-mode shape generation algorithm 216. The Neural Network algorithm 224 (NNA 224) is parametric and is used to determine the statistical likelihood that a give scan line passing through a bladder or cavity appearing region does pass through a bladder or cavity. Its weights are all the parameters which are calculated by pre-training. This training is to describe how a classifier learns to make correct classification using preclassified results and corresponding features, which include harmonic ratio at one important feature. Then, a statistical likelihood expressed or termed as line grading represents the output of the NNA 224. The neural network algorithm 224 employs the harmonic analysis kernel described in the appendix and provides a better estimation of scan line grading, prediction, or likelihood that a given scan line is a bladder scan line. The NNA 224 is representative of the workings of cranial neurons where one neuron accepts inputs from millions of other neurons at one layer, then sends an output signal to millions of other neurons and eventually after enough layers of neurons work together to develop a meaningful pattern. The NNA 224 examines parameters that affect its accuracy to perform scan line classification via its predictive functioning. The factors are examined within a Neural Network classifier that predicts how variation in separate factors, or the collective effects of several or all factors that are examined, affect the ability to accurately predict scan line classification, either as a bladder scan line, a non-bladder scan line, and/or a combination bladder and non-bladder scan line.

The NNA 224 represents a summation of the signals (represented by lines) entering a plurality of neural circles from Frequency Analysis process block 220 depicted in FIG. 9C. The neural circles in the first column denote respectively the informational content concerning of harmonic ratios, tissue delta (gradient at front wall and back wall locations), minRsum, front wall location (FW location), and back wall location (BW location). The neural circles on the second column are the hidden units, the number of which can be adjusted. We choose 5 hidden units for this case. Each connection between neural circle is assigned a weight, which is, as mentioned before, based on pre training. The grading or likelihood estimation may be a linear combination of the inputs from process block frequency analysis 220. The relative contributions of the inputs can be varied enough to provide more fidelity in developing a grading system that can be used to make a decision. Spectral estimation algorithms used to provide improved spectral estimation results include parametric and nonparametric. Parametric approaches are more sensitive to data modeling errors and so are incorporated in the NNA 224 to foster accurate organ delineation or organ cavity delineation, for example the bladder, and is based on a sub-aperture processing strategy employing a deconvolution process.

The Neural Network Algorithm 224 combines harmonic features with B-mode image properties. The method is basically a pre-trained 5 by 5 by 1 Neural Network with different features as inputs and a single grading [0-1] as output. For each scan line, after initial walls are estimated based on gradient information, the corresponding features can be computed and the grading value from this network can show how likely the current line is a bladder line. If the grading is low, that means the current line is very likely a tissue line. The initial walls may be wrong or there should be no walls at all. If the grading is high, that means the current line is very likely a bladder line. The initial walls may be correct. The Neural Network algorithm advantageously uses exponential calculation in a logistic function [logistic $(x)=1.0/(1+\exp(-x))$]. In the digital signal processing (DSP), a lookup table is used to give a fast implementation. For more details about the Neural Network training, please refer to the Appendix.

In order to get the exact values for all the weights in the network, a training protocol is incorporated into the system to give correct grading based on different inputs. The training procedure for the NNA 224 includes collecting clinical data on human subjects acquired under B-mode ultrasound procedures. From the collected clinical data, a bladder line known to pass through the bladder region is manually selected, and a non-bladder line known to pass through a non-bladder region is selected. The manually picked bladder line is given a grading or probability of 1, and the manually picked non-bladder line is given a grading or probability of 0. From these known extremes, the NNA 224 generates grading or probability values that a given scan line from the clinical data is a bladder scan line. Then the graded values of all the lines are other features pertaining to the features to train the network using NNA-based Perceptron Learning Rules. Perceptron Learning Rules encompass protocols that allow neural networks to solve classification problems involving weighted sums of a signal matrix so as to ascertain or learn via modification of the weights and biases of a network. In so doing the Perceptron Leaning Rules function as a training algorithm to solve pattern recognition of cavity residing scan lines (i.e., bladder) from the pattern recognition of non-cavity residing scan lines (i.e., non-bladder). The learning algorithms may comprise supervised learning by inputting a set of scan line signal in a training set of output examples, reinforced learning of outputs generated from a set of input scan line signals, or unsupervised learning in which clustering operations are applied to inputted scan line signals. After the training procedure converges, the weights are decided.

Applying the NNA 224 to the harmonic information improves the volume measurement accuracy and help user locate bladder regions faster by optimizing segmentation accuracy of the bladder region. With the harmonic information, the validity of the segmentation or detection of bladder walls on each scan line is determined. The scan line grading from the Neural Network Algorithm 224 provides a more robust and accurate approach to obtain bladder volume calculations.

Figure 9E:
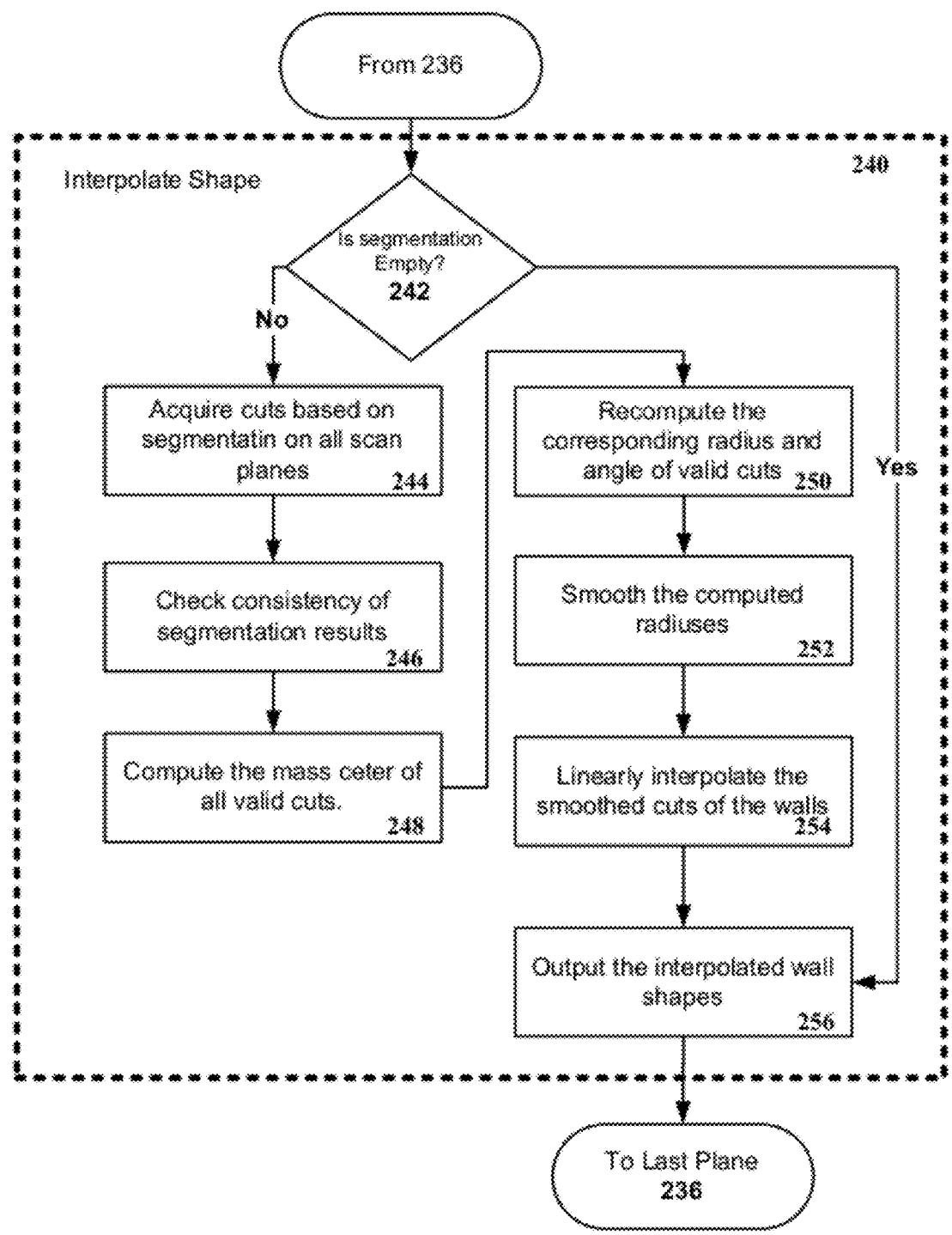

FIG. 9E depicts an expansion of the Interpolate shape sub-algorithm 240 of FIG. 9C. Entering from Grading to Cuts block 236, Interpolate shape 240 begins with seeking answers to the query "Is segmentation empty?" in decision diamond 242. If affirmative, the interpolated shapes are outputted at block 256 and algorithm 250 is completed and returns to Last Plane decision diamond 258 of FIG. 9C. If negative, algorithm 250 routes to process block Re-compute corresponding radius and angle of valid cuts 250, followed by smooth computed radiuses at block 252, then linearly interpolate the smooth wall cuts at block 254, then finally output interpolated shape at block 256 for exiting Interpolate Shape algorithm 240 to return to Last Plane decision diamond 258 of FIG. 9C.

Figure 9F:
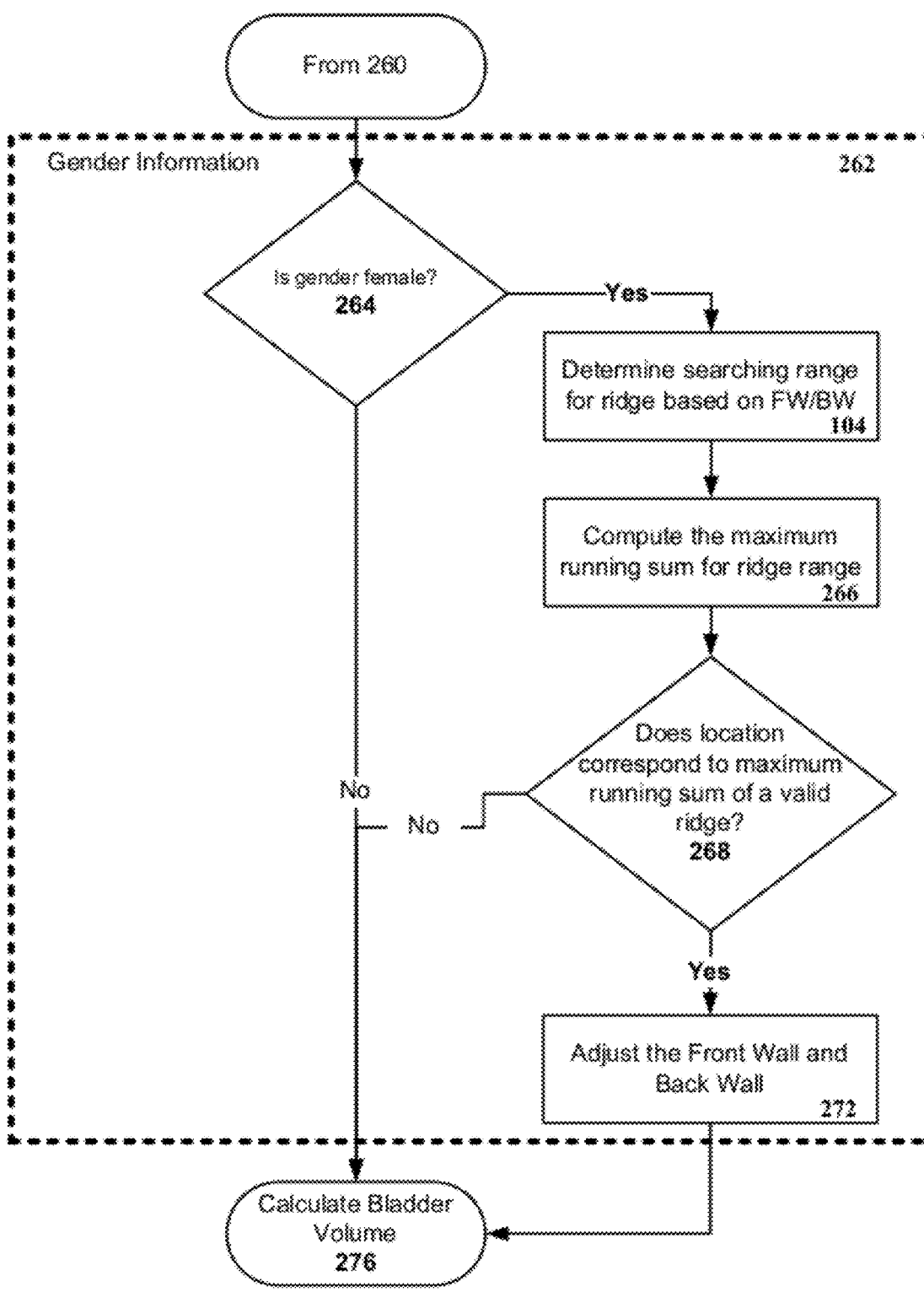

FIG. 9F depicts an expansion of the Gender Information sub-algorithm 262 of FIG. 9C. Entering from Medium filter block 260, Gender information 262 begins with seeking answers to the query "Is gender female?" in decision diamond 264. If negative, algorithm 262 is completed and returns Calculate Bladder Volume 276 of FIG. 9C. If affirmative, algorithm 262 routes to process block Determine Searching Range for Ridge based on Front Wall and Back Wall (FW/BW) intensities at process block 266. Once the ridge is found, at process block 266, the intensities of the ridge are subjected to a computation to determine the maximum running sum for the ridge range. Thereafter, answers are sought to the query "Does FW/BW location correspond to maximum running sum of a valid ridge?" in decision diamond 268. If negative, gender information 262 is completed and exits to calculate bladder volume 276. If affirmative, gender information 262 routes to adjust the front wall and/or the back wall locations at process block 272 to complete gender information 262 and exiting to calculate bladder volume block 276 of FIG. 9C.

Transceivers not having harmonic functionality utilize a BVI3000 algorithm. In the BVI3000 algorithm, the Find-Walls( ) step, which also includes a smoothing step, is run on the A-mode data and leads to candidate front wall and back wall pairs. The MassageWalls( ) and Plane2plane Correlation( ) steps refine the candidate walls, and finally the tissue discrimination step distinguishes between a bladder and a uterus.

The FindWalls( ) process starts with a low pass filter of the data to smooth the data and remove the noise. Next, on each A-mode line the minimum filtered value is determined. After finding the minimum point, the back wall location is then determined using the decision criteria shown in the box and then the front wall location is determined. As a final step, to accept the front wall and the back wall candidate the total energy between front wall and the back wall should be less than a threshold value.

In the tissue discrimination step checks are made to ensure that the uterus is not detected in the scans and that the tissue detected is indeed the bladder. The most significant features that are actually being used for bladder verses uterus determination in this algorithm are the valley mean and detected area on a single plane.

Next, using these initial front walls and back walls, a line passing through the center of the bladder is determined. This center bladder line is used as a seed from which the FixInitialWalls( ) stage of the algorithm starts. This stage of the algorithm is responsible for refining the initial wall points, removing any outliers, and filling any gaps in the wall locations. The next step in the algorithm tries to answer the question of whether the detected region is a bladder or a uterus—this step is executed only when the gender button on the device indicates that the scan is for a female. If the region is indeed found to be a uterus, it is cleared and a zero volume is displayed. For a non-uterus region, if the volume is very small, then checks are made on the size of and signal characteristics inside the detected region to ensure that it is bladder and not another tissue. If a region is indeed a bladder, its volume is computed and displayed on the output.

The BVI6100 algorithm uses several parameters or constant values that are plugged into the algorithm formulas to detect and measurement organ structures and organ cavities. The values of these parameters for the DCD372 and the DCD372A platform are summarized in Table 1:

The parameters used for uterus detection depend on software versions utilized to signal process scan data received from transceivers 10A-B, encompassing its variants that define particular embodiments of the 3000, 6000, and 9000 series, including BVI models 3100, 6400, and 9400. The parameters 372 Value and the 372A Value (in Table 1 below), and the 9400 Value (in Table 2 below) relate to the definition of a plane in geometry is Ax+By+Cz+D=0. Particular values of A, B, C, and D can define a particular plane detected by a given transceiver 10A-B design. The values of the parameters allow tuning the functioning of a given transceiver 10A-B design in acquiring harmonic frequency based imaging data, scan line grading, and the ability to improve segmentation accuracy based on harmonic imaging and to improve uterus detection and exclusion to minimize it masquerading as a bladder.

TABLE 1

Parameters for transceivers series 3100 and 6400:

| Parameter Name | Description | 372A Value | 372 Value |
|---|---|---|---|
| MAXGRAD | Minimum gradient for back wall - Used in Find Initial Walls | 16 | 8 |
| MINGRAD | Maximum gradient for front wall - Used in Find Initial Walls | −10 | −8 |
| WINDOWLENGTH | The length of the smoothing window - Used in Find Initial Walls | 16 | 15 |
| NORMALFACTOR | The normalization factor to shift gradient values - Used in Find Initial Walls | 4 | 4 |
| EDGELINESTOCLEAR | Number of lines at the edges to clear - Used in CleanWalls function. | 0 | 2 |
| MINGRAYLEVEL | Unused. | NA | NA |
| MINDYNAMICRANGE | Unused. | NA | NA |
| DOMEREVERBDEPTHMM | Unused. | NA | NA |
| OVERLAPTHRESHOLD | Unused. | NA | NA |
| WALLDETECTIONLIMIT | Number of samples at start and end of scanline in which bladder cannot exist. | 40 | 20 |
| GRADIENTWINDOWLENGTH | The width of the gradient central difference gradient window. Used in Find Initial Walls. | 3 | Unused |
| MINGRADIENTDELTA | Used towards the end of the algorithm to reject abdominal muscle in small bladders. | 100 | 80 |
| MINBWWIDTH | Minimum backwall thickness in samples - used in Fix Walls - FindBackWall function. | 3 | 3 |
| MINBWINTENSITY | Minimum backwall intensity - used in Fix Walls - | 30 | 16 |

TABLE 1-continued

Parameters for transceivers series 3100 and 6400:

| Parameter Name | Description | 372A Value | 372 Value |
|---|---|---|---|
| MINBLADDERWIDTH | FindBackWall function. Minimum width between fw and bw in samples - used at the end to reject small bladders. | 15 | 8 |
| MAXMINIMUMRUNSUM | The maximum value for the minimum running sum for a FW/BW candidate pair. Used in Find Initial Walls. | 254 | 190 |
| MAX_VOLUME1_UTERUS | The lower limit test for volume to call uterus | 96 | 70 |
| MAX_VOLUME2_UTERUS | The upper limit test for volume to call uterus | 200 | 130 |
| MAX_ENHANCEMENT_UTERUS | The maximum enhancement at the back wall for a uterus. | 44 | 27 |
| MIN_VALLEYMEAN_UTERUS | The minimum valley mean inside the uterus | 17 | 11 |

The algorithms operating within the 9400 transceivers 10A-B utilize harmonic based imaging data and neural network processing illustrated for the NNA 224 in detecting bladders. The BVI9400 describes the segmentation algorithm used in the BVI9400 ultrasound transceiver device equipped with ultrasound harmonic functionality. The BVI9400 is equipped with harmonic analysis functionality to improve segmentation accuracy base on the neural harmonics described below.

In general, BVI3000 and BVI6100 algorithmic methods extract gradient information from fundamental frequency ultrasound echoes returning along scan lines transiting through the bladder region. However, artifacts like reverberations, shadows and etc degrade ultrasound images. Therefore, the corresponding gradient information in B-mode images, in some cases, may be incomplete and lead to inaccurate bladder detection and subsequent measurement. Improving and making more accurate bladder diction and volume measurements by completing incomplete gradient information is achieved by the algorithmic signal processing applied to harmonic frequency ultrasound echoes returning along scan lines transiting though the bladder region. Harmonic analysis provided in the BVI9400 algorithm and device provides a solution. The method is very similar as the FindInitialWalls( ) phase of the BVI6100 algorithm but uses different parameter constant values described in Table 2:

TABLE 2

BVI9400 Parameters. The parameters used for uterus detection depend on software versions utilized to signal process scan data received from transceivers 10A-B.

| | | Value | | |
|---|---|---|---|---|
| Parameter Name | Description | 372A | 372 | 9400 |
| MAXGRAD | Minimum gradient for back wall - Used in Find Initial Walls | 16 | 8 | 10 |
| MINGRAD | Maximum gradient for front wall - Used in Find Initial Walls | −10 | −8 | −8 |
| WINDOWLENGTH | The length of the smoothing window - Used in Find Initial Walls | 16 | 15 | 16 |
| NORMALFACTOR | The normalization factor to shift gradient values - Used in Find Initial Walls | 4 | 4 | 4 |
| EDGELINESTOCLEAR | Number of lines at the edges to clear - Used in CleanWalls function. | 0 | 2 | 0 |
| MINGRAYLEVEL | Unused. | NA | NA | NA |
| MINDYNAMICRANGE | Unused. | NA | NA | NA |
| DOMEREVERBDEPTHMM | Unused. | NA | NA | NA |
| OVERLAPTHRESHOLD | Unused. | NA | NA | NA |
| WALLDETECTIONLIMIT | Number of samples at | 40 | 20 | 40 |

TABLE 2-continued

BVI9400 Parameters. The parameters used for uterus detection depend on software versions utilized to signal process scan data received from transceivers 10A-B.

| Parameter Name | Description | Value 372A | 372 | 9400 |
|---|---|---|---|---|
| | start and end of scanline in which bladder cannot exist. | | | |
| GRADIENTWINDOWLENGTH | The width of the gradient central difference gradient window. Used in Find Initial Walls. | 3 | Unused | 3 |
| MINGRADIENTDELTA | Used towards the end of the algorithm to reject abdominal muscle in small bladders. | 100 | 80 | 100 |
| MINBWWIDTH | Minimum backwall thickness in samples - used in Fix Walls - FindBackWall function. | 3 | 3 | 3 |
| MINBWINTENSITY | Minimum backwall intensity - used in Fix Walls - FindBackWall function. | 30 | 16 | 10 |
| MINBLADDERWIDTH | Minimum width between fw and bw in samples - used at the end to reject small bladders. | 15 | 8 | 15 |
| MAXMINIMUMRUNSUM | The maximum value for the minimum running sum for a FW/BW candidate pair. Used in Find Initial Walls. | 254 | 190 | 175 |
| MAX_VOLUME1_UTERUS | The lower limit test for volume to call uterus | 96 | 70 | NA |
| MAX_VOLUME2_UTERUS | The upper limit test for volume to call uterus | 200 | 130 | NA |
| MAX_ENHANCEMENT_UTERUS | The maximum enhancement at the back wall for a uterus. | 44 | 27 | NA |
| MIN_VALLEYMEAN_UTERUS | The minimum valley mean inside the uterus | 17 | 11 | NA |

Echo signals received from structures in the body carry not only the frequencies of the original transmit pulse, but also include multiples, or harmonics of these frequencies. Echoes from tissue have predominantly linear components, i.e. e. the echo frequencies are the same as the transmit frequencies. These linear components are used in conventional, fundamental B-mode imaging. Harmonic echo frequencies are caused by non-linear effects during the propagation of ultrasound in tissue.

FIG. 10 schematically illustrates sound wave distortion with increasing harmonics. The traditional THI (tissue harmonic imaging) is based on the effect that ultrasound signals are distorted while propagating through tissue with varying acoustic properties. In conventional frequency-based 2nd Harmonic Imaging, the received frequencies are selected to be twice the transmit frequencies. In contrast, the disclosure applicable to the harmonic transceiver embodiments utilizes substantially different methods to obtain harmonic information. The harmonic methods quantify the harmonic change along each RF line as harmonic ratio and we use this ratio to distinguish the media the RF line passes through. This process is made in the frequency domain.

Harmonic information provides improved image depth information that otherwise would remain hidden in the fundamental frequency domain. The harmonic information provides an effective indicator for harmonic build-up on each scan line at different depth, based on which, bladder lines and tissue lines can be separated. However, inside bladder region, there is not enough reflection. Deep behind the bladder wall, harmonic can be attenuated fast. Then, harmonic information can be most abundant behind the back wall of the bladder. So, the harmonic information around the back wall location, instead using the RF data at a fixed range, is discussed in greater detail.

Quantification of the Harmonic Information

Figure 11:
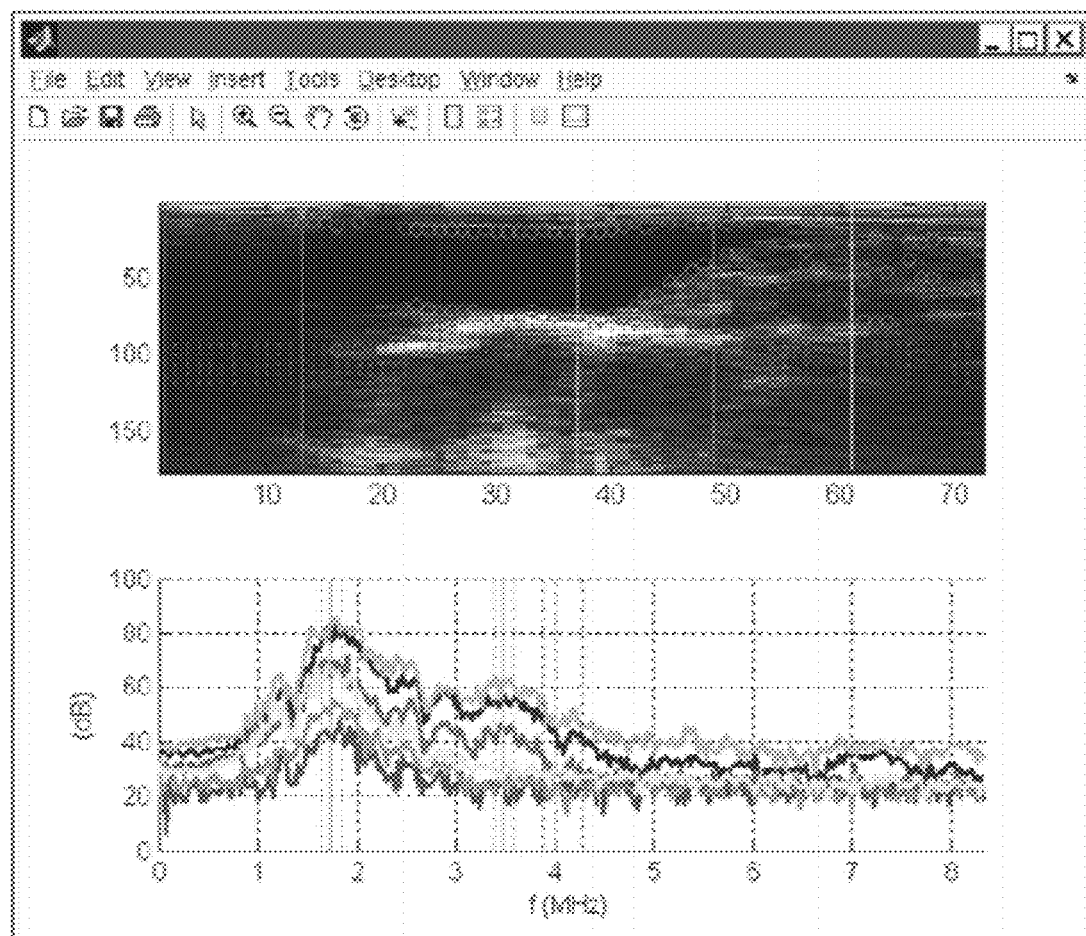
FIG. 11 illustrates frequency spectra of 6 RF lines from a human subjects, from which, the difference between the $2^{nd}$ harmonic and the fundamental can be found.

FIG. 11 illustrates a frequency analysis of an RF2 harmonic that presents a challenge to effectively quantify in tissues more distant from the transceivers 10A-B-C. As illustrated, there are 6 different scan lines. The frequency response is at different levels basically and it is hard to be compared to each other. The different levels are because the different scan lines are through different path with different materials. [The dot lines in red are the windows defined by back location for harmonic analysis. Red circles are the initial wall locations.]

Figure 12:
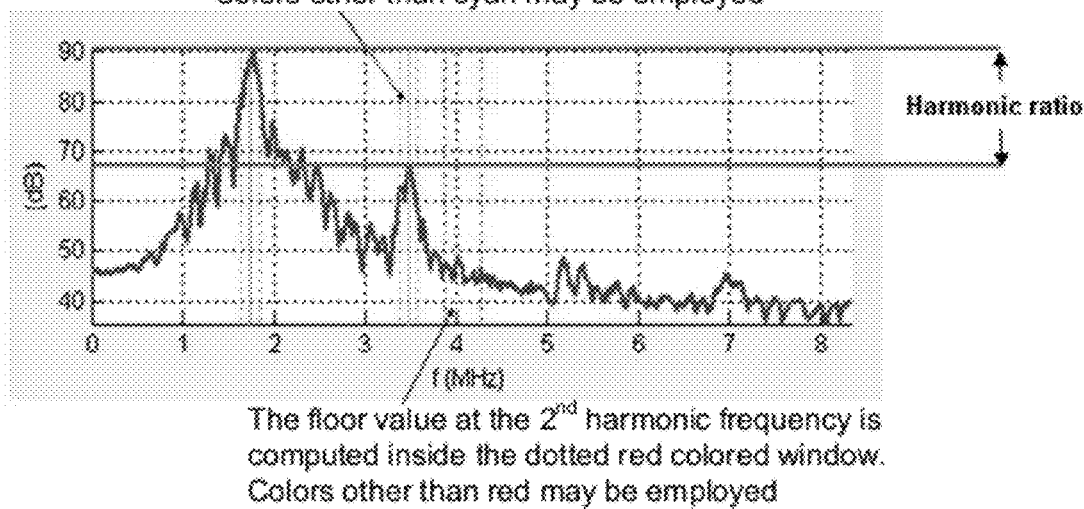
FIG. 12 illustrates a frequency spectra example on how a quantification of harmonic information is made via harmonic ratio.

FIG. 12 illustrates a frequency spectra example on how a quantification of harmonic information is made via harmonic ratio. One way to use the harmonic information is to see relative change of the harmonic information around the 2nd harmonic frequency compared with response at fundamental frequency. The ratio of the peak value around the $2^{nd}$ harmonic and the peak value around the fundamental frequency is a suitable indicator for such change.

Figure 13:
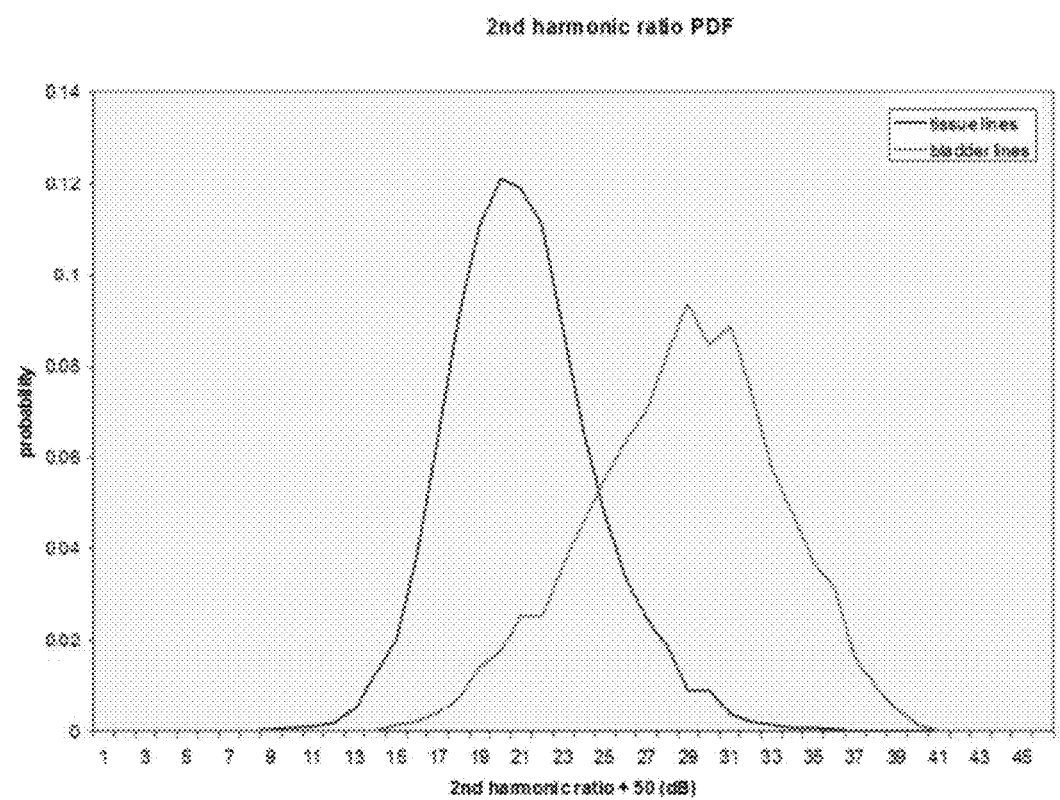
FIG. 13 illustrates a second harmonic ratio distribution.

FIG. 13 illustrates second harmonic ratio distributions corresponding to two types of scan lines, bladder lines and tissue lines. The distributions are based on real clinical data sets. We manually graded all the scan lines in data sets collected from 01-05-2007, including 12 males and 1 female. The data sets include pre-void and post-void cases. Totally, there are 20736 scan lines. (8250 for bladder lines, 12486 for tissue lines). We use the manual grading as the ground truth for two different groups of scan lines, bladder lines and tissue lines. We computed the probability density functions (PDF) corresponding to these two different groups of scan lines Examples of how scan lines are graded as to likelihood of residing within or separate from a cavity is described by returning to a more explanation of the neural network algorithm 224 (NNA 224) for scan line grading depicted in FIG. 9D. The neural network algorithm employs a harmonic analysis kernel described in the appendix and provides a better estimation of scan line grading, prediction, or likelihood that a given scan line is a bladder scan line.

Applying the NNA 224 to the harmonic information improves the volume measurement accuracy and help user locate bladder regions faster by optimizing segmentation accuracy of the bladder region. With the harmonic information, the validity of the segmentation or detection of bladder walls on each scan line is determined. The grading from the Neural Network Algorithm 224 provides more robust information to fix the initial bladder walls.

How the validity of the segmentation that a given scan line is validly declared a bladder scan line is determined by categorizing the width of scan lines into G and W groups and performing a G & W analysis. Each G or W group defines a width of G and W can be up to the number of lines of ultrasounds in a plane. G represents lines where the neural network grading (including harmonic analysis) indicated the presence of a bladder. W represents the set of lines identified as passing through the bladder based on the original algorithm that's been in use in several generations of devices. The two sets G and W are combined in a way to result in the final set of lines for which the bladder is likely to exist. The final set must include all lines in G if G overlaps W and no lines in W that do not overlap with G.

An example of the G and W analysis procedure utilizing the harmonic derived grading value includes arranging the G and W lines to make it easier to remove the wrong segmentation line and make it more difficult to add new lines by averaging the non-zero initial wall on current line and the non-zero fixed wall from its neighboring line. This is achieved by adding to the new bladder walls with the large grading values to the nearest valid initial bladder wall pair. Thereafter a region G is defined in which all lines having a grading value higher than the threshold value. To remove the bladder walls having a too small grading value, a region W is defined which is based on the cuts, or the validly segmented regions, obtained from the fixed walls algorithm. Thus for region G and region W, there can be five different cases to consider:

| Case 1. | G and W are not overlapped (including empty G or empty W): remove both |
|---|---|
| G |  |
| W | |
| Case 2. | G inside W: remove the walls in W, while not in G |
| G | |
| W | 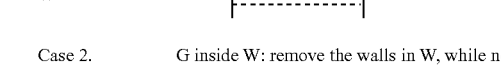 |
| Case 3. | W inside G: add the walls outside W, while in G |
| G | |
| W | 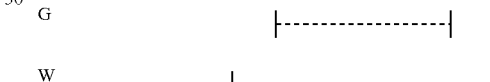 |
| Case 4. | G and W are partly overlapped: remove and add |
| G | |
| W | 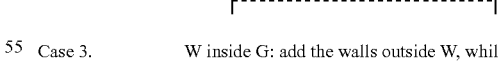 |

| | |
|---|---|
| Case 5. | G and W are exactly the same: do nothing |
| G | ├--------------┤ |
| W | ├--------------┤ |

Figure 14A:
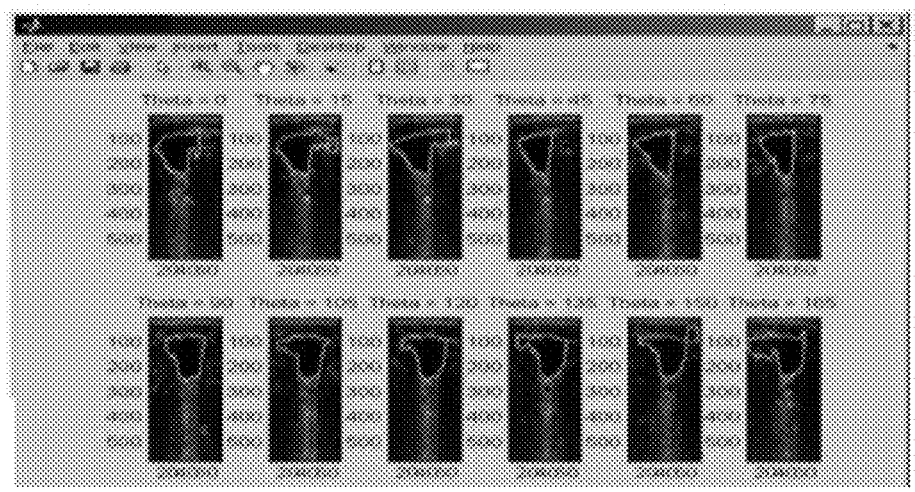
FIG. 14A illustrates clinical cases of bladder overestimation arising from the use of non-harmonic information.
Figure 14B:
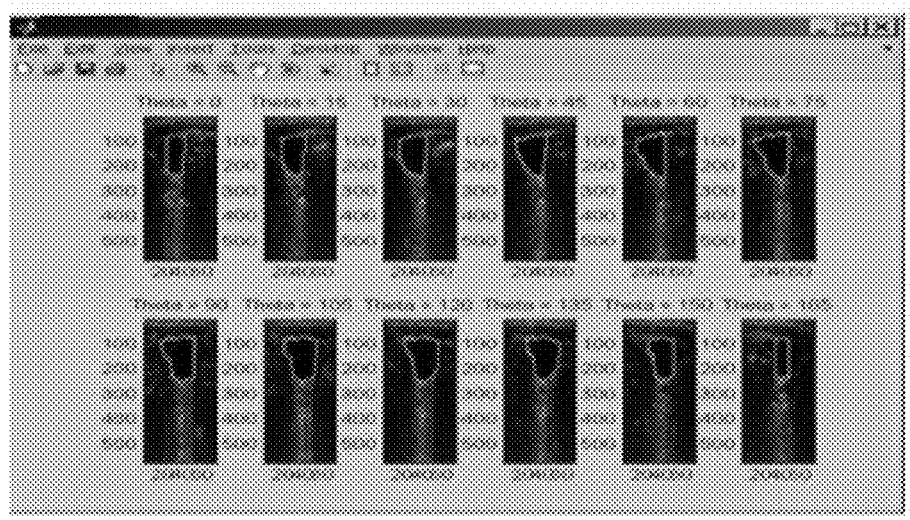
FIG. 14B illustrates scan line grading to correct for over-estimation of segmented bladder cavity interfaces.

FIGS. 14A-14B illustrate differences in bladder wall segmentations as computed and outlined in light peripheral boundary lines.

FIG. 14A illustrates clinical cases of bladder overestimation arising from the use of non-harmonic information. Bladder volume accuracy using non-harmonic information is less as using harmonic method as described for FIG. 9C. In FIG. 14A, a panel of twelve sonograms having different inter-scan plane θ values in 15 degree increments between 0 and 165 degrees show examples of bladder overestimation due to non-optimal placement of boundary lines along the bladder cavity and tissue interface. The overestimation is the result using original wall fixing method, without utilizing the harmonic information and neural network grading. The computed result from this segmentation is approximately 145 ml pre-void from a bladder previously measured to have a post-void volume of 15 ml. Thus the expected value less the post-void volume is approximately 130 ml. The urine flow measured was 85 ml, or an overestimation of 45 ml.

FIG. 14B illustrates scan line grading to correct for overestimation of segmented bladder cavity interfaces. The result is based using harmonic ratio and neural network grading for fixing. In this set the computed total bladder volume is approximately 90 ml pre-void, from the bladder determined to have a 3 ml post-void volume. Thus the computed urine volume is approximately 87 ml, for a 2 ml overestimation. With utilization of the harmonic information and neural network grading, there was a 43 ml (>90%) reduction in the overestimated computed value.

Figure 15A:
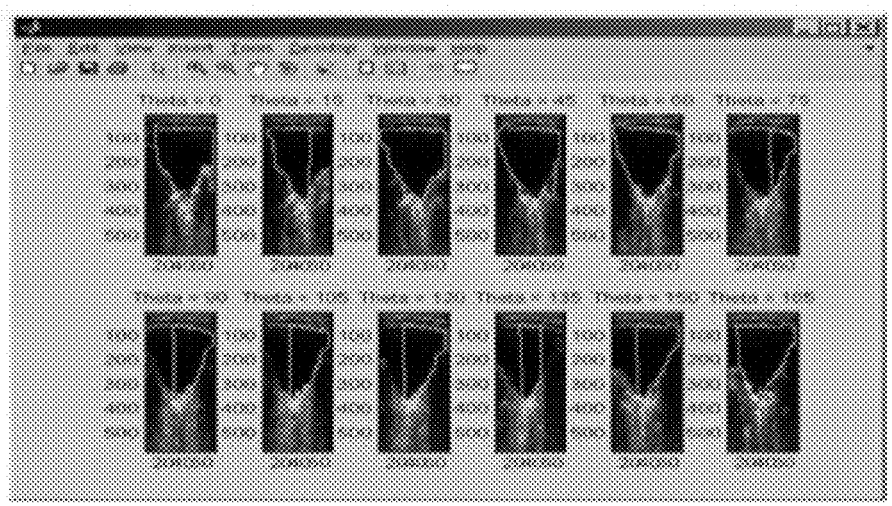
FIG. 15A illustrates clinical cases of under-estimation of segmented bladder cavity interfaces.

FIG. 15A illustrates scan line grading to correct for underestimation of segmented bladder cavity interfaces. A panel of twelve sonograms having different inter-scan plane θ values in 15 degree increments between 0 and 165 degrees show examples of bladder overestimation due to non-optimal placement of boundary lines along the bladder cavity and tissue interface. The overestimation is the result using original wall fixing method, without utilizing the harmonic information and neural network grading. The computed result from this segmentation is approximately 472 ml pre-void from a bladder previously measured to have a post-void volume of 163 ml. Thus the expected value less the post-void volume is approximately 309 ml. The urine flow measured was 520 ml, or an overestimation of 211 ml.

Figure 15B:
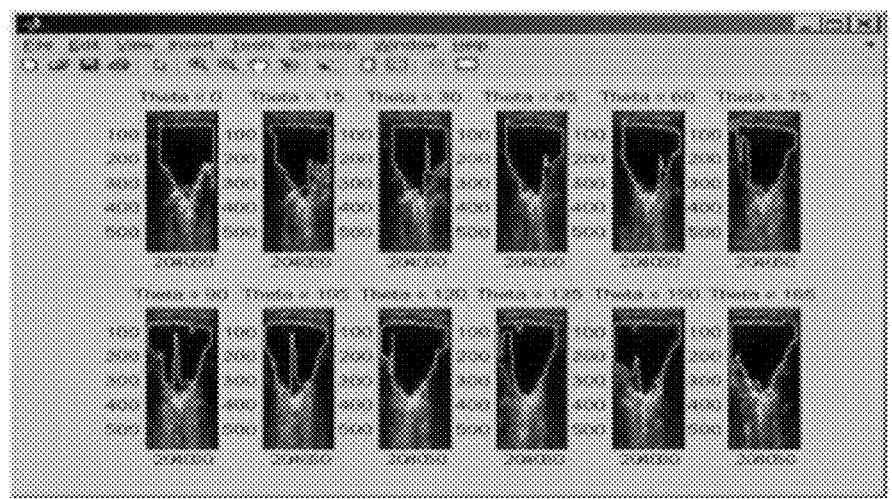
FIG. 15B illustrates scan line grading to correct for under-estimation of segmented bladder cavity interfaces.

FIG. 15B illustrates scan line grading to correct for underestimation of segmented bladder cavity interfaces. The result is based using harmonic ratio and neural network grading for fixing. Here the computed total bladder volume is approximately 658 ml pre-void, from the bladder determined to have a 159 ml post-void volume. Thus the computed urine volume is approximately 499 ml, for a 21 ml overestimation. With utilization of the harmonic information and neural network grading, there was a 190 ml (~90%) reduction in the overestimated computed value.

Figure 16:
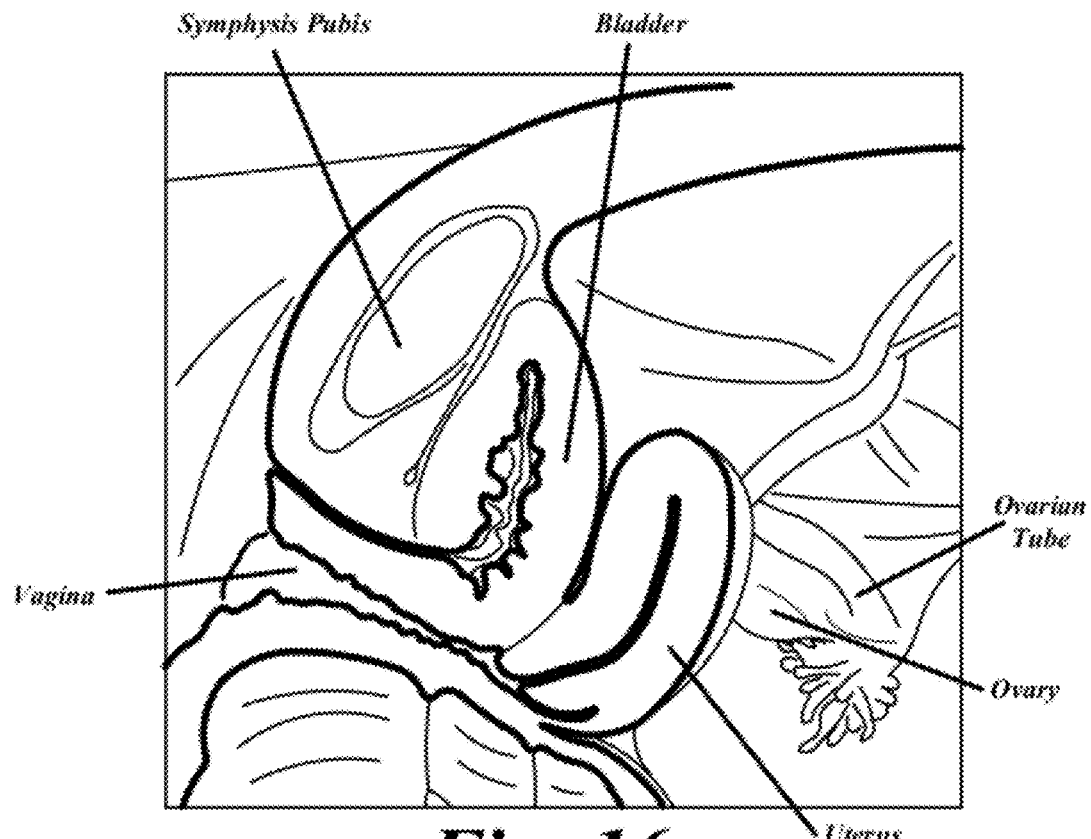
FIG. 16 illustrates a depiction of the anatomical locations of uterus and bladder and other anatomical structures.

FIG. 16 illustrates a depiction of the anatomical locations of uterus and bladder and other anatomical structures. Other non-bladder structures include the Symphysis Pubis, the ovary, and ovarian tube.

Figure 17:
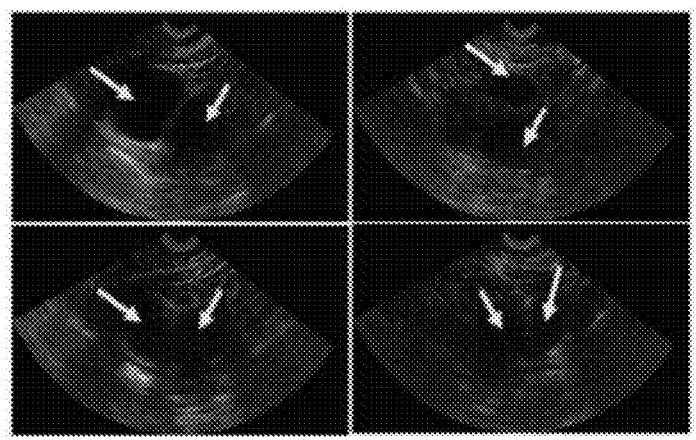
FIG. 17 presents a 4-panel scan image set of ultrasound scanned female patients, where the uterus is adjacent to the bladder region and it has very similar pattern in B-mode image.

FIG. 17 presents a 4-panel scan image set of ultrasound scanned female patients. Bladder detection task is more challenging for female patient due to the presence of uterus. In general, the uterus is adjacent to the bladder region and it has very similar pattern in B-mode image. It is optionally advantageous to exclude the uterus region from the final segmentation. Therefore, the computed volume is the actual urine inside the bladder. Previously, a uterus detection method is proposed in FIG. 8 for the 6x00 ultrasound transceiver product series. This method is dealing with the whole segmentation after wall detection using volume. In another words, the segmentation is bladder or uterus. However, some times, it is not so simple to refine the result, because the segmentation includes both bladder and uterus. The more reasonable and accurate way to solve the problem is to tell which part in the segmentation belongs to bladder and which part in the segmentation is uterus. The difficulty in determining which part of the segmentation belongs to a bladder or uterus is compounded when the bladder is a small size.

The uterus can be located side by side with the bladder and it can also be located under the bladder. For the first case, the method we proposed in previous section can be used to classify the scan lines passing through uterus only from the scan lines passing through bladder. However, the method could not solve the second problem. When a scan line is propagating through both bladder region and uterus region, further processing has to be made to find which part on the line belongs to bladder. In the following, we design a new method for excluding uterus from the final segmentation based on gender information.

Figure 18:
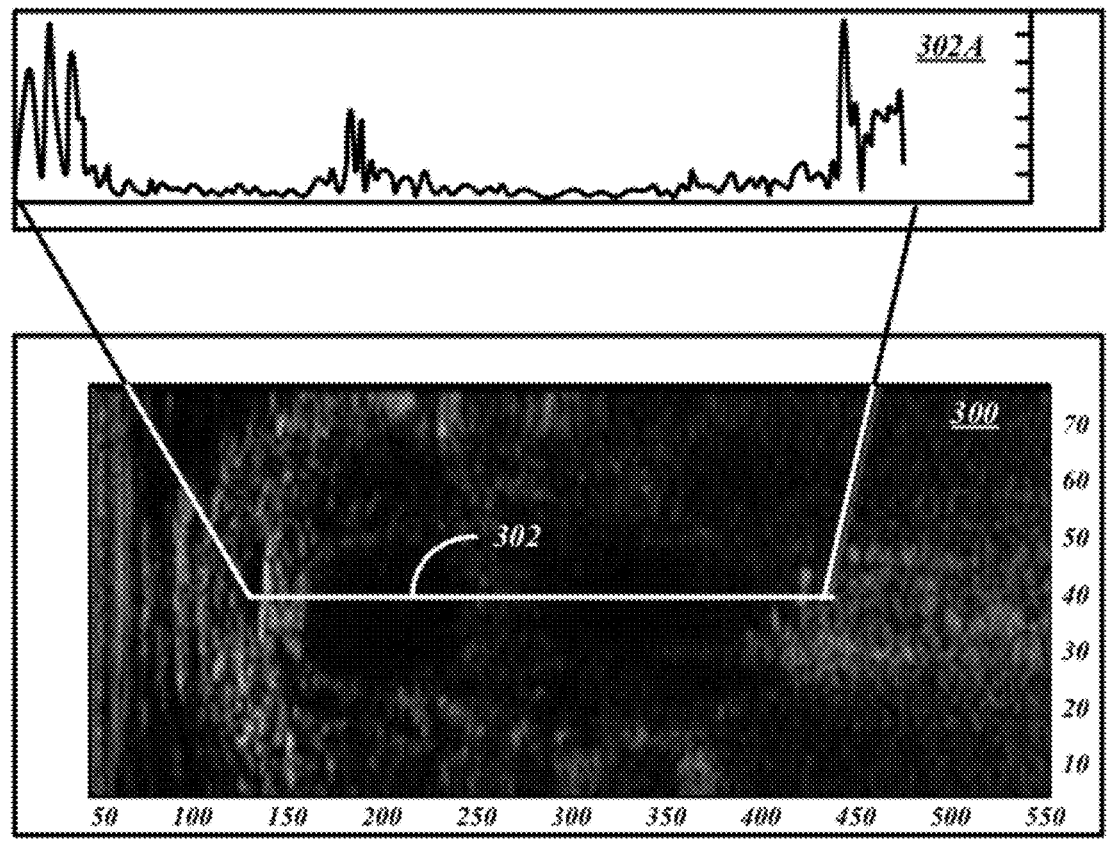
FIG. 18 illustrates one example on how to distinguish the bladder region from the uterus along scan line; If the scan is on a female patient, there must be a boundary between uterus and bladder region and the uterus is always under the bladder if both regions appear on a scan line. In the B-mode image, for each scan line passing through both regions, a small ridge exists. If the ridge can be found, we can tell them apart. So, by using gender information, the algorithm is able to refine the segmentation by separate the bladder region from uterus region.

FIG. 18 illustrates one example on how to distinguish the bladder region from the uterus along scan line. If the scan is on a female patient (gender information provided by user), a boundary between uterus and bladder region is observable and the uterus presents itself under the bladder if both regions appear on a scan line. In the B-mode image, for each scan line passing through both regions, a small ridge exists. If the ridge can be found, then both regions can be discerned. The uterus is under the bladder if both regions appear on a scan line. In this B-mode image, each scan line 302 passes through both regions having a small ridge. If the ridge can be found, discernment of it allows delineation of the bladder from the uterus. As shown in FIG. 18, an observable ridge in the echo histogram 302A derived from scan line 302 is seen between the bladder and uterus of the female patient. This ridge finding procedure can be executed on initial walls or the final walls.

Figure 19:
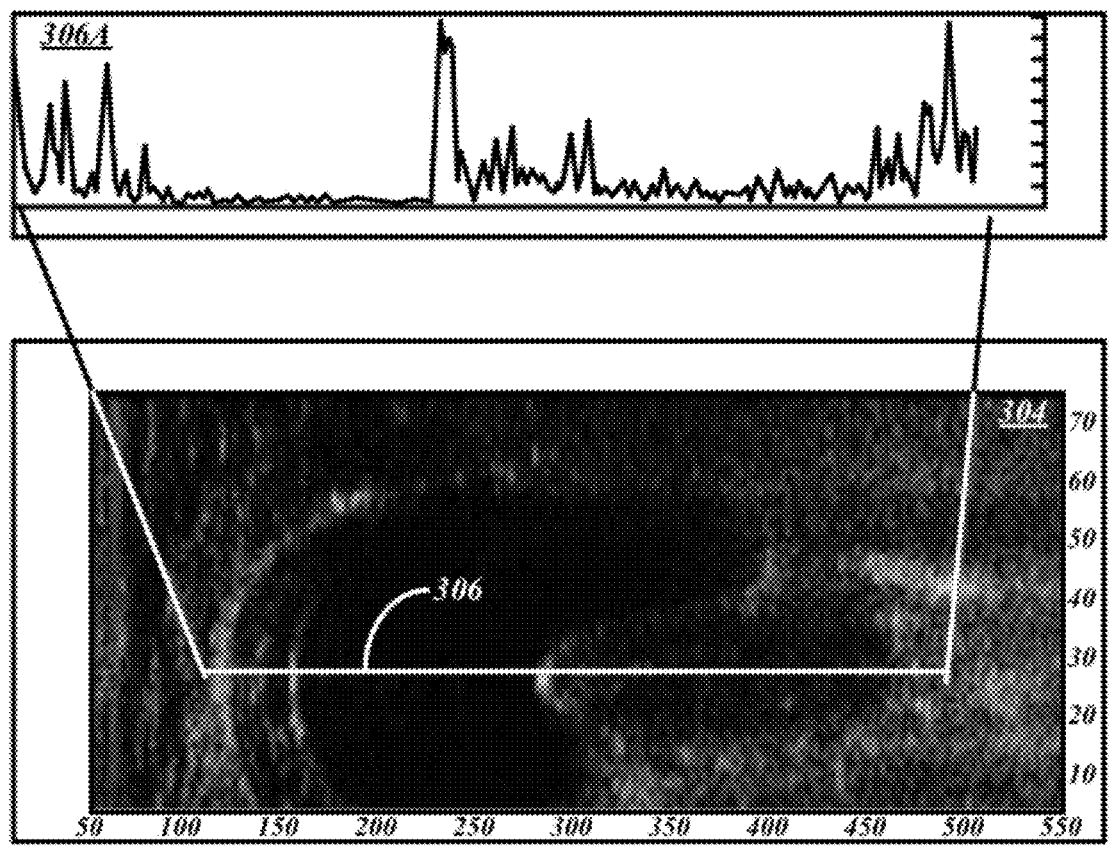
FIG. 19 illustrates another example on how to distinguish the bladder region from the uterus along scan line.

FIG. 19 illustrates another example on how to distinguish the bladder region from the uterus along scan line. In this B-mode image, each scan line 306 passes through both regions, having a small ridge between the two regions. If the ridge can be found, discernment of it allows delineation of the bladder from the uterus. As shown in FIG. 19, an observable ridge in the echo histogram 306A derived from scan line 306 is seen between the bladder and uterus of the female patient.

Figure 20:
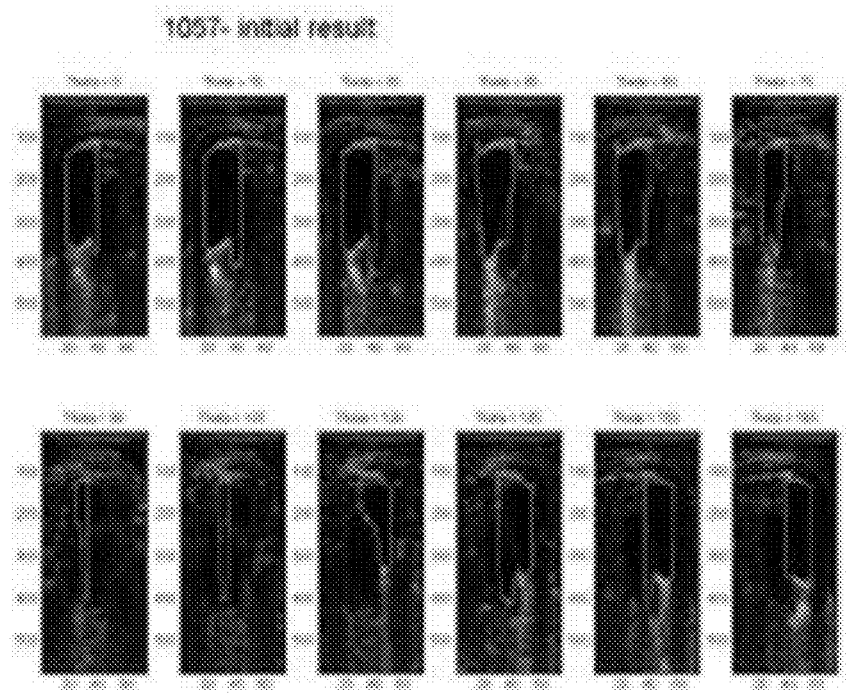
FIGS. 20 and 21 presents a series of bladder scan segmentations resulting without using the gender information.
Figure 21:
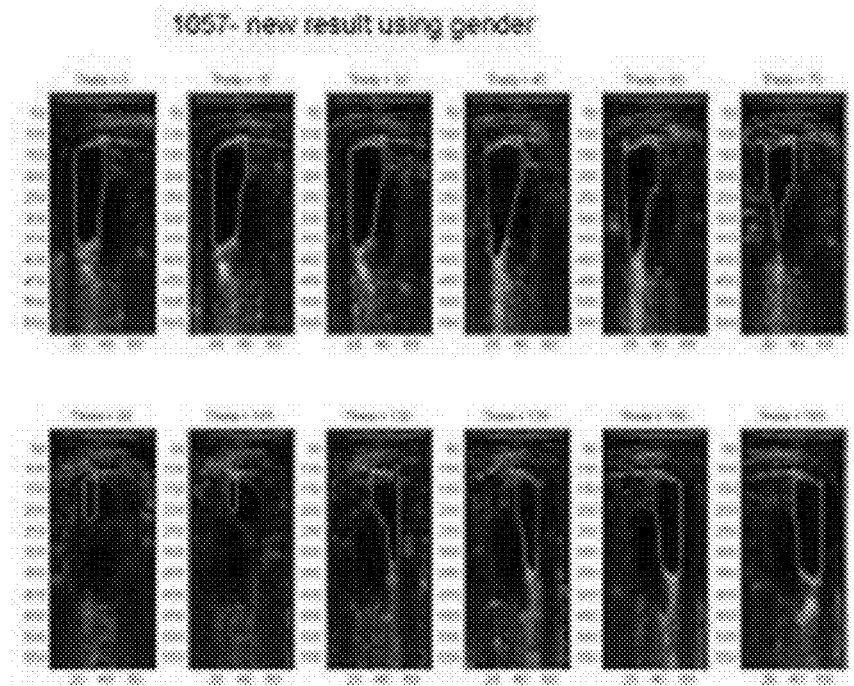

FIGS. 20 and 21 presents a series of bladder scan segmentations resulting without using the gender information.

Figure 22:
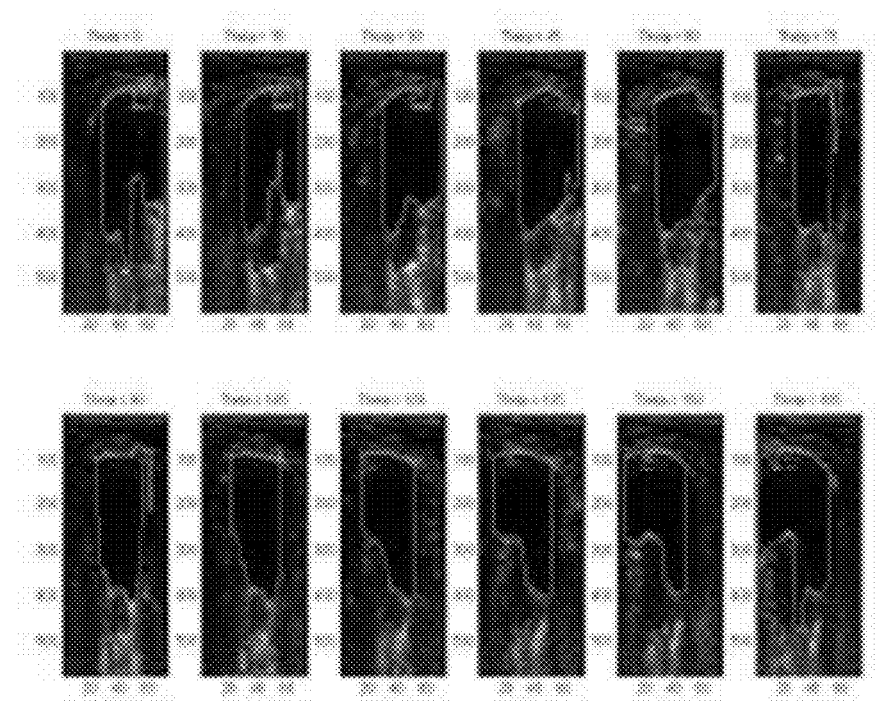
FIGS. 22 and 23 presents a series of bladder scan segmentations resulting using the gender information.
Figure 23:
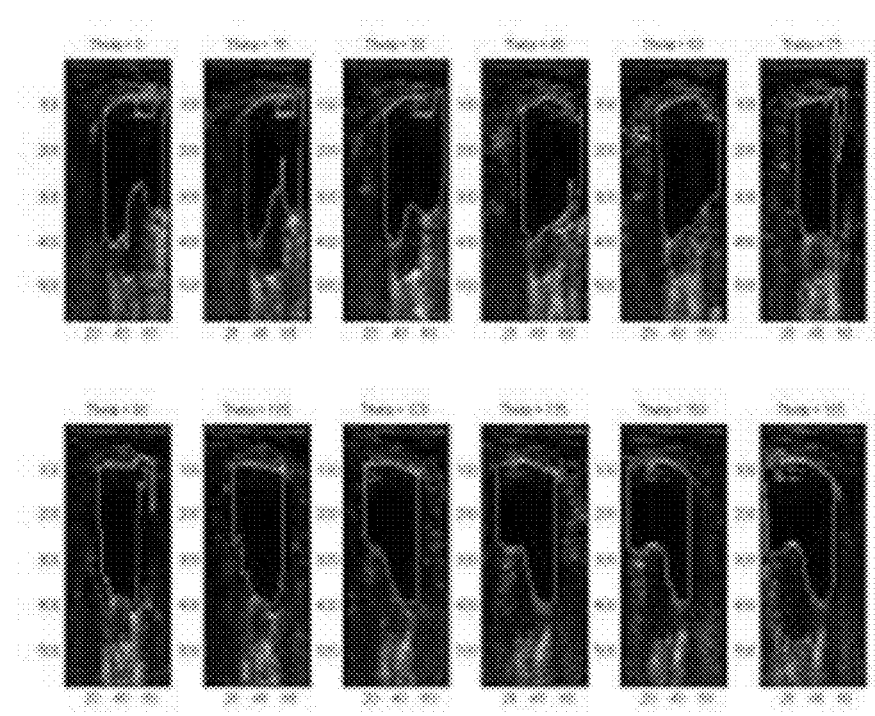

FIGS. 22 and 23 presents a series of bladder scan segmentations resulting using the gender information. After using the gender information, the incorrectly segmentation can be modified.

Figure 24:
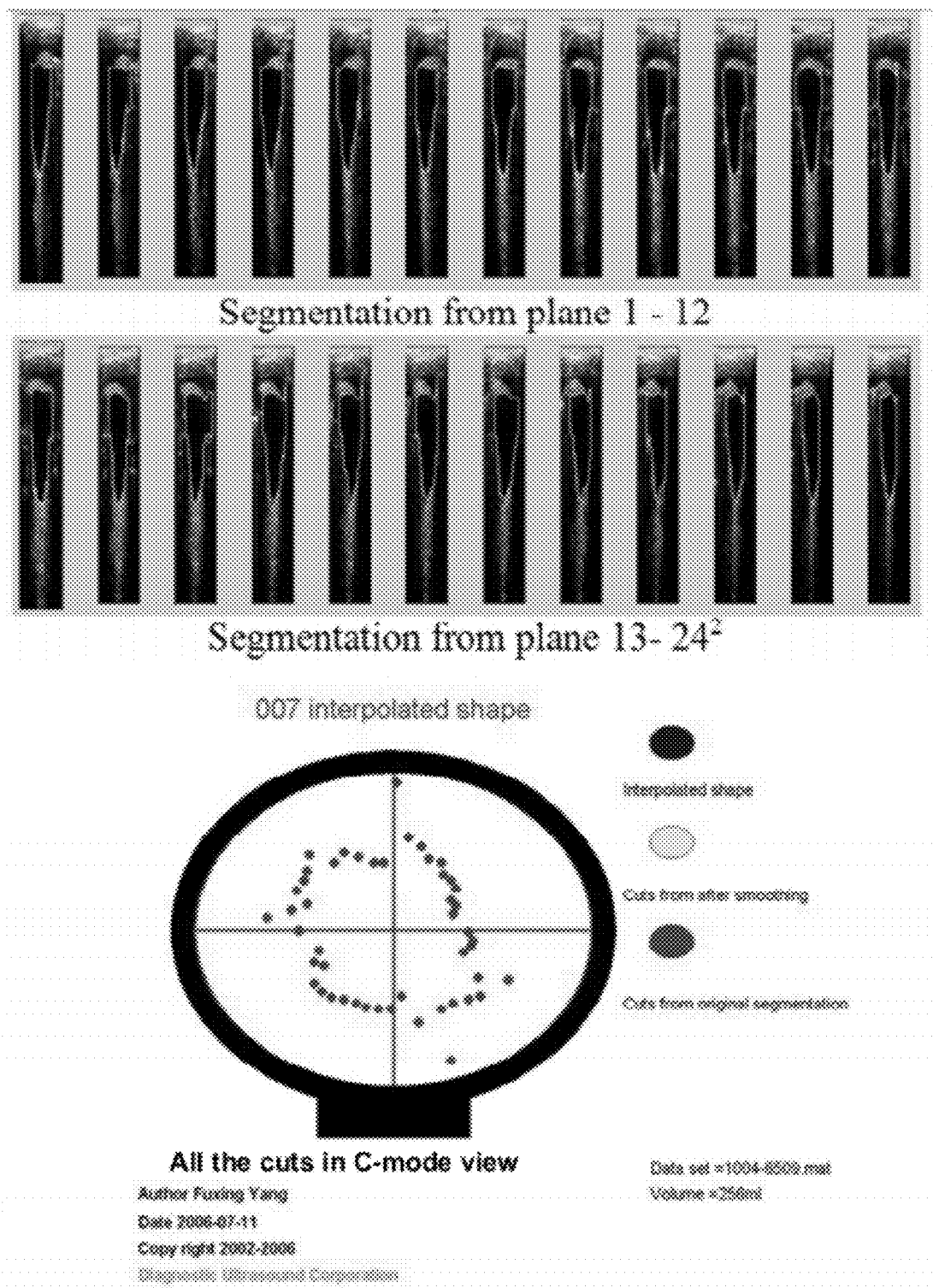
FIG. 24 presents segmentations presented in polar coordinate form of planes 1-12 and 13-24, with a diagrammatic presentation of the interpolated shapes presented in an all the cuts of a C-mode acquired view.

FIG. 24 presents segmentations presented in polar coordinate form of planes 1-12 and 13-24, with a diagrammatic presentation of the interpolated shapes presented in an all the cuts of a C-mode acquired view. The left most and right most cuts are extracted for the cuts based on segmentation on all planes. The diagrammatic presentation, in color codes, illustrates the interpolated shape, the cuts from after smoothing, and the cuts from the original segmentation. Here the volume of the bladder was estimated to be 256 ml.

FIG. 25 presents a 3-D plot of an inconsistency case (upper plot) and a consistency case (lower plot) as a means to check the consistency of the segmentation results. The inconsistency case arises from an abnormal case for bladder segmentation where more than one connected regions are based on the segmentation on all planes. The consistency case reflects a normal case for bladder segmentation, where only one connected region is based on the segmentation on all planes. Theoretically, bladder in the Bladder scan is a single connected 3D volume. Due to different reasons (One optionally advantageous reason is the segmentation algorithm searches for bladder wall blindly plane by plane.), there may be more than one 3D regions and the corresponding bladder walls are also stored in the segmentation results. This step can make a topological consistency checking to guarantee that there is only one connected region in the C-mode view/

FIG. 26 illustrates interpolated shapes before smoothing (top diagram) and after smoothing based on the mass center (bottom diagram). Compute the mass center of all the valid cuts. Re-compute the corresponding radius and angle of every valid cut. Then smooth the radius.

The Cartesian coordinates are computed for each valid cut and get the mass center. Based on this mass center, compute the corresponding radius and angle of very valid cut. Sort the new angles in ascending order. At the same time align the corresponding radius. In order to smooth the final interpolated shape, we average the radiuses from above result in a pre-defined neighborhood FIG. 27 illustrates the output of interpolated shapes between smoothed cuts before smoothing (top diagram) without interpolation and after linear interpolation (bottom diagram). Output the walls of the interpolated shape.

Figure 28:
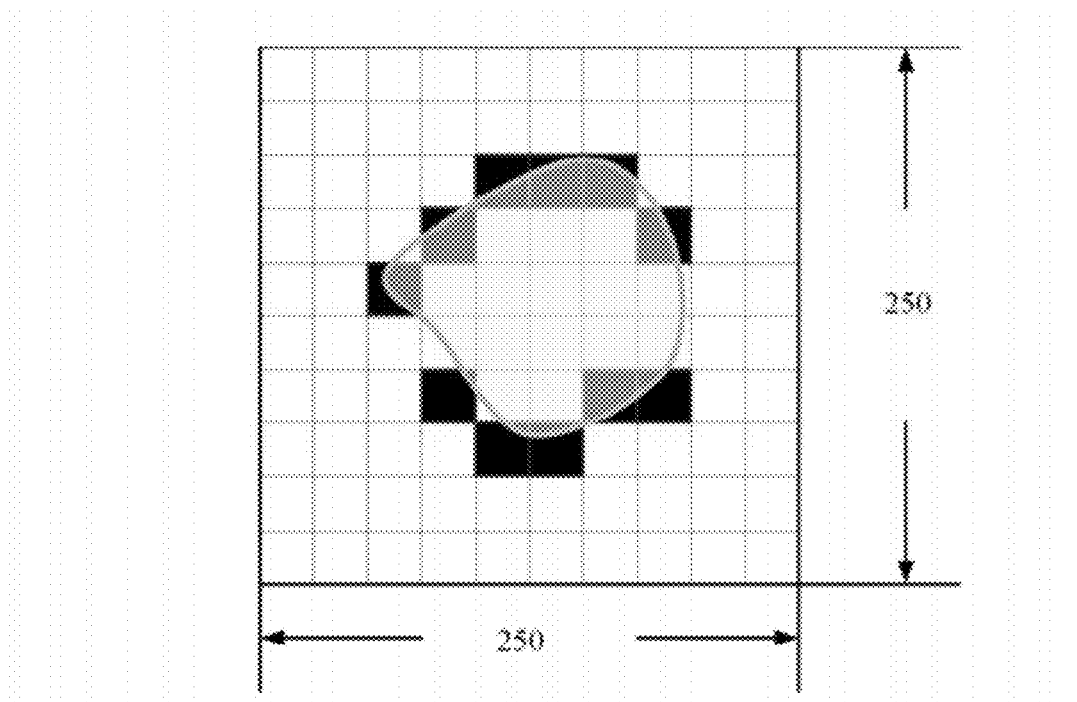
FIG. 28 illustrates a representation of two walls for the interpolated shape.

FIG. 28 illustrates a representation of two walls for the interpolated shape. The final output which is used to represent the interpolated shape is stored in two arrays, the size of which is 250. The dimension of the final display is on a 2D matrix, 250 by 250. The two arrays store the upper wall and lower wall location in each column respectively.

Figure 29:
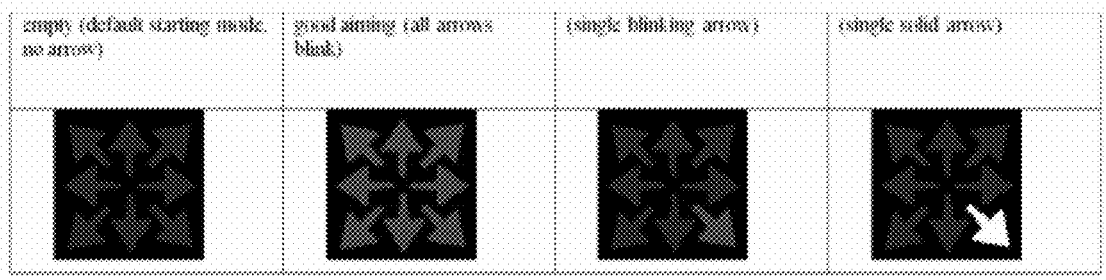
FIG. 29 showing the different arrow feedback modes of the aiming indicator 22 of transceivers 10A-B-C.

FIG. 29 showing the different arrow feedback modes of the aiming indicator 22 of transceivers 10A-B-C. The aiming indicator 22 depicted in FIG. 1A functions equivalently as the targeting icon screenshot 77B depicted in FIG. 2C in aiding or guiding a transceiver user to position the transceivers 10A-B-C to obtain a centered image of the bladder or other cavity-containing organ. The C-mode view of the interpolated shape. An optionally advantageous application is to provide guidance for the users find the best scanning location and angle. This task is called aiming. Basically, the aiming is based on the segmentation results and it is similar as the C-mode shape functionality. There are two kinds of aiming information, arrow on the probe and the intermediate shapes: Arrow feedback—Use extra displaying panel on the scanner, 9400 also provides arrow feedback after a full scan. The error feedback is totally based on the C-mode view shape. There are totally 4 different arrow feedback modes. Eight arrows may be used. Which arrow should be used is determined by the location of the mass center of the interpolated shape in C-mode view. Based on the vector between ultrasound cone center and the mass center, the corresponding angle can be computed in a range from −180 degree to +180 degree. The [−180 180] range is divide into 8 parts and each part is corresponding to each arrow.

Figure 30:
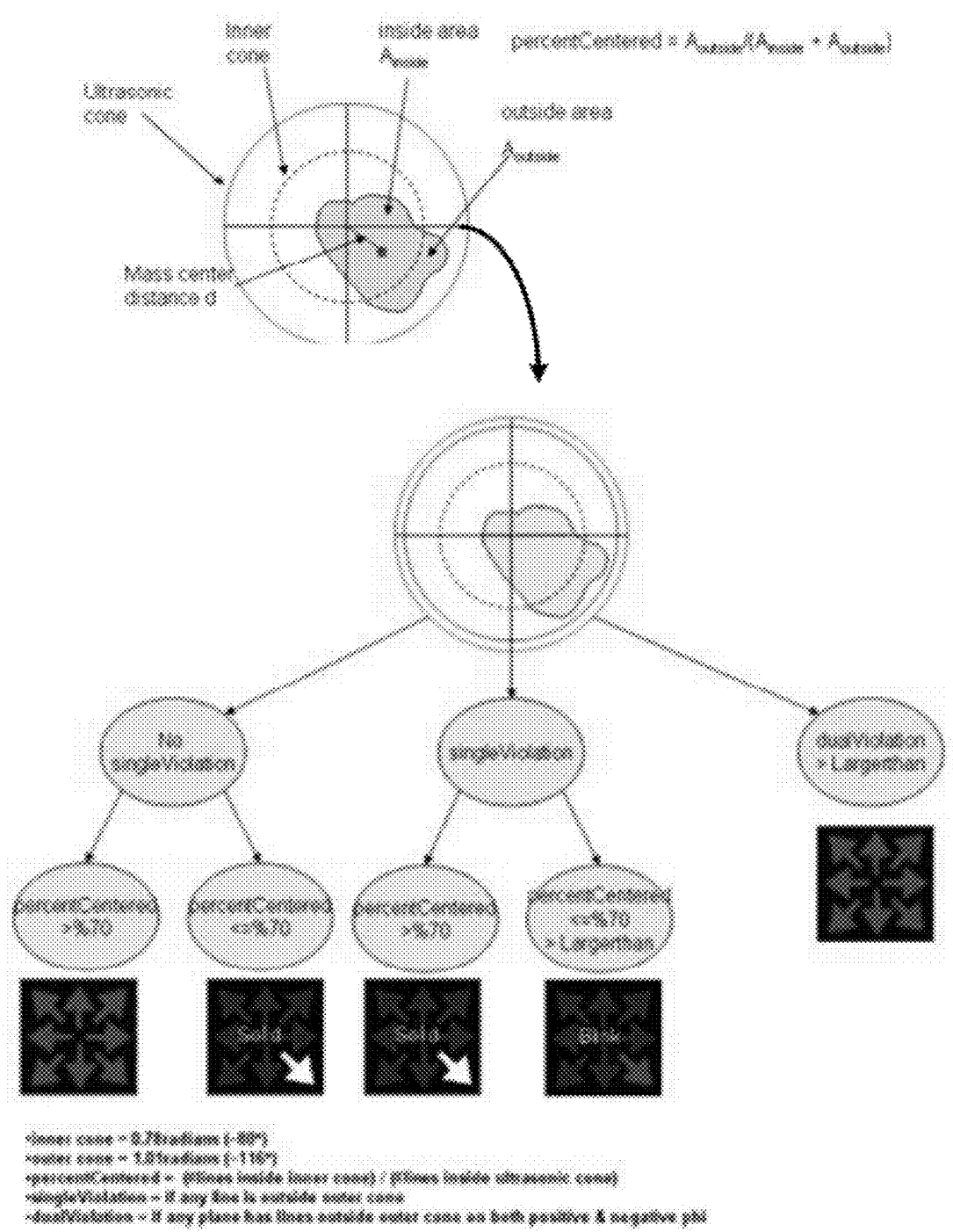
FIG. 30 illustrates a decision tree for the arrow feed back from the indicator 22.

FIG. 30 illustrates a decision tree for the arrow feed back from the indicator 22. This tree describes how the program determines to show flashing arrow or solid arrow on the indicator panel. Here are the descriptions of all parameters we defined in this tree:

inner cone=0.78 radians (~80 degree)
outer cone=1.01 radians (~116 degree)
percentCentered=(Mines inside inner cone)/(Mines inside ultrasonic cone)
singleViolation=if any line is outside outer cone
dualViolation=if any plane has lines outside outer cone on both positive & negative phi.

The procedure to determine the arrow displaying can be described as following:

Compute the mass center of the C-mode shape
Calculate the direction based on the mass center location
Check if there is singleViolation (any line is outside outer cone), dualViolation (if any plane has lines outside outer cone on both positive & negative phi) or no singleViolation (all lines are inside outer cone)
Calculate percentCentered and compare it with the 70% threshold to finally determine arrow type if there is no singleViolation or singleViolation.

As relating to pubic bone detection, arrow feedback provides accurate aiming feedback information, the shadow caused by pubic bone should also be considered. In the ultrasound image, the only feature associated with the pubic bone is the big and deep shadow. If the shadow is far from the bladder region we are interested in for volume calculation, there is no need to use this information. However, if the shadow is too close to the bladder region, or the bladder is partly inside the shadow caused by pubic bone, the corresponding volume can be greatly influenced. If the bladder walls are incomplete due to the shadow, we can underestimate the bladder volume.

Therefore, if the user is provided with the pubic bone information, a better scanning location can be chosen and a more accurate bladder volume measurement can be made. We proposed the following method to make pubic bone detection based on the special shadow behind it.

On each plane, extract the left most and right most location with valid bladder wall, WL and WR. If there is no bladder walls on current plane or the wall width is too small, exit; else go on.

Compute the average frontwall depth ave_FW.
Determine the KI_threshold based on the whole image
From WL→0 searching for the shadow which is higher than ave_FW+searching_range, if there are more than N shadow lines in a row, record the shadow location WL_S.
From WR→nScanlines searching for the shadow which is higher than ave_FW+searching_range, if there are more than N shadow lines in a row, record the shadow location WR_S.
On one plane, it is only possible to have the pubic bone on one side of the bladder region. The starting location of the shadow is used to choose the most probable location for public bone.
Combine all valid shadow information and generate the location for pubic bone displaying In the above procedure, the most optionally advantageous factor is to determine the KI_threshold based on the B-mode images. We utilized an automated thresholding technique in image processing, Kittler & Illingworth thresholding method. Additional details may be found in the appendix.

Figure 31:
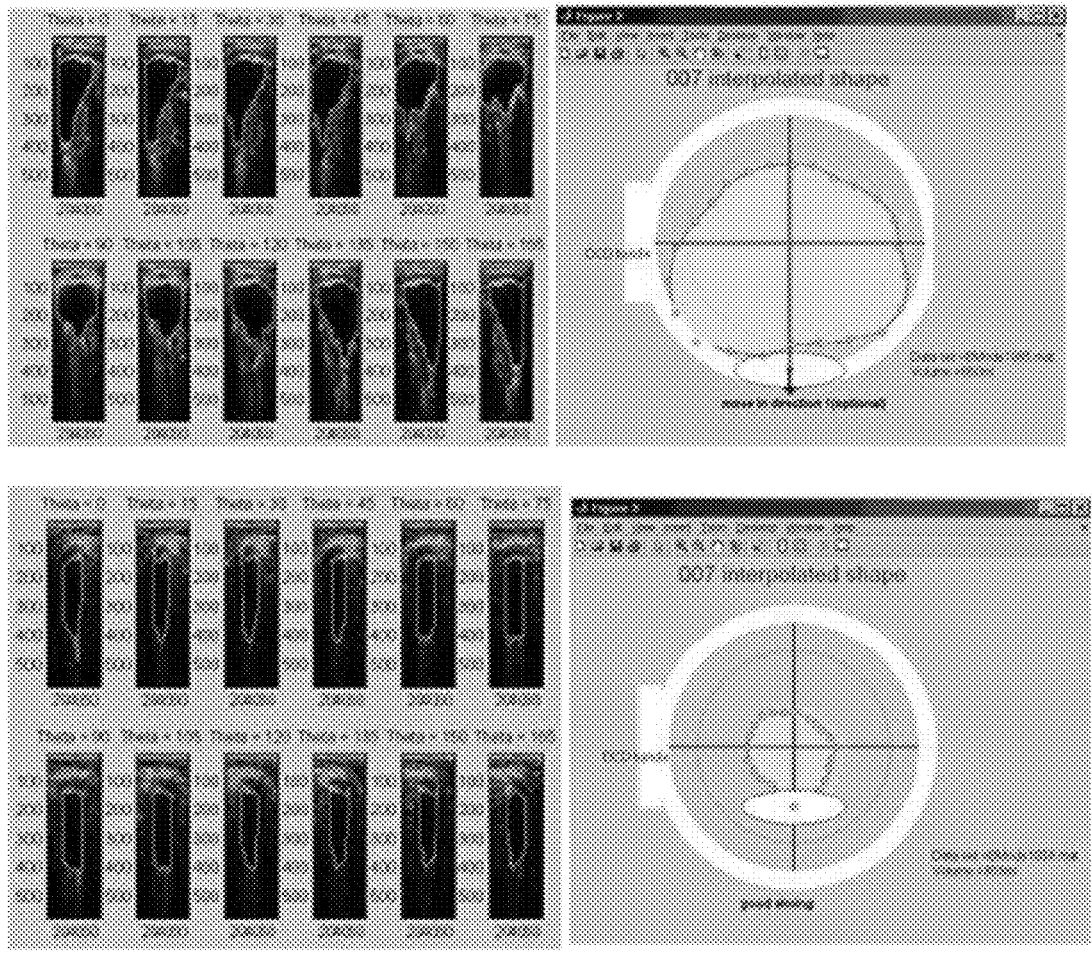
FIG. 31 illustrates shadow and segmentation regions of the pubic bone.

FIG. 31 illustrates shadow and segmentation regions of the pubic bone. Two examples with pubic bones close to the bladder region are illustrated. For the first one, the shadow is not affecting the volume measurement since the pubic bone is far from the bladder region; for the second case, the shadow is strong since the pubic bone blocks the bladder region partly.

Using the pubic icon on the feedback screen, operators are trained to recognize when a new scanning location should be chosen and when not. Also, the symbol ">" may be used when the bladder region is blocked by the pubic bone.

Intermediate shape. Basically, this step is still to show the C-mode shape. The difference between this step and the final C-mode shape is that this step is only using the grading information from the previous planes and gives instant response to the operator of current scanning status during a full scan. The first step is to use the grading values to find the cuts on current plane: For each plane, there are N scan lines gradings for all lines from previous step; Find the peak value and the corresponding line index; Special smoothing: Find the cuts on each plane: the left and right most line indices with grading values larger than a pre-specified threshold. [default threshold is 0.5]

Figure 32:
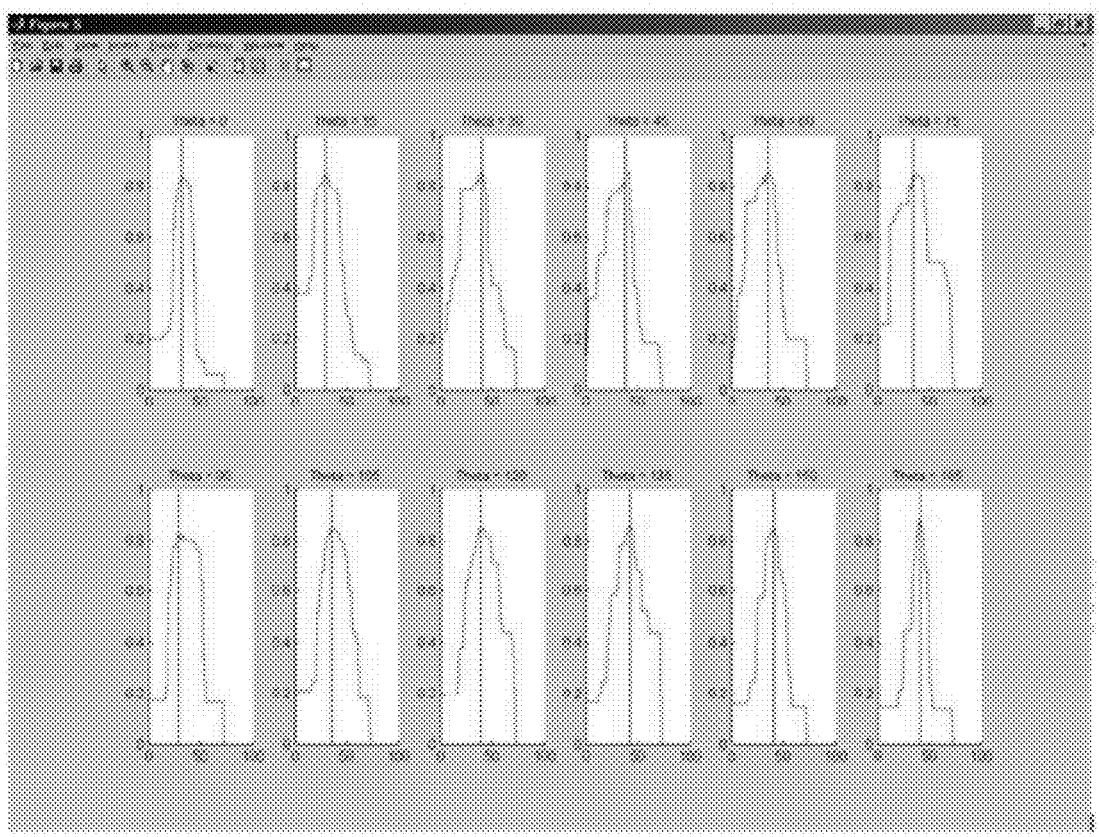
FIG. 32 illustrates examples of grading results derived from Neural Harmonics Algorithms.

FIG. 32 illustrates examples of grading results derived from Neural Harmonics Algorithms. The grading for all lines in data set 1028 are displayed for scan planes ranging from zero to 165 degrees in 15 degree increments.

Figure 33:
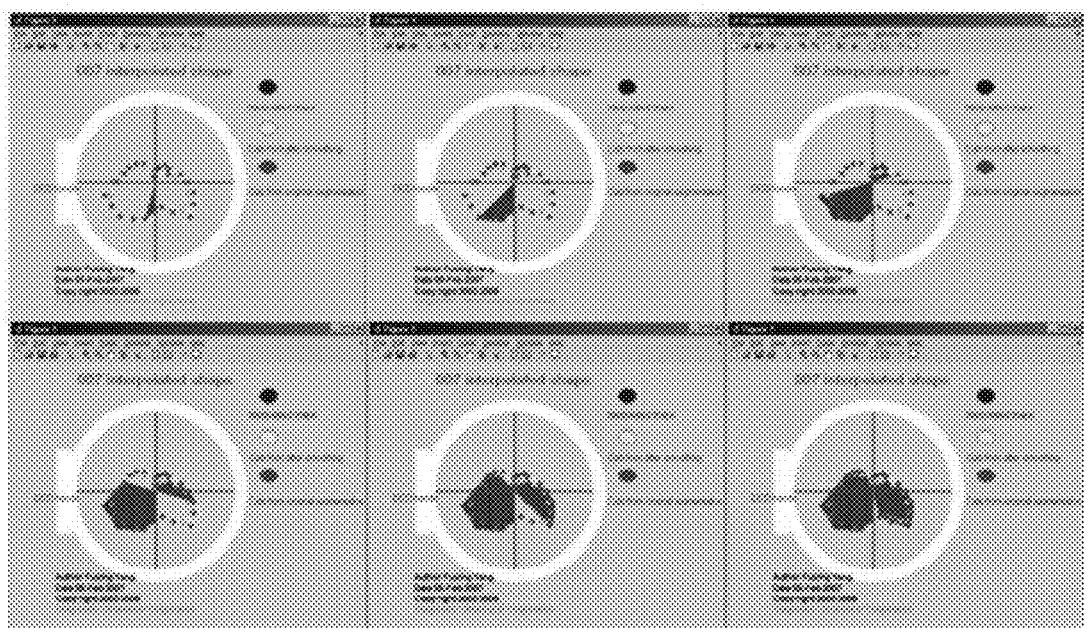
FIG. 33 illustrates a series of intermediate C-mode shapes generated as a screenshot interface or virtual painting board based on the grading results from FIG. 32.

FIG. 33 illustrates a series of intermediate C-mode shapes generated as a screenshot interface or virtual painting board. The cuts are found on each plane from the grading results shown in FIG. 32: the left and right most line indices with grading values larger than a pre-specified threshold. A default threshold of 0.5 may be used. The virtual painting board provides a vehicle to draw lines between the cuts or validly segmented regions of the organ cavity (i.e., bladder cavity) on current planes and cuts from previous planes. Shown are a series of intermediate C-mode shapes on data set 1028.

Figure 34:
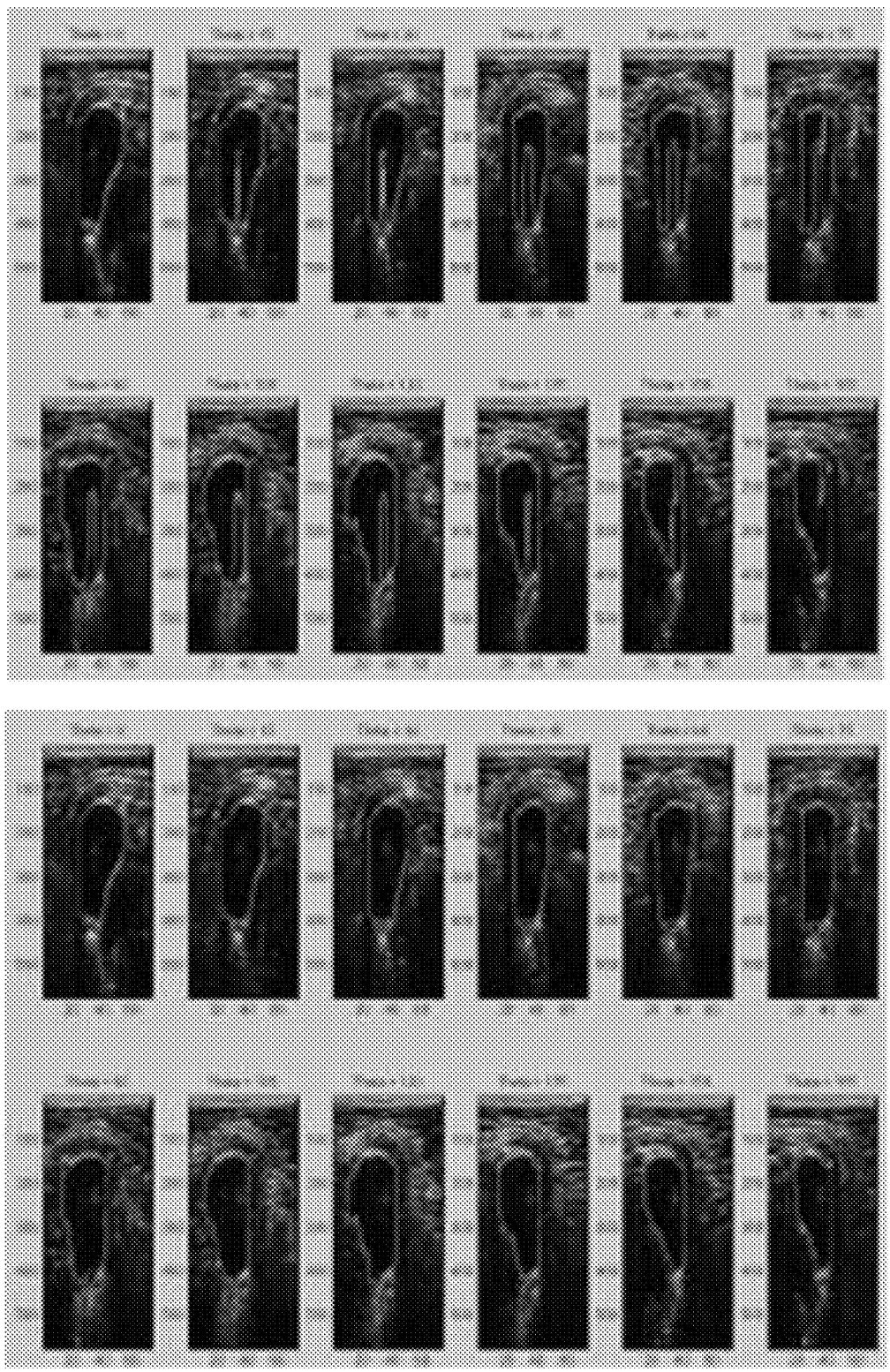
FIG. 34 illustrates segmentation results before and after using reverberation control method.

FIG. 34 illustrates segmentation results before and after using reverberation control method. Before we calculate the bladder volume based on the detected front and back walls, another extra step should be made to remove the wrong segmentation due to strong reverberation noise. The disclosed bladder wall detection method has the advantage over previous detection methods in that the grading information can help find the bladder lines as complete as possible. In previous transceiver versions (3000 and 6x00), the bladder wall detection can stop early when strong reverberation noise presents. However, under some circumstances the disclosed bladder wall detection method may not be able to fix the inaccurate segmentation on some lines due to reverberation noises.

Some regions in front of and behind the reverberation noise may be lost. After application of the reverberation control method, these regions were recovered as bladder region. Basically, the reverberation method is an interpolation approach using adjacent bladder wall shape in cases when the bladder shape is indeed with large convex part on the front or back wall by defining two parameters (valid_FW_change and valid_BW_change). The reverberation method below provides the capability to remove the small wedges on the bladder walls using the shape information:

If there is front wall on current line, search for the nearest front wall on the left, which has a front wall valid_FRONT WALL_change shallower than current front wall; search for the nearest front wall on the right, which also has a front wall valid_FRONT WALL_change shallower than current front wall. If the searching is successful on both sides, we use the found front wall pair to generate a new front wall at current location.

If there is bw on current line, search for the nearest front wall on the left, which has a bw valid_BW_change shallower than current bw; search for the nearest bw on the right, which also has a bw valid_BW_change shallower than current back wall. If the searching is successful on both sides, the found back wall pair is utilized to generate a new back wall at the current location.

Figure 35:
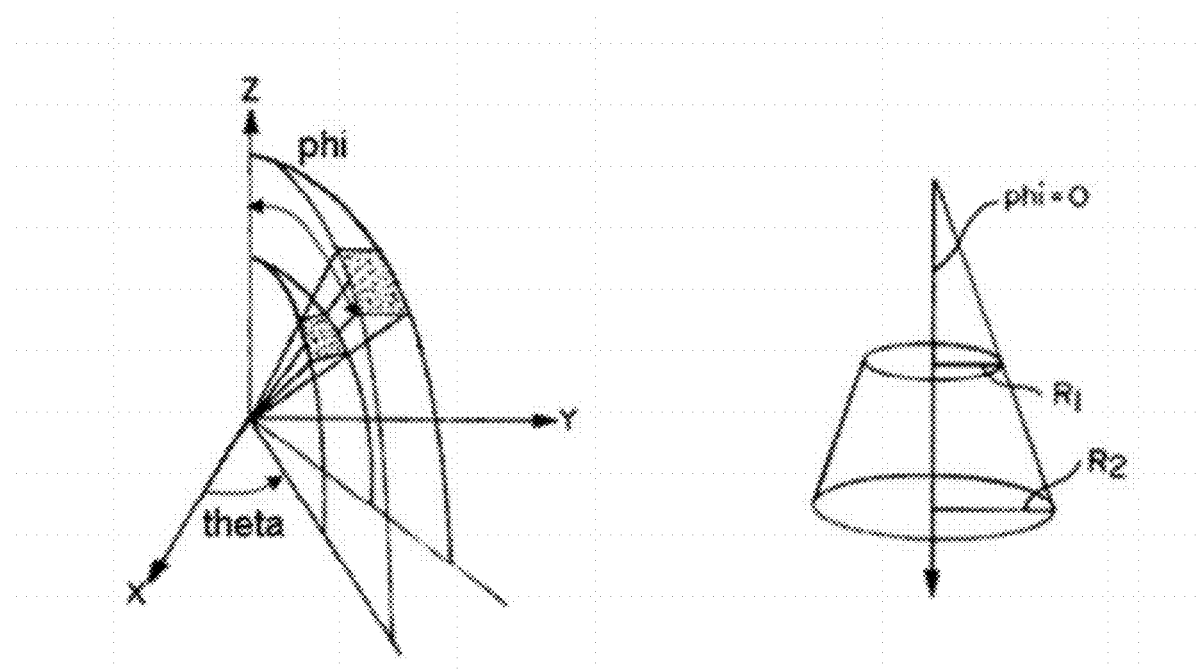
FIG. 35 illustrates models for volume computation.

FIG. 35 illustrates models for volume computation. In order to compute the bladder volume, the following information is optionally advantageous: Spherical coordinate phi and theta, the axial front wall and back wall locations, and the axial resolution. For every scan line except the broadside scan line (phi=0), a spherical wedge shape defined, with the physical scan line passed through the center of the wedge. The spherical wedge is bounded on top by the front wall and on the bottom by the back wall, on the sides by the average of the current scan line spherical angles and the next closest spherical angles (the left image of FIG. 36). For broadside scan line, a truncated cone is used (the right image of FIG. 36).

Clinical results. A large clinical experiment was made to evaluate the performance of the new bladder detection method designed for 9400. Twenty-two data sets were selected from a clinical trail and 38 data sets from another clinical trail, which include both pre-void and post-void cases. Based on the parameters we defined in Table 2 above, the following results are obtained as shown in Table 3:

TABLE 1 result without using harmonic information

| Patient ID | Visit No | Gender | Weight | Uroflow | Pre-Void | Post-Void | Post-Void + Uroflow | error |
|---|---|---|---|---|---|---|---|---|
| 1002 | Jan. 5, 2007 | Male | 175 | 450 | 470 | 28 | 478 | 0.017778 |
| 1004 | Jan. 5, 2007 | Male | 170 | 230 | 284 | 14 | 244 | 0.173913 |
| 1012 | Jan. 5, 2007 | Male | 155 | 270 | 252 | 9 | 279 | 0.1 |
| 1015 | Jan. 5, 2007 | Male | 200 | 100 | 51 | 10 | 110 | 0.59 |
| 1016 | Jan. 5, 2007 | Male | 140 | 250 | 345 | 43 | 293 | 0.208 |
| 1017 | Jan. 5, 2007 | Male | 175 | 280 | 361 | 24 | 304 | 0.203571 |
| 1028 | Jan. 24, 2007 | Male | 203 | 85 | 146 | 15 | 100 | 0.529412 |
| 1032 | Jan. 25, 2007 | Male | 205 | 359 | 474 | 12 | 371 | 0.286908 |
| 1033 | Jan. 25, 2007 | Male | 170 | 181 | 126 | 23 | 204 | 0.436464 |
| 1037 | Jan. 23, 2007 | Female | 115 | 443 | 553 | 52 | 495 | 0.130925 |
| 1040 | Jan. 24, 2007 | Female | 140 | 217 | 262 | 44 | 251 | 0.004608 |
| 1045 | Jan. 25, 2007 | Female | 150 | 172 | 238 | 9 | 181 | 0.331395 |
| 1049 | Jan. 5, 2007 | Male | 190 | 200 | 358 | 19 | 219 | 0.695 |
| 1051 | Jan. 5, 2007 | Male | 162 | 480 | 540 | 39 | 519 | 0.04375 |
| 1052 | Jan. 5, 2007 | Male | 170 | 310 | 347 | 18 | 328 | 0.06129 |
| 1057 | Jan. 25, 2007 | Female | 180 | 62 | 65 | 18 | 80 | 0.241935 |
| 1062 | Jan. 23, 2007 | Female | 160 | 326 | 337 | 73 | 399 | 0.190184 |
| 1064 | Jan. 24, 2007 | Female | 150 | 167 | 218 | 37 | 204 | 0.083832 |
| 1066 | Jan. 25, 2007 | Female | 130 | 227 | 296 | 36 | 263 | 0.145374 |
| 1067 | Jan. 24, 2007 | Female | 143 | 271 | 160 | 2 | 273 | 0.416974 |

TABLE 1-continued result without using harmonic information

| Patient ID | Visit No | Gender | Weight | Uroflow | Pre-Void | Post-Void | Post-Void + Uroflow | error |
|---|---|---|---|---|---|---|---|---|
| 1068 | Jan. 5, 2007 | Male | 185 | 520 | 472 | 163 | 683 | 0.405769 |
| 1068 | Jan. 23, 2007 | Male | 180 | 188 | 114 | 47 | 235 | 0.643617 |
| 1072 | Jan. 24, 2007 | Male | 260 | 249 | 253 | 13 | 262 | 0.036145 |
| 1073 | Jan. 24, 2007 | Female | 189 | 114 | 150 | 28 | 142 | 0.070175 |
| 1074 | Jan. 24, 2007 | Female | 118 | 322 | 468 | 15 | 337 | 0.406832 |
| 1075 | Jan. 24, 2007 | Male | 180 | 345 | 351 | 10 | 355 | 0.011594 |
| 1076 | Jan. 24, 2007 | Male | 150 | 130 | 282 | 24 | 214 | 0.357895 |
| 1077 | Jan. 25, 2007 | Female | 118 | 315 | 355 | 35 | 350 | 0.015873 |
| 1079 | Jan. 25, 2007 | Female | 112 | 226 | 266 | 74 | 300 | 0.150442 |
| | | | | | | | mean error | 0.241023 |
| | | | | | | | mean error 1 | 0.249907 |
| | | | | | | | mean error 2 | 0.236347 |

Figure 36:
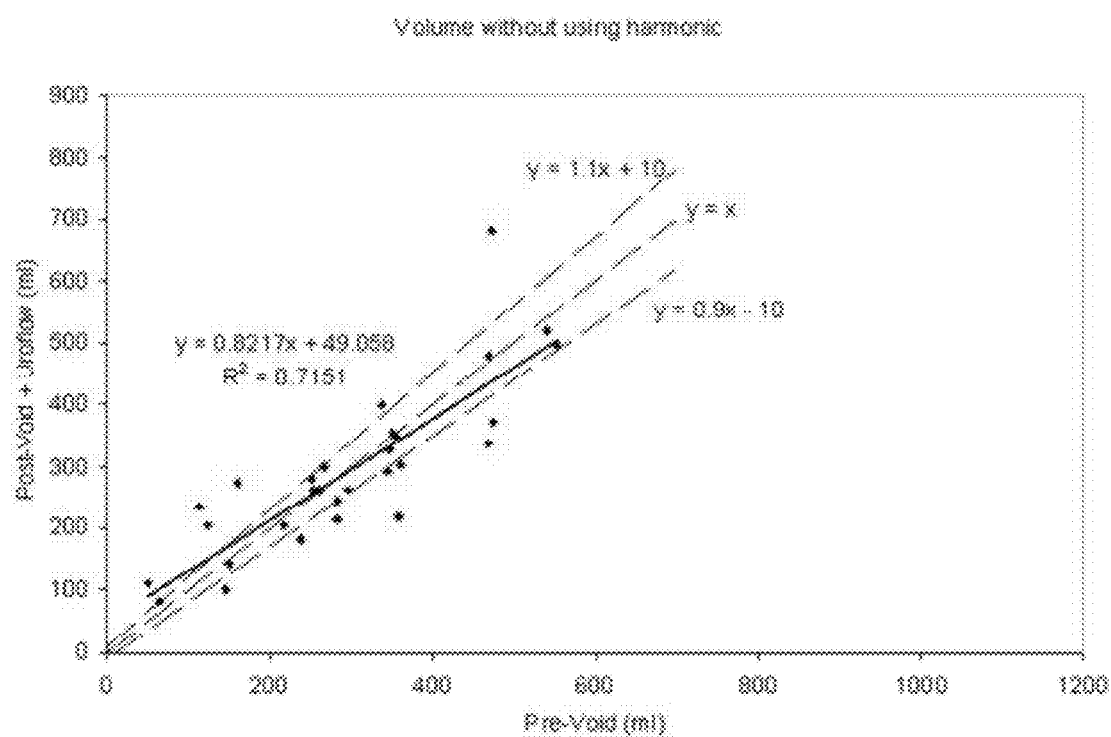
FIG. 36 illustrates a regression analysis result between pre void bladder volume measurement and the sum of the post void bladder volume measurement and urine volume without harmonic analysis.

FIG. 36 illustrates a regression analysis result between prevoid bladder volume measurement and the sum of the post void bladder volume measurement and urine volume without harmonic analysis. An $R^2$ value of 0.7151 is obtained.

Table 4 is a tabulation of results after using harmonic information processed by the neural network algorithm:

TABLE 1 result after using harmonic information in Neural Network

| Patient ID | Visit No | Gender | Weight | Uroflow | Pre-Void | Post-Void | Post-Void + Uroflow | error |
|---|---|---|---|---|---|---|---|---|
| 1002 | Jan. 5, 2007 | Male | 175 | 450 | 429 | 29 | 479 | 0.111111 |
| 1004 | Jan. 5, 2007 | Male | 170 | 230 | 290 | 4 | 234 | 0.243478 |
| 1012 | Jan. 5, 2007 | Male | 155 | 270 | 289 | 3 | 273 | 0.059259 |
| 1015 | Jan. 5, 2007 | Male | 200 | 100 | 54 | 2 | 102 | 0.48 |
| 1016 | Jan. 5, 2007 | Male | 140 | 250 | 286 | 15 | 265 | 0.084 |
| 1017 | Jan. 5, 2007 | Male | 175 | 280 | 352 | 7 | 287 | 0.232143 |
| 1028 | Jan. 24, 2007 | Male | 203 | 85 | 98 | 3 | 88 | 0.117547 |
| 1032 | Jan. 25, 2007 | Male | 205 | 359 | 606 | 12 | 371 | 0.376045 |
| 1033 | Jan. 25, 2007 | Male | 170 | 181 | 135 | 2 | 183 | 0.255193 |
| 1037 | Jan. 23, 2007 | Female | 115 | 443 | 618 | 53 | 496 | 0.275395 |
| 1040 | Jan. 24, 2007 | Female | 140 | 217 | 304 | 18 | 235 | 0.317972 |
| 1045 | Jan. 25, 2007 | Female | 150 | 172 | 233 | 6 | 178 | 0.319767 |
| 1049 | Jan. 5, 2007 | Male | 190 | 200 | 106 | 19 | 219 | 0.115 |
| 1051 | Jan. 5, 2007 | Wale | 162 | 480 | 559 | 56 | 536 | 0.047917 |
| 1052 | Jan. 5, 2007 | Male | 170 | 310 | 320 | 5 | 315 | 0.016129 |
| 1057 | Jan. 25, 2007 | Female | 180 | 62 | 55 | 7 | 69 | 0.225806 |
| 1062 | Jan. 23, 2007 | Female | 160 | 326 | 339 | 8 | 335 | 0.01227 |
| 1064 | Jan. 24, 2007 | Female | 150 | 167 | 201 | 8 | 175 | 0.166688 |
| 1066 | Jan. 25, 2007 | Female | 130 | 227 | 278 | 13 | 240 | 0.167401 |
| 1067 | Jan. 24, 2007 | Female | 143 | 271 | 242 | 8 | 279 | 0.136631 |
| 1068 | Jan. 5, 2007 | Male | 185 | 520 | 643 | 176 | 696 | 0.101923 |
| 1068 | Jan. 23, 2007 | Male | 180 | 188 | 173 | 25 | 214 | 0.218085 |
| 1072 | Jan. 24, 2007 | Male | 260 | 249 | 271 | 13 | 262 | 0.036145 |
| 1073 | Jan. 24, 2007 | Female | 189 | 114 | 119 | 11 | 125 | 0.052632 |
| 1074 | Jan. 24, 2007 | Female | 118 | 322 | 406 | 32 | 354 | 0.151491 |
| 1075 | Jan. 24, 2007 | Male | 180 | 345 | 377 | 15 | 360 | 0.048275 |
| 1076 | Jan. 24, 2007 | Male | 150 | 190 | 203 | 13 | 203 | 0 |
| 1077 | Jan. 25, 2007 | Female | 118 | 315 | 308 | 5 | 320 | 0.038095 |
| 1079 | Jan. 25, 2007 | Female | 112 | 226 | 253 | 44 | 270 | 0.075221 |
| | | | | | | | mean error | 0.15488345 |
| | | | | | | For Jan 5 data | mean error 1 | 0.149096 |
| | | | | | | For Jan 23-25 data | mean error 2 | 0.15792947 |

Figure 37:
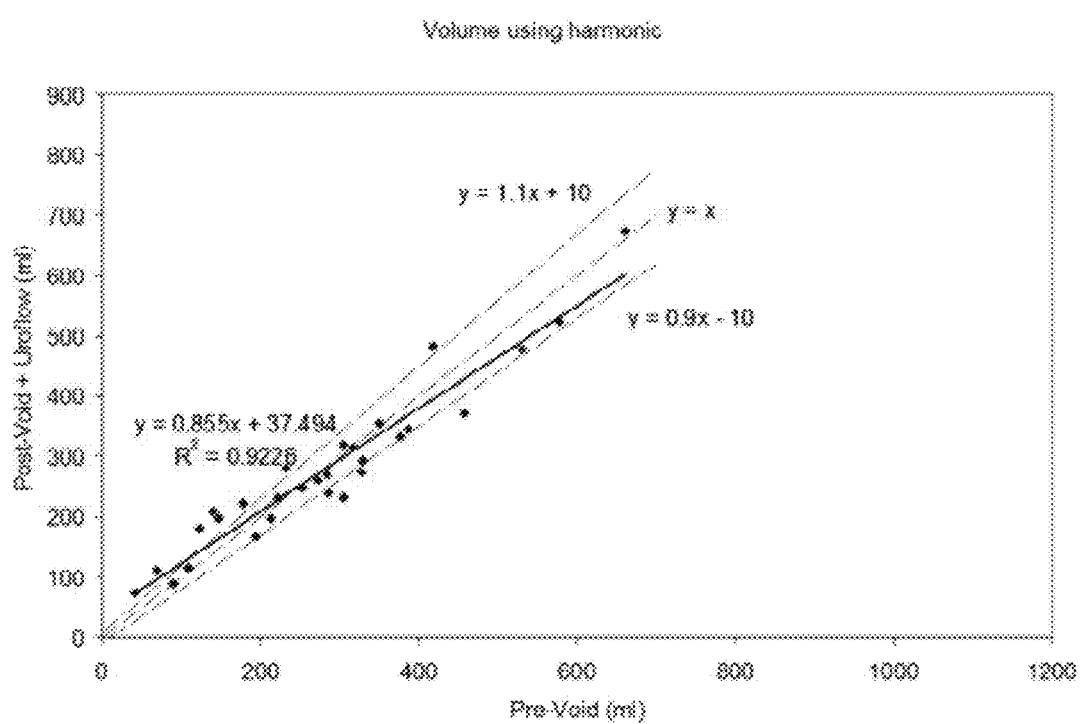
FIG. 37 illustrates a regression analysis result between prevoid bladder volume measurement and the sum of the post void bladder volume measurement and urine volume with harmonic analysis and using the neural network algorithm.

FIG. 37 illustrates a regression analysis result between prevoid bladder volume measurement and the sum of the post void bladder volume measurement and urine volume with harmonic analysis and using the neural network algorithm. An $R^2$ value of 0.9226 is obtained employing harmonic analysis—a much improved correlation than using the fundamental ultrasound frequencies shown in FIG. 36.

Table 5 is a tabulation of volume using the BVI3000 device on the same patient just before using the harmonic capable BVI9400 ultrasound transceiver.

TABLE 1

Jan 23-25 results using BVI3000

| Patient ID | Visit No | Gender | Weight | Uroflow | Pre-Void BVI 3000 | Post-Void BVI 3000 | Post-Void BVI 3000 + Uroflow | 3000 error |
|---|---|---|---|---|---|---|---|---|
| 1028 | Jan. 24, 2007 | Male | 203 | 85 | 104 | 0 | 85 | 0.223529 |
| 1032 | Jan. 25, 2007 | Male | 205 | 359 | 410 | 0 | 359 | 0.142061 |
| 1033 | Jan. 25, 2007 | Male | 170 | 181 | 141 | 0 | 181 | 0.220994 |
| 1037 | Jan. 23, 2007 | Female | 115 | 443 | 452 | 23 | 466 | 0.031603 |
| 1040 | Jan. 24, 2007 | Female | 140 | 217 | 239 | 0 | 217 | 0.101382 |
| 1045 | Jan. 25, 2007 | Female | 150 | 172 | 154 | 56 | 228 | 0.430233 |
| 1057 | Jan. 25, 2007 | Female | 180 | 62 | 108 | 91 | 153 | 0.725806 |
| 1062 | Jan. 23, 2007 | Female | 160 | 326 | 375 | 39 | 356 | 0.058282 |
| 1064 | Jan. 24, 2007 | Female | 150 | 167 | 166 | 0 | 167 | 0.005988 |
| 1065 | Jan. 25, 2007 | Female | 130 | 227 | 277 | 28 | 255 | 0.096916 |
| 1067 | Jan. 24, 2007 | Female | 143 | 271 | 188 | 0 | 271 | 0.306273 |
| 1069 | Jan. 23, 2007 | Male | 180 | 188 | 187 | 0 | 188 | 0.005319 |
| 1072 | Jan. 24, 2007 | Male | 260 | 249 | 311 | 0 | 249 | 0.248996 |
| 1073 | Jan. 24, 2007 | Female | 189 | 114 | 222 | 0 | 114 | 0.947368 |
| 1074 | Jan. 24, 2007 | Female | 118 | 322 | 304 | 0 | 322 | 0.055901 |
| 1075 | Jan. 24, 2007 | Male | 180 | 345 | 314 | 0 | 345 | 0.089855 |
| 1076 | Jan. 24, 2007 | Male | 150 | 190 | 321 | 0 | 190 | 0.688474 |
| 1077 | Jan. 25, 2007 | Female | 118 | 315 | 339 | 0 | 315 | 0.07619 |
| 1079 | Jan. 25, 2007 | Female | 112 | 226 | 280 | 27 | 253 | 0.119469 |
| | | | | | | | mean error | 0.240823 |

Figure 38:
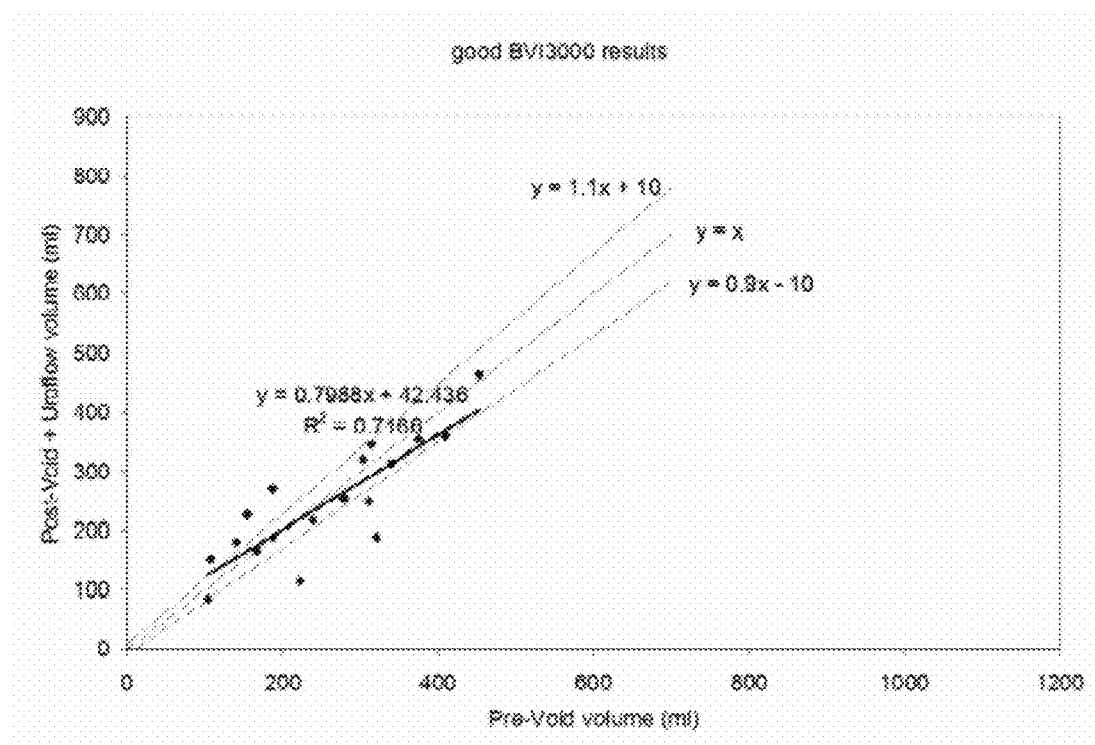
FIG. 38 illustrates a regression analysis result between prevoid bladder volume measurement and the sum of the post void bladder volume measurement and urine volume by the BVI3000 system which is not capable to execute harmonic analysis.

FIG. 38 illustrates a regression analysis result between prevoid bladder volume measurement and the sum of the post void bladder volume measurement and urine volume by the BVI3000 system which is not capable to execute harmonic analysis. An $R^2$ value of 0.7166 is obtained—a much lowered correlation than to FIG. 37 above that derives from the harmonic capable BVI9400 transceiver.

A simple comparison can be made that:

Using harmonic information in Neural Network decreases the error by 8.61%. (Table 3), 24.10% (Table 4), and 15.49% (Table 5).

Correlation coefficient after using harmonic in Neural Network is increased by 0.12. (Table 3), $\sqrt{0.9226}$ (Table 4), and $\sqrt{0.7151}$ (Table 5).

BVI9400 is more accurate than BVI3000 and the error is decreased by 8.29% (Table 3), 24.08% (Table 4), and 15.79% (Table 5).

Figure 39:
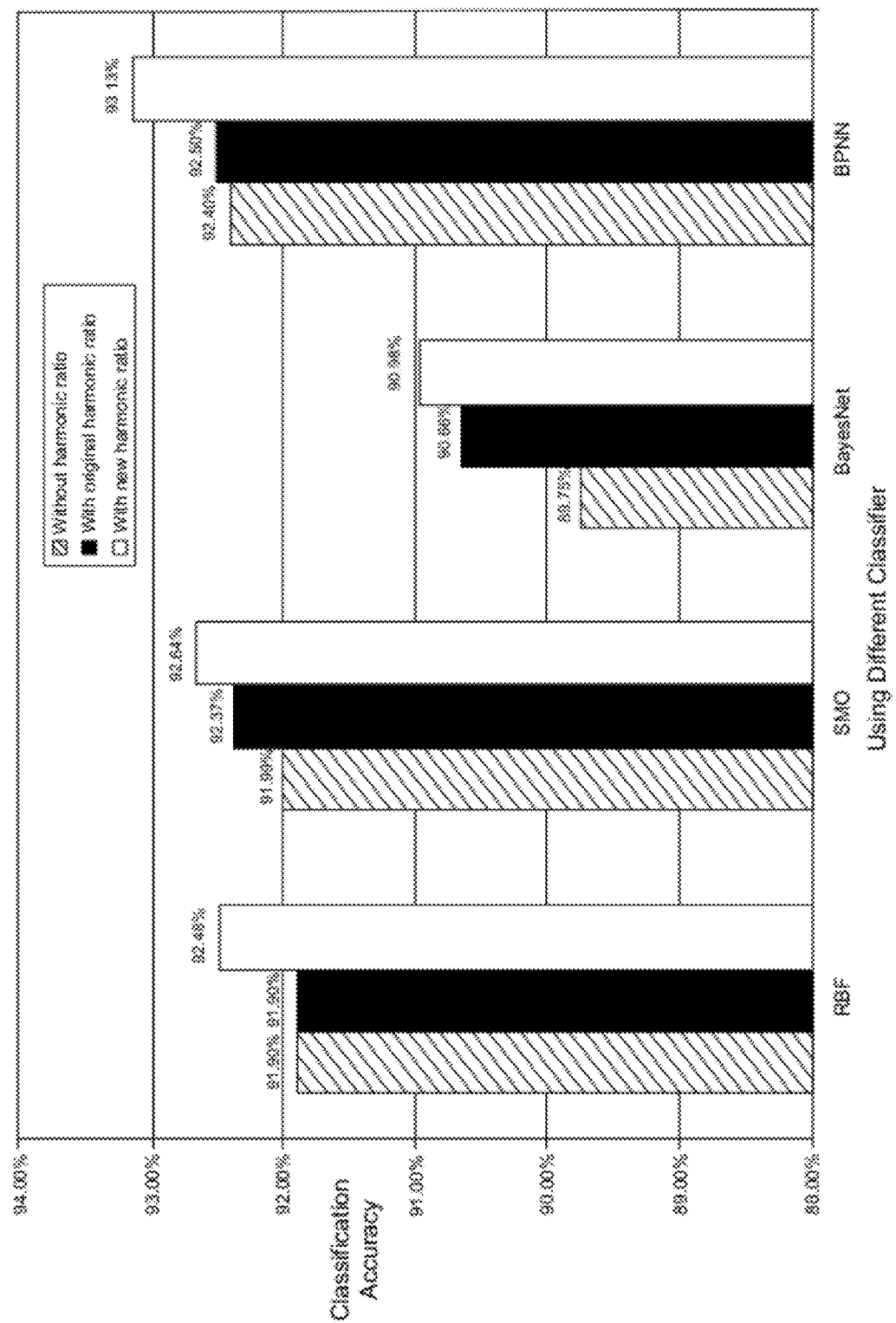
FIG. 39 presents a comparison of the bladder line classification results between the method using harmonic ration as a feature and the method without using harmonic ratio as a feature. The comparisons are made multiple times using different classifiers, including RBF (Radial Basis Function), SMO, BayesNet and Backpropogation Neural Network.

FIG. 39 presents a comparison of the bladder line classification results between the method using harmonic ratio as a feature and the method without using harmonic ratio as a feature. The comparisons are made multiple times using different classifiers, including RBF (Radial Basis Function), SMO, BayesNet and Backpropogation Neural Network. For each classification problem, the selection of features is directly related to the system performance. In the bladder line classification problem, the performance by choosing different feature combinations are compared and different classifiers for the evaluation are examined using a 10-fold cross validation method, using 9 folds for training and one for testing.

Three different feature combinations are tested:

Without harmonic ratio: tissueDelta, minRsum, FRONT WALL and BW, 4 features only.

With traditional harmonic ratio: tissueDelta, old harmonic ratio, minRsum, FRONT WALL and BW, 5 features.

Figure 40:
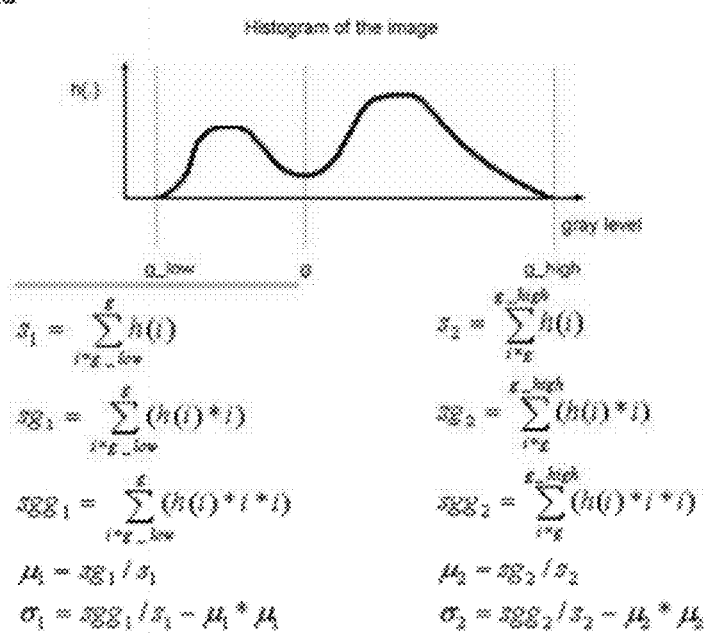
FIG. 40 is an illustration of a KI threshold algorithm.

With harmonic ratio computed using harmonic analysis kernel: tissueDelta, new harmonic ratio, minRsum, FRONT WALL and BW, 5 features. Four different classifiers include, RBF network, Support Vector Machine and BayesNet, Back Propagation Network FIG. 40 is an illustration of a KI threshold algorithm. Consult appendix for further explanations of thresholding procedures.

Figure 41A:
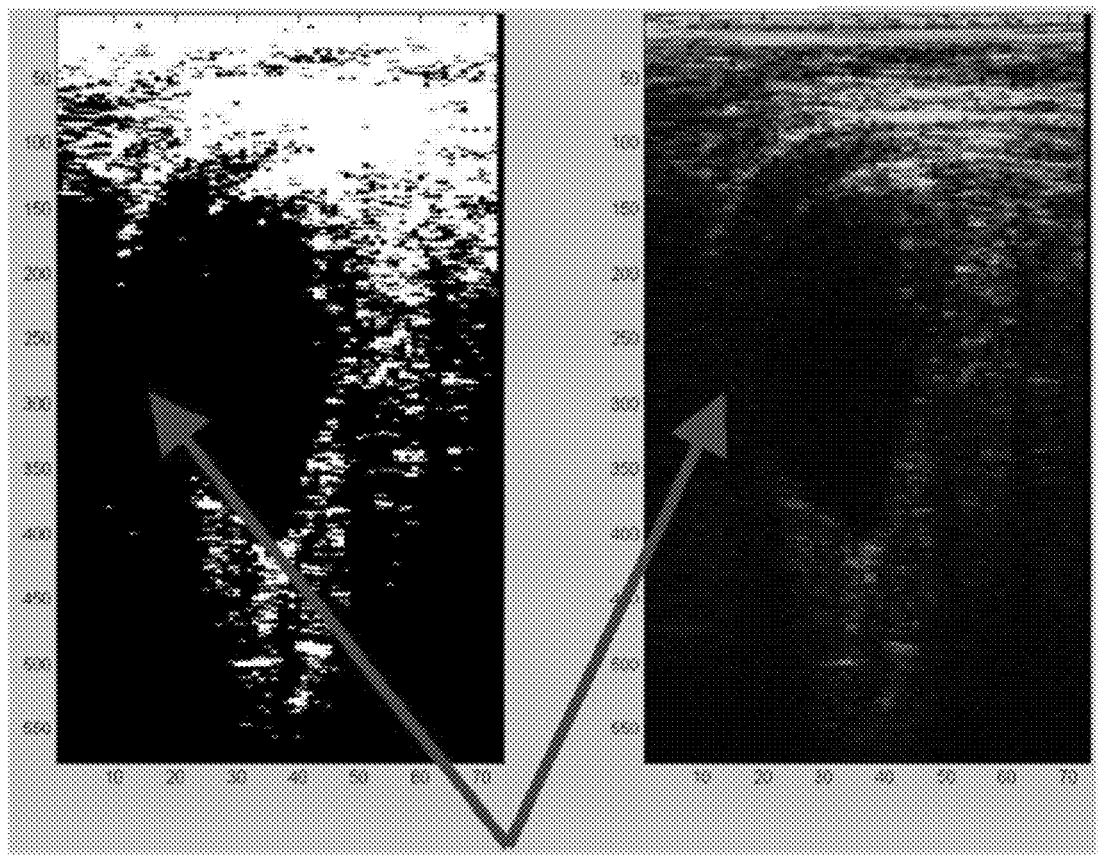
FIGS. 41A and 41B illustrated B-mode 1058 plane after thresholding at 29 and 28.
Figure 41B:
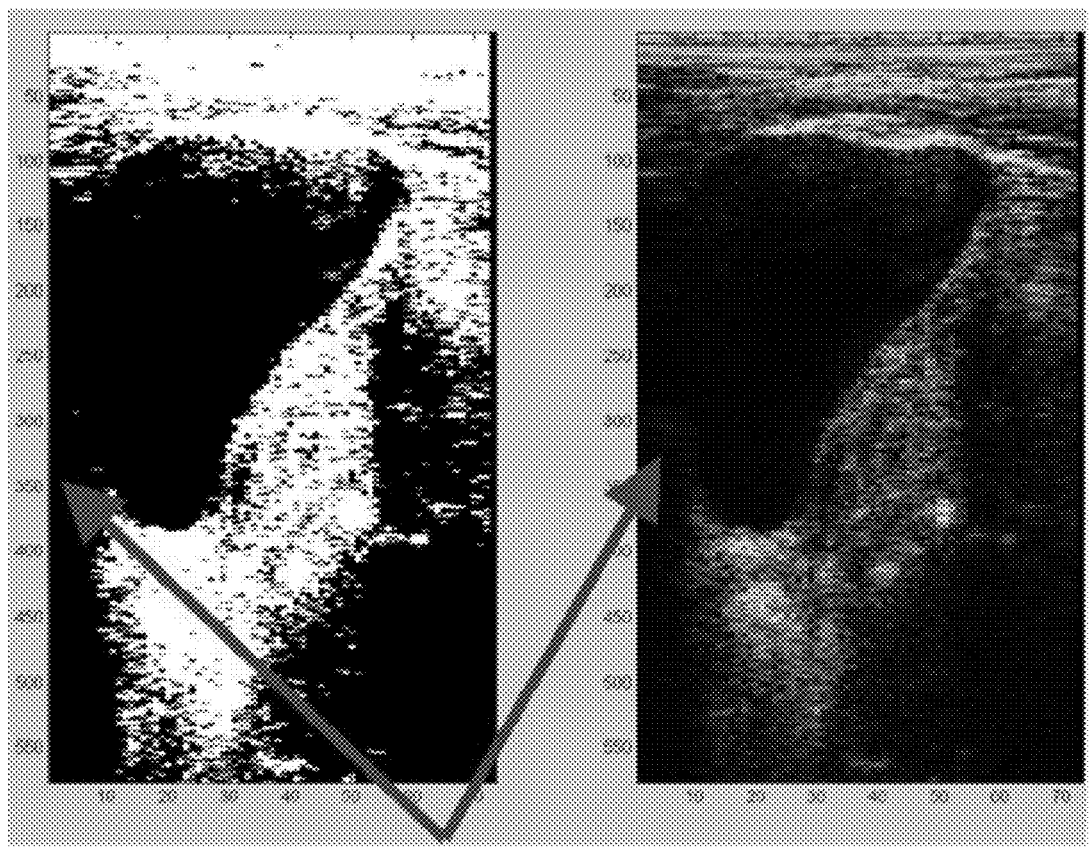

FIGS. 41A and 41B illustrated B-mode 1058 plane after thresholding at 29 and 28.

Figure 42:
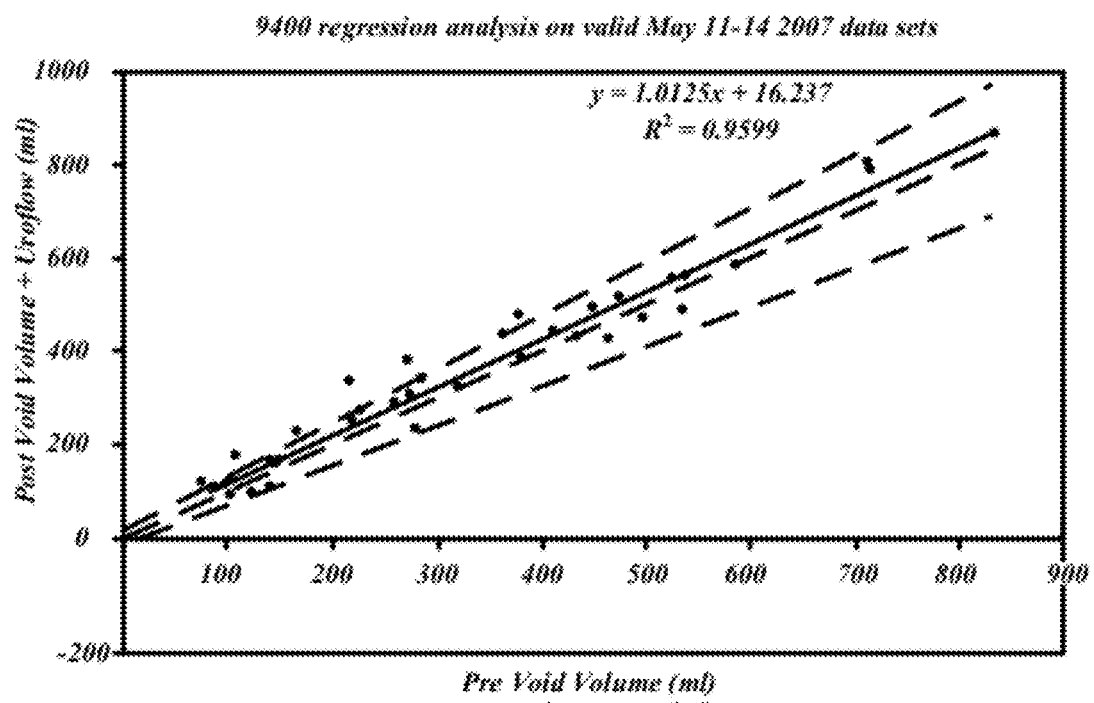
FIGS. 42-44 are regression plot analyses results of the clinical experiment on May 11-14, 2007, which are based on three different bladder scan system, 9400, 3000 and 6400.
Figure 43:
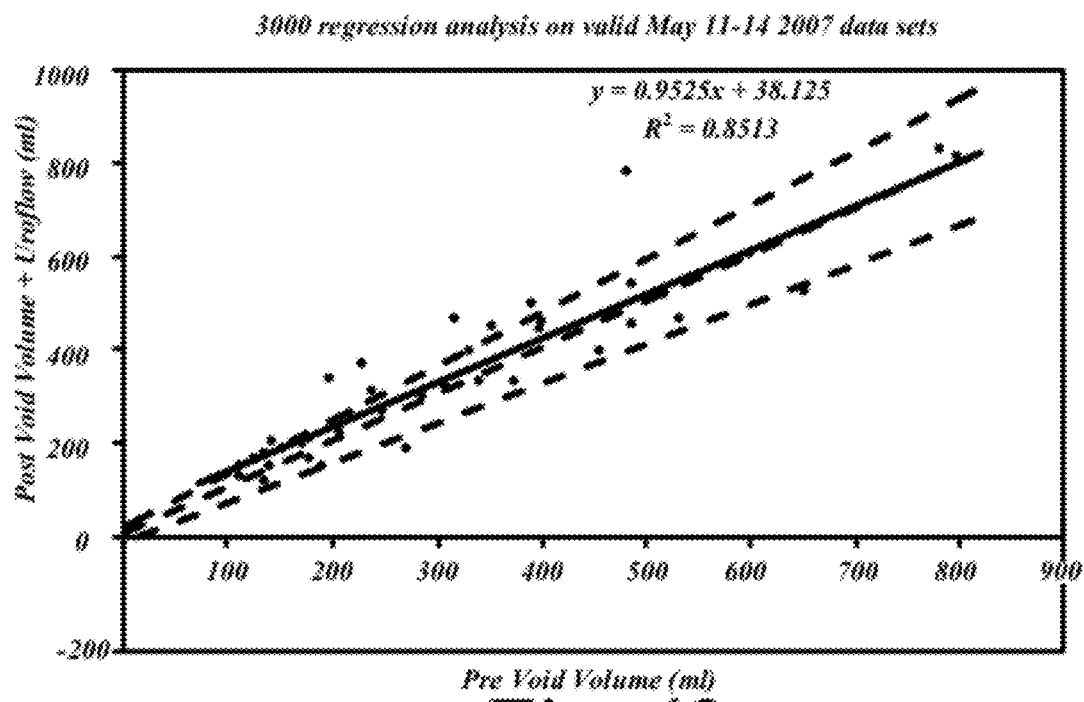
Figure 44:
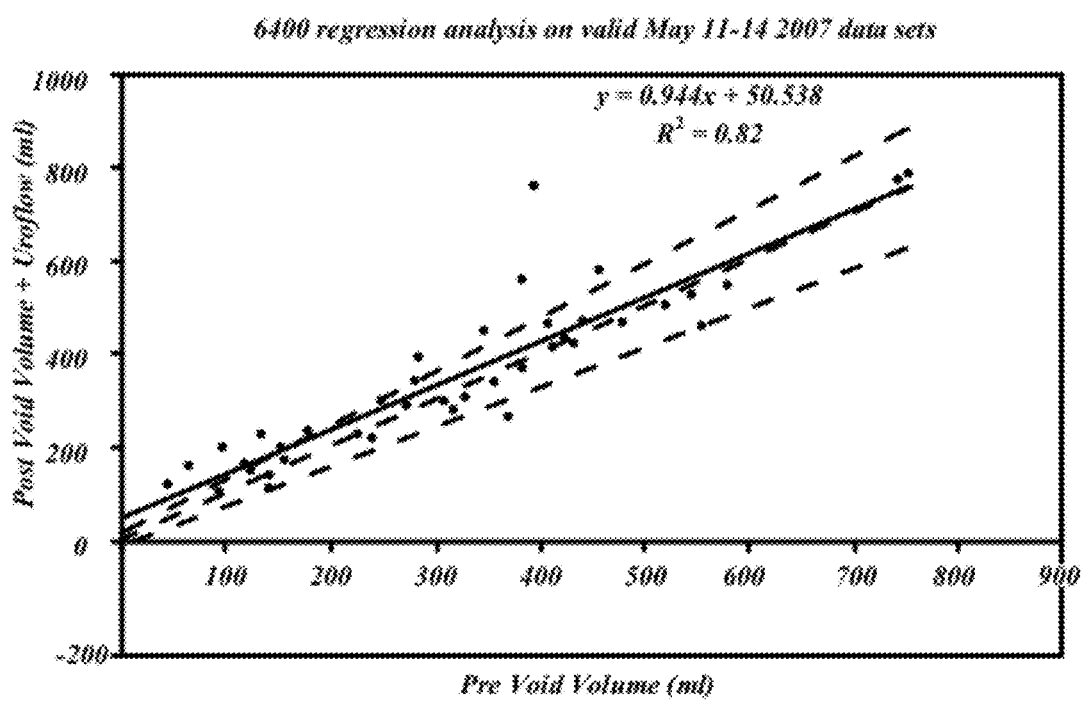

FIGS. 42-44 are regression plot analyses of clinical data described below,

The performance of the BVI9400 compared with the BVI3000 and BVI6400 transceivers 10A-B is described in a study undertaken using two ultrasound scans of patient's bladders using 2 different BladderScan® 9400 and BVI 3000 devices and BVI6400 on 1 occasion. Subjects were not required to drink more water before scanning. There can be total of 8 scans (2 pre-void and 2 post-void) during the visit. After successful scan, the participants can be asked to void into the Uroflow device and wait for the resulting printout. The participant shall give the investigator the printed record from the Uroflow so that it may be stored with the other trial records. The participant shall then return for post-void scan using the same collection protocol as for the pre-void.

A clinical sample derived from 42 healthy and consenting individuals underwent bladder volume measurements using the BVI model 3000, 6000, and 9400 series transceivers having configurations similar to transceivers 10A-B. The 3000 and 6000 transceivers are different from the 9400 series by the transducer design and algorithms employed. The 9400 transducer is more powerful and can achieve a duo format task of acquiring B-mode based images and harmonic information collection. The 9400 B-mode image renders higher resolution than the images produced by the 3000 and 6400 transceivers.

The algorithms operating within the 9400 transceivers 10A-B utilize harmonic based imaging data and neural network processing illustrated for the NNA 224 in detecting bladders. In contrast the algorithms employed in the 3000 and 6400 transceivers obtain bladder volume measurement is made via a bladder detection module employing B-mode image information for segmentation and subsequent 3D volume computations based on the B-mode segmentation. However, female uterus and/or B-mode image noise may obscure bladder detection accuracy in the 3000 and 6400 series transceivers.

A total of 42 subjects (21 males and 21 females) participated in this study utilizing three BVI9400 devices. Regression analysis is made between the prevoid volume and postvoid volume+uroflow. The charts are given in the following. The dashed lines give the ±15%±15 ml range. Data sets are summarized in the below:

1097 female: no uroflow
1005 female: no uroflow
1035 female: no measurement using the second 9400 1096 female: no measurement using the second 9400 1071 female: no measurement using the second 9400

The new segmentation method uses the extra information associated with the $2^{nd}$ harmonic ratio to provide a more robust and accurate bladder volume measurement. The harmonic based algorithms may be applied to other organs having cavity structures, for example the heart. The extra information is combined with the features from B-mode images. Then instead of using many simple hard-threshold based criterions for segmentation, a more powerful Neural Network is constructed. Each scan line is classified as tissue line or bladder line. The classifier is pre-trained upon a large data sets and the accuracy is high, which guaranteed the detection of the bladder region in current scan. In general, the new design has the advantage over previous designs in the following aspects: The detection of the bladder region can be more robust since more information, including harmonic ratio, is integrated instead of using B-mode intensity (gradient information) only. The female uterus or B-mode image noise can be recognized by the pre-trained classifier and the segmentation cannot give large over or underestimation of the bladder volume.

| The slope and square of the correlation coefficient ($R^2$) is used for accuracy evaluation and cross-instrument comparison. | | | |
|---|---|---|---|
| | 9400 | 3000 | 6400 |
| $R^2$ | 0.9599 | 0.8513 | 0.82 |
| Slope | 1.0125 | 0.9525 | 0.944 |

From the above testing result, we are confident that our 9400 product is able to achieve more robust bladder measurement and higher accuracy than previous versions.

The detection method is described for the BVI9400 transceiver and its alternate embodiments illustrated for transceivers 10A-B-C. Compared with previous products, including 3000 and 6100 series, 9400 is equipped with harmonic analysis function, which is utilizing the information embedded in frequency for more accurate bladder volume measurement. In addition to that, fast aiming functionality is added, which provide the operator to locate the best scanning direction and angle. The new bladder detection method is the foundation for all these new DSP applications and new functionalities.

APPENDIX A. DSP IMPLEMENTATION OF LOGARITHM

DSP implementation of logarithm computation (source code in matlab) method 1.

```
function [result] = Goldberg_log(M,fdigits,base)
%%%%%%%%%%%%%%%%%%%%%%%%%%%%%%%%%%%%%%%%%%%%%%%%%%%
%%%%%%%%%%%%%%%%%%%%%%%%%%%%%%%
    %The function is to implement the method proposed in Goldberg, M.:
    %Computing Logarithms Digit by Digit. BRICS Research Series, Aarhus;
    %(RS?04?17): 6, 2004. The method is an algorithm for computing logarithms
    %of positive real numbers, that bares structural resemblance to the
    %elementary school algorithm of long division. Using this algorithm,
    %we can compute successive digits of a logarithm using a 4-operation
    %pocket calculator. The algorithm makes no use of Taylor series or
    %calculus, but rather exploits properties of the radix-d representation
    %of a logarithm in base d. As such, the algorithm is accessible to
    %anyone familiar with the elementary properties of exponents and logarithms."
    %
    % M : input positive real value
    % fdigits: the fractional digitis, which determines the accuracy
    % base : the base of the logarithms
    %
    % result: the result of the Logarithms operation
    %
    % Fuxing Yang 2006-03-01 Initial created
    %%%%%%%%%%%%%%%%%%%%%%%%%%%%%%%%%%%%%%%%%%%%%%%%%%%
    %%%%%%%%%%%%%%%%%%%%%%%%%%%%%%%
    if (M<=0)
        fprintf('Invalid input: M has to be a negative real value.\n');
        return;
    elseif (M>1)
        [result] = Goldberg_log_lg(M,fdigits,base);
    elseif (M<1)
        r = 0;
        temp_M = M;
        while (temp_M<1)
            r = r + 1;
            temp_M = temp_M*base;
        end
        [result] = Goldberg_log_lg(temp_M,fdigits,base);
        result = result - r;
    else
        result = 0;
    end
```

```
%comparison for debugging
%%%%%%%%%%%%%%%%%%%%%%%%%%%%%%%%%%%%%%%%%%%%%%%%%%%%%%
%%%%%%%%%%%%%%%%%%%%%%%%%%%%
% r_result = log2(M);
% fprintf('Result from Goldberg method = %4.10f\n',result);
% fprintf('Result from matlab logarithm operation = %4.10f\n',r_result);
function [lg_result] = Goldberg_log_lg(M,fdigits,base)
r = 0;
temp_M = 1;
while (temp_M<=M)
    if (temp_M==M)
        lg_result = r;
        return;
    end
    r = r + 1;
    temp_M = temp_M*base;
end
first_digit = r−1;
last_M = M;
last_a = first_digit;
for f = 1:fdigits
    r = 0;
    temp_M = 1;
    M_f = 1;
    for x =1:last_a
        M_f = M_f* base;
    end
    M_e = last_M/M_f;
    M_c = 1;
    for x =1:base
        M_c = M_c*M_e;
    end
    while (temp_M<M_c)
        r = r + 1;
        temp_M = temp_M*base;
    end
    f_digit(f) = r−1;
    last_M = M_c;
    last_a = r−1;
end
lg_result = first_digit;
for f = 1:fdigits
    f_base = 1;
    for x =1:f
        f_base = base*f_base;
    end
    lg_result = lg_result+f_digit(f)/f_base;
end
```

DSP implementation of logarithm computation (source code in matlab) method 2.
This method is based the IEEE Standard for Binary Floating-Point Arithmetic (IEEE 754).

Single-precision 32 bit
(adopted from Wikipedia at http://en.wikipedia.org/wiki/IEEE_754)

A single-precision binary floating-point number is stored in a 32-bit word:

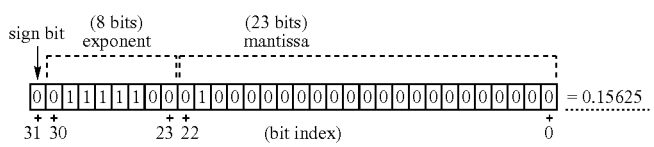

The exponent is biased by $2^{8−1} − 1 = 127$ in this case, so that exponents in the range −126 to +127 are representable. An exponent of −127 would be biased to the value 0 but this is reserved to encode that the value is a denormalized number or zero. An exponent of 128 would be biased to the value 255 but this is reserved to encode an infinity or not a number (NaN). See the chart above.

For normalised numbers, the most common, Exp is the biased exponent and Fraction is the fractional part of the significand. The number has value v:

$v = s \times 2^e \times m = \text{sign} \times 2^{exponent} \times \text{mantissa}$

Single-precision 32 bit
(adopted from Wikipedia at http://en.wikipedia.org/wiki/IEEE_754)

Where
s = +1 (positive numbers) when the sign bit is 0
s = −1 (negative numbers) when the sign bit is 1
e = Exp − 127 (in other words the exponent is stored with 127 added to it, also called "biased with 127")
m = 1.Fraction in binary (that is, the significand is the binary number 1 followed by the radix point followed by the binary bits of Fraction). Therefore, $1 \leq m < 2$.
In the example shown above, the sign is zero, the exponent is −3, and the significand is 1.01 (in binary, which is 1.25 in decimal). The represented number is therefore $+1.25 \times 2^{-3}$, which is +0.15625.

Based on IEEE754, a fast log 2 (log 10 and ln) algorithm can be designed as following c code

```
float log2 (float value)
{
    int * const  ptr = (int *) (&value);
    int    intval = *ptr;
    //In theory, the bias is 127 for floats. But in this method, the
polynomial is to map [1 ; 2] onto [1 ; 2] (instead of [0 ; 1]
    //as it would be required if 127 is used). Thus it could be easily
removed for faster (linear) approximation. A possible optimization
    //could be done by moving the bias in the polynomial.
    int  log_2 = ((x>>23) & 255) − 128;    //exponent
    intval &= ~(255 << 23);                //mantissa
    intval += 127 << 23;                   //exponent of mantissa
    *ptr = intval;
    //special process on exponent of mantissa
    //The proposed formula is a 3rd degree polynomial keeping first
derivate continuity. Higher degree could be used for
    //more accuracy. For faster results, one can remove this line, if
accuracy is not the matter (it gives some linear interpolation between
    //powers of 2).
    value = ((−1.0f/3) * value + 2) * value − 2.0f/3;
    //combine the original exponent and exponent of mantissa
    return (value + log_2);
};
Log10 (value)= log2(value)/ 3.3219f;
Ln(value) = log2(value)/ 1.4427f;
```

For example: Value=0.00213 (binary format used by IEEE754) 00111011000010111001011101111000
Note: 0—sign bit
0 —exponent bit
0—significand (mantissa) bit
Exponent is −10 (01110110−128=118−128).
Mantissa is 00010111001011101111000.
Exponent of the mantissa is 1.09056.
Special process of the exponent of the mantissa is a 3rd degree polynomial keeping first derivate continuity. Higher degree could be used for more accuracy. For faster results, one can remove this special process, if accuracy is not the matter (it gives some linear interpolation between powers of 2). Then the exponent of the mantissa is changed into 1.15271. Combine the two exponents and the final exponent for input value is −10+1.15271=−8.8473.

APPENDIX B. NEURAL NETWORK TRAINING

Training data sets were collected on Jan. 5, 2007. Totally there are 12 patients, including 1002, 1004, 1005, 1008, 1012, 1015, 1016, 1017, 1049, 1051, 1052 and 1068. [post-void and pre-void]. There are 12*72*24=20736 scan lines. Based on manual grading, there are 8250 bladder lines and 12486 tissue lines. (It can be regarded as balanced data sets for training.) We implemented a back propagation Neural Network using logistic functions. The structure of the network is 5 by 5 by 1. We used a 10-fold cross validation method and the accuracy of the trained network is 92.26%. The trained network is in the following configuration (please refer to source code defined in NN.h and NN.c.

```
#define n_input_units       5
#define n_hidden_units      5
#define n_output_units      1
#define na_input_units      n_input_units + 1
#define na_hidden_units     n_hidden_units + 1
#define na_output_units     n_output_units + 1
const double BPNN_IH[na_input_units][na_hidden_units] =
{
{0,    0,            0,            0,            0,            0},
{0,    13.008636,    −5.242537,    −8.093809,    0.738920,     −1.345708},
{0,    2.039624,     2.109022,     −3.339866,    −3.926513,    −6.129284},
{0,    −4.525894,    −4.832823,    3.689193,     −3.612824,    −1.418404},
{0,    −6.834694,    −3.932294,    7.301636,     0.151018,     −6.567073},
{0,    −0.997530,    −6.582561,    1.040930,     −4.179786,    6.771766}
};
const double BPNN_HO[na_hidden_units][2] =
{
    {0,0},
    {0,2.654482},
    {0,−17.31553},
    {0,−1.429942},
    {0,−11.77292},
    {0,−2.519807}
};
const double maxfeature[na_input_units] =
{0, 238.7272727, 43.49219326, 2048, 294, 536};
const double minfeature[na_input_units] =
{0, 0, 6.46712798, 1, 0, 0};
```

In order to confirm the performance of the Network, results obtained from a pattern recognition tool kit Weka (available from the University of Waikato, Hamilton, New Zealand), on the same training data sets using different classifiers and we have the following results:

| RBFNetwork | Correctly Classified Instances | 19056 | 91.8981% |
|---|---|---|---|
|  | Incorrectly Classified Instances | 1680 | 8.1019% |
| SMO | Correctly Classified Instances | 19153 | 92.3659% |
|  | Incorrectly Classified Instances | 1583 | 7.6341% |

APPENDIX C. CLASSIFICATION AND FEATURES—FIG. 39

For classification problem, the selection of features is directly related to the system performance. In our project, for bladder line classification problem, we compared the performance by choosing different feature combinations. Also, we used different classifiers for the evaluation too. The data set for this comparison is based on the clinical data collected on Jan. 5, 2007. The method we used is a 10-fold cross validation method. [Use 9 folds for training and one for testing.] Three different feature combinations are tested:
  without harmonic ratio: tissueDelta, minRsum, FRONT WALL and BW, 4 features
  with traditional harmonic ratio: tissueDelta, old harmonic ratio, minRsum, FRONT WALL and BW, 5 features
  with harmonic ratio computed using harmonic analysis kernel: tissueDelta, new harmonic ratio, minRsum, FRONT WALL and BW, 5 features Four different classifiers are used:
RBF network
Support Vector Machine
BayesNet
Back Propagation Network
  From the results, we are able to make the following conclusions:
harmonic information can improve the classification accuracy
the harmonic ratio computed by harmonic analysis kernel yields higher classification accuracy than the original harmonic ratio
with the consideration of the computational cost and complexity for implementation in DSP, BPNN is used for DSP implementation

APPENDIX D. OPTIMAL THRESHOLDING—FIGS. 40, 41A, 41B

Bladder segmentation can be taken as a bi-level analysis from ultrasound image. In another word, inside the image, there are only two kinds of objects, shadows (including real shadow or lumen, like the bladder and etc) and non-shadows. Then, automated threshold in image processing is a potential tool to segment the shadows from no-shadows. There are two widely used automated threshold methods, Otsu and Kittler & Illingworth methods. Threshold techniques can be divided into bi-level and multi-level category, depending on number of image segments. In bi-level threshold, image is segmented into two different regions. The pixels with gray values greater than a certain value T are classified as object pixels, and the others with gray values lesser than T are classified as background pixels. Otsu's method[1] chooses optimal thresholds by maximizing the between class variance. Sahoo et al.[2] found that in global threshold, Otsu's method is one of the better threshold selection methods for general real world images with regard to uniformity and shape measures. Kittler and Illingworth[3] suggested a minimum error thresholding method.

[1] Otsu, N., 1979. A Threshold Selection Using Gray Level Histograms. IEEE Trans. Systems Man Cybernet. 9, 62-69 [2]Sahoo, P. K., Soltani, S., Wong, A. K. C., 1988. SURVEY: A survey of thresholding techniques. Comput. Vision Graphics Image Process. 41, 233-260. [3] Kittler, J., Illingworth, J., 1986, Minimum Error Thresholding, Pattern Recognition, 19, 41-47.

The KI method gives very good estimation of all the shadow regions in the image, including the lumen of the bladder. The most optionally advantageous is that it gives very good estimation of the shadows behind the pubic only based on this plane itself, as we did using the statistic information from all the collected planes.

In the following, we gave examples after using KI thresholding on the Bmode images collected by 9400 system, as described for FIGS. 41A and 41B that illustrate B-mode 1058 plane after thresholding at 29 and 28.

From above examples, we can see that KI threshold method can help us estimate the location of the shadow behind the pubic bone. With appropriate post-processing, the information on all planes can be integrated and the location of the pubic bone can be estimated too.

While the preferred embodiment of the invention has been illustrated and described, many changes can be made without departing from the spirit and scope of the invention. For example, gelatinous masses may be to develop synthetic tissue and combination fluid models to further define the operational features of the neural network algorithm. Accordingly, the scope of the invention is not limited by the disclosure of the preferred embodiment.

The embodiments of the invention in which an exclusive property or privilege is claimed are defined as follows:

1. A system to detect and measure an organ cavity comprising:
  an ultrasound transceiver positioned to deliver ultrasound energy in the form of at least one scan line of at least one of a fundamental and a harmonic frequency to the organ cavity and receive echoes associated with the delivered ultrasound energy from the organ cavity; and
  an algorithm including a neural network configured to:
    signal process the received echoes;
    provide, for each scan line, a binary grading output,
    determine that a first scan line traversed non-organ tissue if the grading output is low,
    determine that the first scan line traversed organ tissue if the grading output is high,
    if the grading output is low, determine that a second or subsequent scan line traversed organ tissue and measure the organ cavity, and
    if the grading output is high, measure the organ cavity.

2. The system of claim 1, wherein the algorithm includes weighting the contributions of at least one of an ultrasound harmonic ratio, a tissue delta, a minRsum value, a cavity front wall location, and a cavity back wall location.

3. A method to detect and measure an organ cavity comprising:
  transmitting ultrasound energy in the form of at least one scan line having at least one of a fundamental and harmonic frequency to the organ cavity;
  receiving ultrasound echoes returning from the organ cavity;
  generating signals from the ultrasound echoes;
  identifying fundamental signals and harmonic signals from the generated signals;

processing the fundamental and harmonic signals using algorithms including a neural network algorithm designed for fundamental and harmonic signals;

generating, for each scan line, a binary grading output;

determining that a first scan line traversed non-organ tissue if the grading output is low;

determining that the first scan line traversed organ tissue if the grading output is high;

if the grading output is low, determining that a second or subsequent scan line traversed organ tissue and measuring the organ cavity, and if the grading output is high, measuring the organ cavity.

4. The method of claim 3, wherein the grading algorithm includes weighting the contributions of at least one of an ultrasound harmonic ratio, a tissue delta, a minRsum value, a cavity front wall location, and a cavity back wall location.

5. A non-transitory computer readable medium having instructions to execute a method to detect and measure an organ cavity comprising:

transmitting ultrasound energy in the form of at least one scan line having at least one of a fundamental and harmonic frequency to the organ cavity;

receiving ultrasound echoes returning from the organ cavity;

generating signals from the ultrasound echoes;

identifying fundamental signals and harmonic signals from the generated signals; and processing the fundamental and harmonic signals using algorithms including a neural network algorithm designed for fundamental and harmonic signals and configured to:

provide, for each scan line, a binary grading output, determine that a first scan line traversed non-organ tissue if the grading output is low, determine that the first scan line traversed organ tissue if the grading output is high, if the grading output is low, determine that a second or subsequent scan line traversed organ tissue and measure the organ cavity, and if the grading output is high, measure the organ cavity.

6. The computer readable medium of claim 5, wherein the grading algorithm includes weighting the contributions of at least one of an ultrasound harmonic ratio, a tissue delta, a minRsum value, a cavity front wall location, and a cavity back wall location.

7. The computer readable medium of claim 6, wherein the executable instructions include presenting a graphic of the cavity in relation to nearby anatomical structures.

8. The computer readable medium of claim 7, wherein the executable instructions include visualizing the pubic bone.

* * * * *